US012698503B2

(12) United States Patent
Wang et al.

(10) Patent No.: US 12,698,503 B2
(45) Date of Patent: Aug. 4, 2026

(54) ANTI-RESPIRATORY SYNCYTIAL VIRUS (RSV) ANTIBODY CELL-BASED POTENCY ASSAY

(71) Applicant: MERCK SHARP & DOHME LLC, Rahway, NJ (US)

(72) Inventors: Dai Wang, West Point, PA (US); John P. Bilello, San Carlos, CA (US); Kevin B. Gurney, Vineyard, UT (US); Ping Han, Kenilworth, NJ (US); Xi He, West Point, PA (US); Dengyun Sun, Kenilworth, NJ (US); Amy Hsu Tou, Kenilworth, NJ (US)

(73) Assignee: Merck Sharp & Dohme LLC, Rahway, NJ (US)

( * ) Notice: Subject to any disclaimer, the term of this patent is extended or adjusted under 35 U.S.C. 154(b) by 657 days.

(21) Appl. No.: 18/251,314

(22) PCT Filed: Nov. 8, 2021

(86) PCT No.: PCT/US2021/058377
§ 371 (c)(1),
(2) Date: May 1, 2023

(87) PCT Pub. No.: WO2022/103671
PCT Pub. Date: May 19, 2022

(65) Prior Publication Data
US 2023/0399648 A1      Dec. 14, 2023

Related U.S. Application Data

(60) Provisional application No. 63/112,978, filed on Nov. 12, 2020.

(51) Int. Cl.
*C12N 15/63*      (2006.01)
*C12N 7/00*       (2006.01)
*C12Q 1/66*       (2006.01)
*C12Q 1/6897*     (2018.01)

(52) U.S. Cl.
CPC .............. *C12N 15/63* (2013.01); *C12N 7/00* (2013.01); *C12Q 1/66* (2013.01); *C12Q 1/6897* (2013.01)

(58) Field of Classification Search
None
See application file for complete search history.

(56) References Cited

U.S. PATENT DOCUMENTS 6,818,216 B2      11/2004  Young et al.
2003/0130497 A1    7/2003  Bai et al.

FOREIGN PATENT DOCUMENTS

WO        1995022553 A1    8/1995
WO        2017100756 A1    6/2017

OTHER PUBLICATIONS

Remmerden, Y. et al., Virol. J., 2012: vol. 9: 7 pages.*
Collins, P. et al., Curr. Top. Microbiol. Immunol., 2013: vol. 372: 38 pages.*
Fuentes, S. et al., Vaccine, 2013, vol. 31: pp. 3987-3994.*
Beeler, Judy A. et al., Neutralization Epitopes of the F glycoprotein of Respiratory Syncytial Virus: Effect of Mutation upon Fusion Function, Journal of Virology, 1989, 2941-2950, 63(7).
Garcia-Barreno, Blanca et al., Marked Differences in the Antigenic Structure of Human Respiratory Syncytial Virus F and G glycoproteins, Journal of Virology, 1989, 925-932, 63(2).
Rameix-Welti, Marie-Anne et al., Visualizing the replication of respiratory syncytial virus in cells and in living mice, Nat. Commun., 2014, 1-10, 5:5104.
Taylor, G. et al., Monoclonal antibodies protect against respiratory syncytial virus infection in mice, Immunology, 1984, 137-142, 52.
Walsh, Edward E. et al., Protection from Respiratory Syncytial Virus Infection in Cotton Rats by Passive Transfer of Monoclonal Antibodies, Infection and Immunity, 1984, 756-758, 43(2).
Munir, Shirin et al., Nonstructural Proteins 1 and 2 of Respiratory Syncytial Virus Suppress Maturation of Human Dendritic Cells, J Virol, 82(17), 8780-8796, 2008.

* cited by examiner

*Primary Examiner* — Michael D Burkhart
(74) *Attorney, Agent, or Firm* — Tamaria Dewdney; Andrew W. Custer

(57)      ABSTRACT

The disclosure describes methods for measuring the potency of anti-Respiratory Syncytial Virus (RSV) antibody against respiratory syncytial virus in a cell culture system using an RSV reporter virus. The disclosure also describes respiratory syncytial viruses that carry a reporter gene, and expression vectors for producing an infectious recombinant respiratory syncytial virus (RSV) that carry a reporter gene.

21 Claims, 5 Drawing Sheets

Specification includes a Sequence Listing.

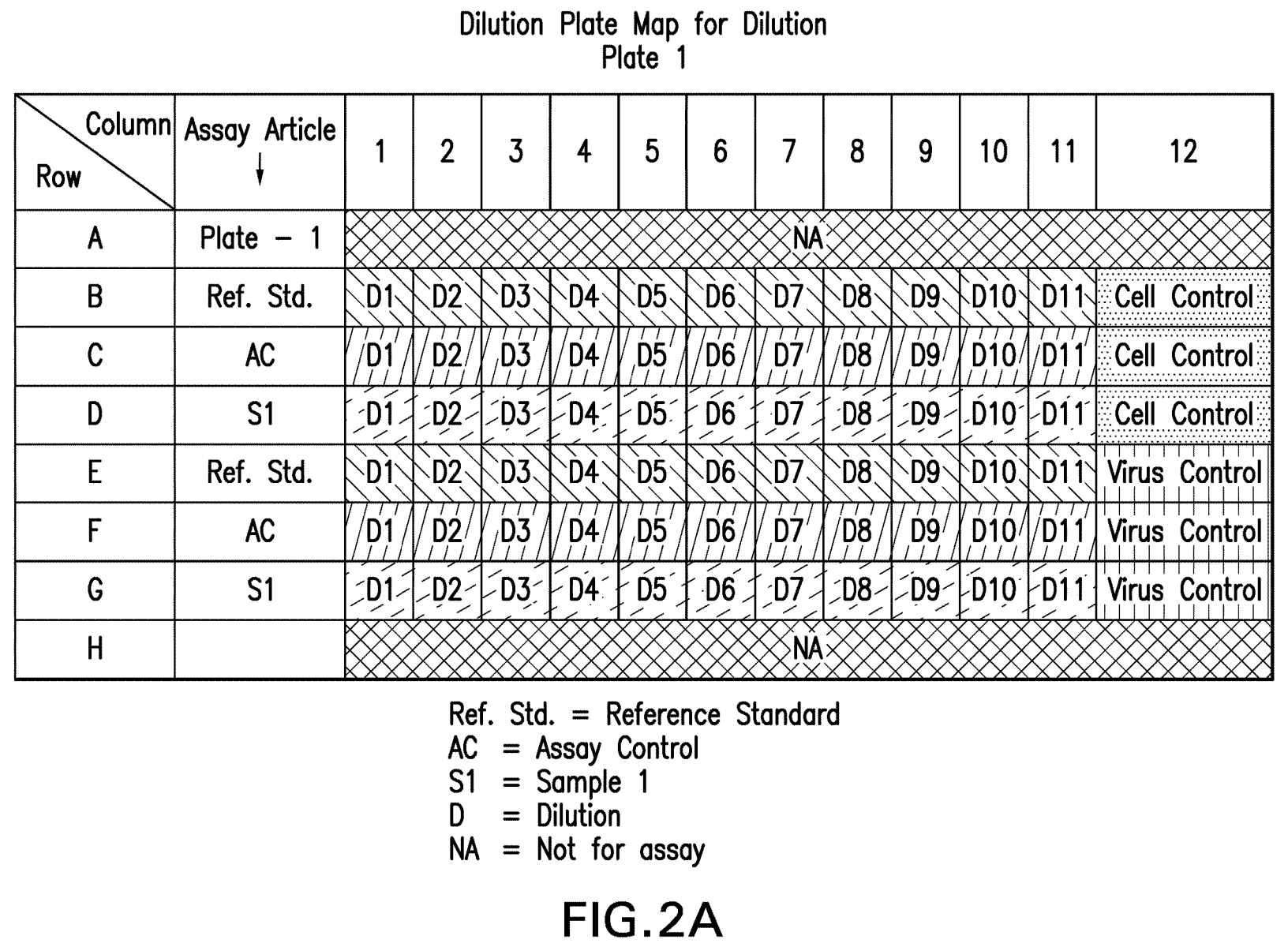

Dilution Plate Map for Dilution
Plate 1

| Column / Row | 1 | 2 | 3 | 4 | 5 | 6 | 7 | 8 | 9 | 10 | 11 | 12 |
|---|---|---|---|---|---|---|---|---|---|---|---|---|
| A | Plate – 1 | | | | | | | | | | | |
| B | Ref. Std. | D1 | D2 | D3 | D4 | D5 | D6 | D7 | D8 | D9 | D10 | D11 | Cell Control |
| C | AC | D1 | D2 | D3 | D4 | D5 | D6 | D7 | D8 | D9 | D10 | D11 | Cell Control |
| D | S1 | D1 | D2 | D3 | D4 | D5 | D6 | D7 | D8 | D9 | D10 | D11 | Cell Control |
| E | Ref. Std. | D1 | D2 | D3 | D4 | D5 | D6 | D7 | D8 | D9 | D10 | D11 | Virus Control |
| F | AC | D1 | D2 | D3 | D4 | D5 | D6 | D7 | D8 | D9 | D10 | D11 | Virus Control |
| G | S1 | D1 | D2 | D3 | D4 | D5 | D6 | D7 | D8 | D9 | D10 | D11 | Virus Control |
| H | | | | | | | | NA | | | | |

Ref. Std. = Reference Standard
AC = Assay Control
S1 = Sample 1
D = Dilution
NA = Not for assay

FIG.2A

Dilution Plate Map for Dilution
Plate 2

| Column / Row | Assay Article | 1 | 2 | 3 | 4 | 5 | 6 | 7 | 8 | 9 | 10 | 11 | 12 |
|---|---|---|---|---|---|---|---|---|---|---|---|---|---|
| A | Plate – 2 | | | | | | | NA | | | | | |
| B | S1 | D1 | D2 | D3 | D4 | D5 | D6 | D7 | D8 | D9 | D10 | D11 | Cell Control |
| C | Ref. Std. | D1 | D2 | D3 | D4 | D5 | D6 | D7 | D8 | D9 | D10 | D11 | Cell Control |
| D | AC | D1 | D2 | D3 | D4 | D5 | D6 | D7 | D8 | D9 | D10 | D11 | Cell Control |
| E | S1 | D1 | D2 | D3 | D4 | D5 | D6 | D7 | D8 | D9 | D10 | D11 | Virus Control |
| F | Ref. Std. | D1 | D2 | D3 | D4 | D5 | D6 | D7 | D8 | D9 | D10 | D11 | Virus Control |
| G | AC | D1 | D2 | D3 | D4 | D5 | D6 | D7 | D8 | D9 | D10 | D11 | Virus Control |
| H | | | | | | | | NA | | | | | |

Ref. Std. = Reference Standard
AC = Assay Control
S1 = Sample 1
D = Dilution
NA = Not for assay

FIG.2B

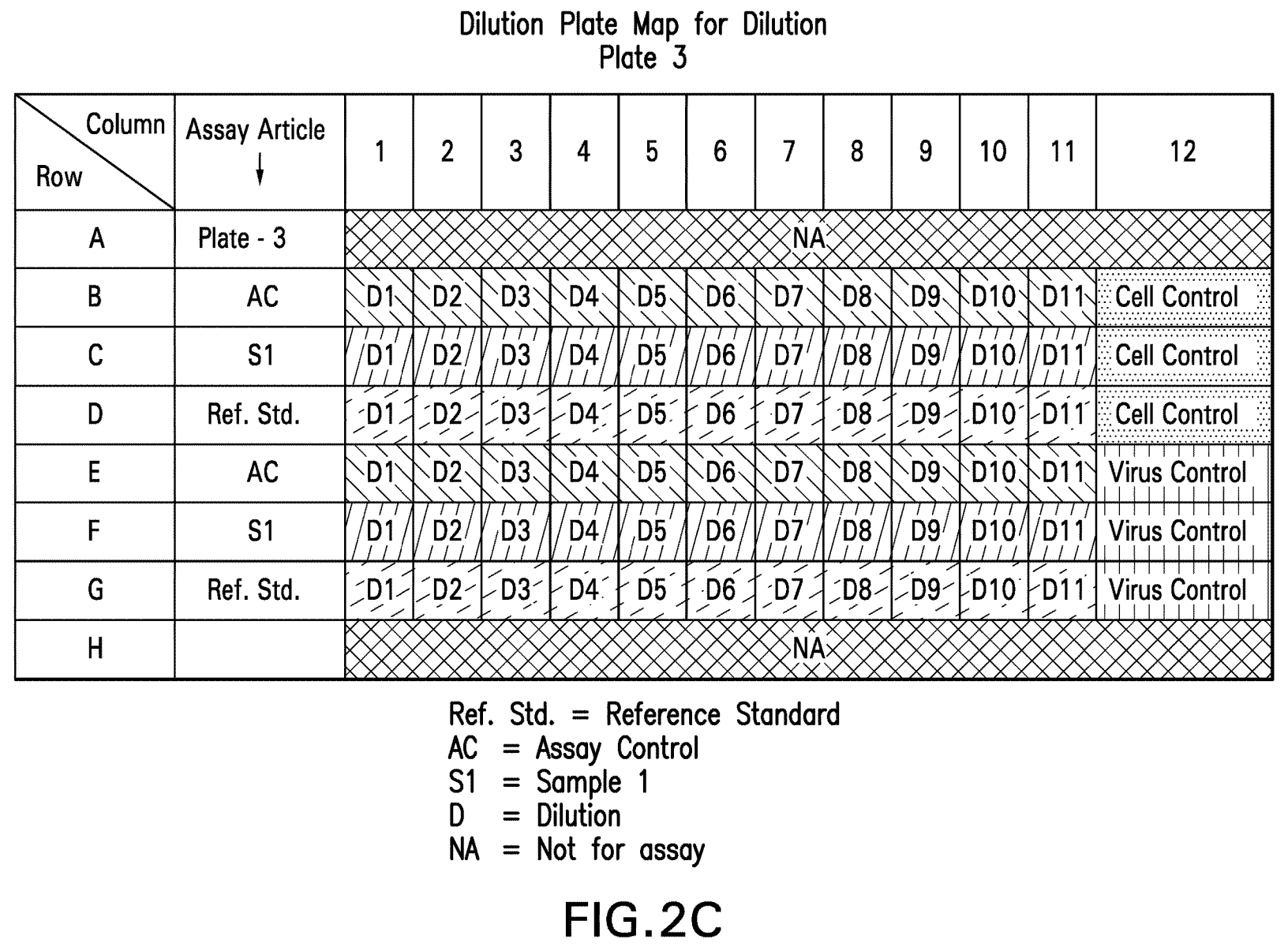

Dilution Plate Map for Dilution
Plate 3

| Column / Row | Assay Article | 1 | 2 | 3 | 4 | 5 | 6 | 7 | 8 | 9 | 10 | 11 | 12 |
|---|---|---|---|---|---|---|---|---|---|---|---|---|---|
| A | Plate - 3 | NA | | | | | | | | | | | |
| B | AC | D1 | D2 | D3 | D4 | D5 | D6 | D7 | D8 | D9 | D10 | D11 | Cell Control |
| C | S1 | D1 | D2 | D3 | D4 | D5 | D6 | D7 | D8 | D9 | D10 | D11 | Cell Control |
| D | Ref. Std. | D1 | D2 | D3 | D4 | D5 | D6 | D7 | D8 | D9 | D10 | D11 | Cell Control |
| E | AC | D1 | D2 | D3 | D4 | D5 | D6 | D7 | D8 | D9 | D10 | D11 | Virus Control |
| F | S1 | D1 | D2 | D3 | D4 | D5 | D6 | D7 | D8 | D9 | D10 | D11 | Virus Control |
| G | Ref. Std. | D1 | D2 | D3 | D4 | D5 | D6 | D7 | D8 | D9 | D10 | D11 | Virus Control |
| H | | NA | | | | | | | | | | | |

Ref. Std. = Reference Standard
AC = Assay Control
S1 = Sample 1
D = Dilution
NA = Not for assay

FIG.2C

SEQUENCE LISTING

<160> NUMBER OF SEQ ID NOS: 22

<210> SEQ ID NO 1
<211> LENGTH: 5
<212> TYPE: PRT
<213> ORGANISM: Artificial Sequence
<220> FEATURE:
<223> OTHER INFORMATION: Antibody A HC-CDR1

<400> SEQUENCE: 1

Asp Ser Ala Met Ser
1               5

<210> SEQ ID NO 2
<211> LENGTH: 19
<212> TYPE: PRT
<213> ORGANISM: Artificial Sequence
<220> FEATURE:
<223> OTHER INFORMATION: Antibody A HC-CDR2

<400> SEQUENCE: 2

Phe Ile Lys Ser Lys Thr Tyr Gly Gly Thr Lys Glu Tyr Ala Ala Ser
1               5                   10                  15

Val Lys Gly

<210> SEQ ID NO 3
<211> LENGTH: 16
<212> TYPE: PRT
<213> ORGANISM: Artificial Sequence
<220> FEATURE:
<223> OTHER INFORMATION: Antibody A HC-CDR3

<400> SEQUENCE: 3

Gly Ala Pro Tyr Gly Gly Asn Ser Asp Tyr Tyr Tyr Gly Leu Asp Val
1               5                   10                  15

<210> SEQ ID NO 4
<211> LENGTH: 11
<212> TYPE: PRT
<213> ORGANISM: Artificial Sequence
<220> FEATURE:
<223> OTHER INFORMATION: Antibody A LC-CDR1

<400> SEQUENCE: 4

Arg Thr Ser Gln Asp Val Arg Gly Ala Leu Ala
1               5                   10

<210> SEQ ID NO 5
<211> LENGTH: 7
<212> TYPE: PRT
<213> ORGANISM: Artificial Sequence
<220> FEATURE:
<223> OTHER INFORMATION: Antibody A LC-CDR2

<400> SEQUENCE: 5

Asp Ala Ser Ser Leu Glu Thr
1               5

<210> SEQ ID NO 6
<211> LENGTH: 9
<212> TYPE: PRT
<213> ORGANISM: Artificial Sequence
<220> FEATURE:
<223> OTHER INFORMATION: Antibody A LC-CDR3

<400> SEQUENCE: 6

-continued

```
Gln Gln Phe Leu Asp Phe Pro Phe Thr
1               5

<210> SEQ ID NO 7
<211> LENGTH: 127
<212> TYPE: PRT
<213> ORGANISM: Artificial Sequence
<220> FEATURE:
<223> OTHER INFORMATION: Antibody A VH

<400> SEQUENCE: 7

Glu Val Gln Leu Val Glu Ser Gly Gly Gly Leu Val Arg Pro Gly Arg
1               5                   10                  15

Ser Leu Arg Leu Ser Cys Thr Val Ser Gly Phe Ser Phe Asp Asp Ser
                20                  25                  30

Ala Met Ser Trp Val Arg Gln Ala Pro Gly Lys Gly Leu Glu Trp Ile
            35                  40                  45

Ser Phe Ile Lys Ser Lys Thr Tyr Gly Gly Thr Lys Glu Tyr Ala Ala
        50                  55                  60

Ser Val Lys Gly Arg Phe Thr Ile Ser Arg Asp Asp Ser Lys Asn Ile
65                  70                  75                  80

Ala Tyr Leu Gln Met Asn Ser Leu Lys Thr Glu Asp Thr Ala Val Tyr
                85                  90                  95

Tyr Cys Thr Arg Gly Ala Pro Tyr Gly Gly Asn Ser Asp Tyr Tyr Tyr
            100                 105                 110

Gly Leu Asp Val Trp Gly Gln Gly Thr Thr Val Thr Val Ser Ser
        115                 120                 125

<210> SEQ ID NO 8
<211> LENGTH: 127
<212> TYPE: PRT
<213> ORGANISM: Artificial Sequence
<220> FEATURE:
<223> OTHER INFORMATION: Antibody A VL

<400> SEQUENCE: 8

Glu Val Gln Leu Val Glu Ser Gly Gly Gly Leu Val Arg Pro Gly Arg
1               5                   10                  15

Ser Leu Arg Leu Ser Cys Thr Val Ser Gly Phe Ser Phe Asp Asp Ser
                20                  25                  30

Ala Met Ser Trp Val Arg Gln Ala Pro Gly Lys Gly Leu Glu Trp Ile
            35                  40                  45

Ser Phe Ile Lys Ser Lys Thr Tyr Gly Gly Thr Lys Glu Tyr Ala Ala
        50                  55                  60

Ser Val Lys Gly Arg Phe Thr Ile Ser Arg Asp Asp Ser Lys Asn Ile
65                  70                  75                  80

Ala Tyr Leu Gln Met Asn Ser Leu Lys Thr Glu Asp Thr Ala Val Tyr
                85                  90                  95

Tyr Cys Thr Arg Gly Ala Pro Tyr Gly Gly Asn Ser Asp Tyr Tyr Tyr
            100                 105                 110

Gly Leu Asp Val Trp Gly Gln Gly Thr Thr Val Ile Val Ser Ser
        115                 120                 125

<210> SEQ ID NO 9
<211> LENGTH: 457
<212> TYPE: PRT
<213> ORGANISM: Artificial Sequence
<220> FEATURE:
<223> OTHER INFORMATION: Antibody A Heavy chain
```

-continued

```
<400> SEQUENCE: 9

Glu Val Gln Leu Val Glu Ser Gly Gly Gly Leu Val Arg Pro Gly Arg
1               5                   10                  15

Ser Leu Arg Leu Ser Cys Thr Val Ser Gly Phe Ser Phe Asp Asp Ser
                20                  25                  30

Ala Met Ser Trp Val Arg Gln Ala Pro Gly Lys Gly Leu Glu Trp Ile
            35                  40                  45

Ser Phe Ile Lys Ser Lys Thr Tyr Gly Gly Thr Lys Glu Tyr Ala Ala
    50                  55                  60

Ser Val Lys Gly Arg Phe Thr Ile Ser Arg Asp Asp Ser Lys Asn Ile
65                  70                  75                  80

Ala Tyr Leu Gln Met Asn Ser Leu Lys Thr Glu Asp Thr Ala Val Tyr
                85                  90                  95

Tyr Cys Thr Arg Gly Ala Pro Tyr Gly Gly Asn Ser Asp Tyr Tyr Tyr
            100                 105                 110

Gly Leu Asp Val Trp Gly Gln Gly Thr Thr Val Thr Val Ser Ser Ala
            115                 120                 125

Ser Thr Lys Gly Pro Ser Val Phe Pro Leu Ala Pro Ser Ser Lys Ser
    130                 135                 140

Thr Ser Gly Gly Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
                165                 170                 175

Val His Thr Phe Pro Ala Val Leu Gln Ser Ser Gly Leu Tyr Ser Leu
            180                 185                 190

Ser Ser Val Val Thr Val Pro Ser Ser Ser Leu Gly Thr Gln Thr Tyr
    195                 200                 205

Ile Cys Asn Val Asn His Lys Pro Ser Asn Thr Lys Val Asp Lys Lys
    210                 215                 220

Val Glu Pro Lys Ser Cys Asp Lys Thr His Thr Cys Pro Pro Cys Pro
225                 230                 235                 240

Ala Pro Glu Leu Leu Gly Gly Pro Ser Val Phe Leu Phe Pro Pro Lys
            245                 250                 255

Pro Lys Asp Thr Leu Tyr Ile Thr Arg Glu Pro Glu Val Thr Cys Val
            260                 265                 270

Val Val Asp Val Ser His Glu Asp Pro Glu Val Lys Phe Asn Trp Tyr
            275                 280                 285

Val Asp Gly Val Glu Val His Asn Ala Lys Thr Lys Pro Arg Glu Glu
    290                 295                 300

Gln Tyr Asn Ser Thr Tyr Arg Val Val Ser Val Leu Thr Val Leu His
305                 310                 315                 320

Gln Asp Trp Leu Asn Gly Lys Glu Tyr Lys Cys Lys Val Ser Asn Lys
                325                 330                 335

Ala Leu Pro Ala Pro Ile Glu Lys Thr Ile Ser Lys Ala Lys Gly Gln
            340                 345                 350

Pro Arg Glu Pro Gln Val Tyr Thr Leu Pro Pro Ser Arg Asp Glu Leu
            355                 360                 365

Thr Lys Asn Gln Val Ser Leu Thr Cys Leu Val Lys Gly Phe Tyr Pro
    370                 375                 380

Ser Asp Ile Ala Val Glu Trp Glu Ser Asn Gly Gln Pro Glu Asn Asn
385                 390                 395                 400

Tyr Lys Thr Thr Pro Pro Val Leu Asp Ser Asp Gly Ser Phe Phe Leu
                405                 410                 415
```

-continued

Tyr Ser Lys Leu Thr Val Asp Lys Ser Arg Trp Gln Gln Gly Asn Val
        420                 425                 430

Phe Ser Cys Ser Val Met His Glu Ala Leu His Asn His Tyr Thr Gln
        435                 440                 445

Lys Ser Leu Ser Leu Ser Pro Gly Lys
    450                 455

<210> SEQ ID NO 10
<211> LENGTH: 214
<212> TYPE: PRT
<213> ORGANISM: Artificial Sequence
<220> FEATURE:
<223> OTHER INFORMATION: Antibody A Light chain

<400> SEQUENCE: 10

Asp Ile Gln Met Thr Gln Ser Pro Ser Ser Leu Ser Ala Ser Val Gly
1                   5                  10                  15

Asp Arg Val Thr Ile Thr Cys Arg Thr Ser Gln Asp Val Arg Gly Ala
        20                  25                  30

Leu Ala Trp Tyr Gln Gln Lys Pro Gly Lys Ala Pro Lys Leu Leu Ile
        35                  40                  45

Phe Asp Ala Ser Ser Leu Glu Thr Gly Val Pro Ser Arg Phe Ser Gly
    50                  55                  60

Ser Gly Ser Gly Thr Val Phe Thr Leu Thr Ile Ser Ser Leu Gln Pro
65                  70                  75                  80

Glu Asp Phe Ala Ala Tyr Tyr Cys Gln Gln Phe Leu Asp Phe Pro Phe
                85                  90                  95

Thr Phe Gly Gln Gly Thr Arg Leu Glu Ile Lys Arg Thr Val Ala Ala
        100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
        180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 11
<211> LENGTH: 1319
<212> TYPE: DNA
<213> ORGANISM: Artificial Sequence
<220> FEATURE:
<223> OTHER INFORMATION: rpsL-neo cassette

<400> SEQUENCE: 11
ggcctggtga tgatggcggg atcgttgtat atttcttgac accttttcgg catcgcccta        60
aaattcggcg tcctcatatt gtgtgaggac gttttattac gtgtttacga agcaaaagct       120
aaaaccagga gctatttaat ggcaacagtt aaccagctgg tacgcaaacc acgtgctcgc       180
aaagttgcga aaagcaacgt gcctgcgctg gaagcatgcc cgcaaaaacg tggcgtatgt       240

-continued

```
actcgtgtat atactaccac tcctaaaaaa ccgaactccg cgctgcgtaa agtatgccgt      300
gttcgtctga ctaacggttt cgaagtgact tcctacatcg gtggtgaagg tcacaacctg      360
caggagcact ccgtgatcct gatccgtggc ggtcgtgtta aagacctccc gggtgttcgt      420
taccacaccg tacgtggtgc gcttgactgc tccggcgtta aagaccgtaa gcaggctcgt      480
tccaagtatg gcgtgaagcg tcctaaggct taaggaggac aatcatgatt gaacaagatg      540
gattgcacgc aggttctccg gccgcttggg tggagaggct attcggctat gactgggcac      600
aacagacaat cggctgctct gatgccgccg tgttccggct gtcagcgcag gggcgcccgg      660 ttcttttttgt caagaccgac ctgtccggtg ccctgaatga actgcaggac gaggcagcgc      720
ggctatcgtg gctggccacg acgggcgttc cttgcgcagc tgtgctcgac gttgtcactg      780
aagcgggaag ggactggctg ctattgggcg aagtgccggg gcaggatctc ctgtcatctc      840
accttgctcc tgccgagaaa gtatccatca tggctgatgc aatgcggcgg ctgcatacgc      900
ttgatccggc tacctgccca ttcgaccacc aagcgaaaca tcgcatcgag cgagcacgta      960
ctcggatgga agccggtctt gtcgatcagg atgatctgga cgaagagcat caggggctcg     1020
cgccagccga actgttcgcc aggctcaagg cgcgcatgcc cgacggcgag gatctcgtcg     1080
tgacccatgg cgatgcctgc ttgccgaata tcatggtgga aaatggccgc ttttctggat     1140
tcatcgactg tggccggctg ggtgtggcgg accgctatca ggacatagcg ttggctaccc     1200
gtgatattgc tgaagagctt ggcggcgaat gggctgaccg cttcctcgtg ctttacggta     1260
tcgccgctcc cgattcgcag cgcatcgcct tctatcgcct tcttgacgag ttcttctga     1319

<210> SEQ ID NO 12
<211> LENGTH: 75
<212> TYPE: DNA
<213> ORGANISM: Artificial Sequence
<220> FEATURE:
<223> OTHER INFORMATION: Forward primer for rpsL cassette

<400> SEQUENCE: 12
cttcgtgaag cttgttcacg tatgtttcca tatttgcccc accctacgcg tggcctggtg       60
atgatggcgg gatcg                                                        75

<210> SEQ ID NO 13
<211> LENGTH: 72
<212> TYPE: DNA
<213> ORGANISM: Artificial Sequence
<220> FEATURE:
<223> OTHER INFORMATION: Reverse primer for rpsL cassette

<400> SEQUENCE: 13
ctaaccaccc ggaaaaaatc tataatatag ttacaaaaaa aggaaacgcg tcagaagaac       60
tcgtcaagaa gg                                                           72

<210> SEQ ID NO 14
<211> LENGTH: 15199
<212> TYPE: DNA
<213> ORGANISM: Artificial Sequence
<220> FEATURE:
<223> OTHER INFORMATION: RSV A2

<400> SEQUENCE: 14
acttgcataa accaaaaaaa tggggcaaat aagaatttga taagtaccac ttaaatttaa       60
ctcccttggt tagagatggg cagcaattca ttgagtatga taaaagttag attacaaaat      120
```

-continued

```
ttgtttgaca atgatgaagt agcattgtta aaaataacat gctatactga taaattaata     180
catttaacta acgctttggc taaggcagtg atacatacaa tcaaattgaa tggcattgtg     240
tttgtgcatg ttattacaag tagtgatatt tgccctaata ataatattgt agtaaaatcc     300
aatttcacaa caatgccagt actacaaaat ggaggttata tatgggaaat gatggaatta     360
acacattgct ctcaacctaa tggtctacta gatgacaatt gtgaaattaa attctccaaa     420
aaactaagtg attcaacaat gaccaattat atgaatcaat tatctgaatt acttggattt     480
gatcttaatc cataaattat aattaatatc aactagcaaa tcaatgtcac taacaccatt     540
agttaatata aaacttaaca gaagacaaaa atggggcaaa taaatcaatt cagccaaccc     600
aaccatggac acaacccaca atgataatac accacaaaga ctgatgatca cagacatgag     660
accgttgtca cttgagacca taataacatc actaaccaga gacatcataa cacacaaatt     720
tatatacttg ataaatcatg aatgcatagt gagaaaactt gatgaaaaac aggccacatt     780
tacattcctg gtcaactatg aaatgaaact attacacaaa gtaggaagca ctaaatataa     840
aaaatatact gaatacaaca caaaatatgg cactttccct atgccaatat tcatcaatca     900
tgatgggttc ttagaatgca ttggcattaa gcctacaaag catactccca taatatacaa     960
gtatgatctc aatccataaa tttcaacaca atattcacac aatctaaaac aacaactcta    1020
tgcataacta tactccatag tccagatgga gcctgaaaat tatagtaatt taaaattaag    1080
gagagatata agatagaaga tggggcaaat acaaagatgg ctcttagcaa agtcaagttg    1140
aatgatacac tcaacaaaga tcaacttctg tcatccagca aatacaccat ccaacggagc    1200
acaggagata gtattgatac tcctaattat gatgtgcaga aacacatcaa taagttatgt    1260
ggcatgttat taatcacaga agatgctaat cataaattca ctgggttaat aggtatgtta    1320
tatgcgatgt ctaggttagg aagagaagac accataaaaa tactcagaga tgcgggatat    1380
catgtaaaag caaatggagt agatgtaaca acacatcgtc aagacattaa tggaaaagaa    1440
atgaaatttg aagtgttaac attggcaagc ttaacaactg aaattcaaat caacattgag    1500
atagaatcta gaaatcccta caaaaaaatg ctaaaagaaa tgggagaggt agctccagaa    1560
tacaggcatg actctcctga ttgtgggatg ataatattat gtatagcagc attagtaata    1620
actaaattag cagcagggga cagatctggt cttacagccg tgattaggag agctaataat    1680
gtcctaaaaa atgaaatgaa acgttacaaa ggcttactac ccaaggacat agccaacagc    1740
ttctatgaag tgtttgaaaa acatcccac tttatagatg tttttgttca ttttggtata    1800
gcacaatctt ctaccagagg tggcagtaga gttgaaggga tttttgcagg attgtttatg    1860
aatgcctatg gtgcagggca agtgatgtta cggtggggag tcttagcaaa atcagttaaa    1920
aatattatgt taggacatgc tagtgtgcaa gcagaaatgg aacaagttgt tgaggtttat    1980
gaatatgccc aaaaattggg tggtgaagca ggattctacc atatattgaa caacccaaaa    2040
gcatcattat tatctttgac tcaatttcct cacttctcca gtgtagtatt aggcaatgct    2100
gctggcctag gcataatggg agagtacaga ggtacaccga ggaatcaaga tctatatgat    2160
gcagcaaagg catatgctga caactcaaa gaaaatggtg tgattaacta cagtgtacta    2220
gacttgacag cagaagaact agaggctatc aaacatcagc ttaatccaaa agataatgat    2280
gtagagcttt gagttaataa aaaatggggc aaataaatca tcatggaaaa gtttgctcct    2340
gaattccatg gagaagatgc aaacaacagg gctactaaat tcctagaatc aataaagggc    2400
aaattcacat cacccaaaga tcccaagaaa aaagatagta tcatatctgt caactcaata    2460
gatatagaag taaccaaaga aagccctata acatcaaatt caactattat caacccaaca    2520
```

-continued

```
aatgagacag atgatactgc agggaacaag cccaattatc aaagaaaacc tctagtaagt    2580
ttcaaagaag accctacacc aagtgataat cccttttcta aactatacaa agaaaccata    2640
gaaacatttg ataacaatga agaagaatcc agctattcat acgaagaaat aaatgatcag    2700
acaaacgata atataacagc aagattagat aggattgatg aaaaattaag tgaaatacta    2760
ggaatgcttc acacattagt agtggcaagt gcaggaccta catctgctcg ggatggtata    2820
agagatgcca tgattggttt aagagaagaa atgatagaaa aaatcagaac tgaagcatta    2880
atgaccaatg acagattaga agctatggca agactcagga atgaggaaag tgaaaagatg    2940
gcaaaagaca catcagatga agtgtctctc aatccaacat cagagaaatt gaacaaccta    3000
ttggaaggga atgatagtga caatgatcta tcacttgaag atttctgatt agttaccact    3060
cttcacatca acacacaata ccaacagaag accaacaaac taaccaaccc aatcatccaa    3120
ccaaacatcc atccgccaat cagccaaaca gccaacaaaa caaccagcca atccaaaact    3180
aaccacccgg aaaaaatcta taatatagtt acaaaaaaag gaaagggtgg ggcaaatatg    3240
gaaacatacg tgaacaagct tcacgaaggc tccacataca cagctgctgt tcaatacaat    3300
gtcttagaaa aagacgatga ccctgcatca cttacaatat gggtgcccat gttccaatca    3360
tctatgccag cagatttact tataaaagaa ctagctaatg tcaacatact agtgaaacaa    3420
atatccacac ccaagggacc ttcactaaga gtcatgataa actcaagaag tgcagtgcta    3480
gcacaaatgc ccagcaaatt taccatatgc gctaatgtgt ccttggatga aagaagcaaa    3540
ctagcatatg atgtaaccac accctgtgaa atcaaggcat gtagtctaac atgcctaaaa    3600
tcaaaaaata tgttgactac agttaaagat ctcactatga agacactcaa ccctacacat    3660
gatattattg ctttatgtga atttgaaaac atagtaacat caaaaaaagt cataataccaa   3720 acatacctaa gatccatcag tgtcagaaat aaagatctga acacacttga aaatataaca    3780
accactgaat tcaaaaatgc tatcacaaat gcaaaaatca tcccttactc aggattacta    3840
ttagtcatca cagtgactga caacaaagga gcattcaaat acataaagcc acaaagtcaa    3900
ttcatagtag atcttggagc ttacctagaa aagaaagta tatattatgt taccacaaat    3960
tggaagcaca cagctacacg atttgcaatc aaacccatgg aagattaacc tttttcctct    4020
acatcagtgt gttaattcat acaaactttc tacctacatt cttcacttca ccatcacaat    4080
cacaaacact ctgtggttca accaatcaaa caaaacttat ctgaagtccc agatcatccc    4140
aagtcattgt ttatcagatc tagtactcaa ataagttaat aaaaaatata cacatggggc    4200
aaataatcat tggaggaaat ccaactaatc acaatatctg ttaacataga caagtccaca    4260
caccatacag aatcaaccaa tggaaaatac atccataaca atagaattct caagcaaatt    4320
ctggccttac tttacactaa tacacatgat cacaacaata atctctttgc taatcataat    4380
ctccatcatg attgcaatac taaacaaact ttgtgaatat aacgtattcc ataacaaaac    4440
ctttgagtta ccaagagctc gagtcaacac atagcattca tcaatccaac agcccaaaac    4500
agtaaccttg catttaaaaa tgaacaaccc ctacctcttt acaacacctc attaacatcc    4560
caccatgcaa accactatcc atactataaa gtagttaatt aaaaatagtc ataacaatga    4620
actaggatat caagactaac aataacattg gggcaaatgc aaacatgtcc aaaaacaagg    4680
accaacgcac cgctaagaca ttagaaagga cctgggacac tctcaatcat ttattattca    4740
tatcatcgtg cttatataag ttaaatctta aatctgtagc acaaatcaca ttatccattc    4800
tggcaatgat aatctcaact tcacttataa ttgcagccat catattcata gcctcggcaa    4860
```

-continued

```
accacaaagt cacaccaaca actgcaatca tacaagatgc aacaagccag atcaagaaca      4920 caacccaac atacctcacc cagaatcctc agcttggaat cagtccctct aatccgtctg       4980
aaattacatc acaaatcacc accatactag cttcaacaac accaggagtc aagtcaaccc      5040
tgcaatccac aacagtcaag accaaaaaca caacaacaac tcaaacacaa cccagcaagc      5100
ccaccacaaa acaacgccaa aacaaaccac caagcaaacc caataatgat tttcactttg      5160
aagtgttcaa ctttgtaccc tgcagcatat gcagcaacaa tccaacctgc tgggctatct      5220
gcaaaagaat accaaacaaa aaaccaggaa agaaaaccac taccaagccc acaaaaaaac      5280
caaccctcaa gacaaccaaa aaagatccca aacctcaaac cactaaatca aaggaagtac      5340
ccaccaccaa gcccacagaa gagccaacca tcaacaccac caaaacaaac atcataacta      5400
cactactcac ctccaacacc acaggaaatc cagaactcac aagtcaaatg gaaaccttcc      5460
actcaacttc ctccgaaggc aatccaagcc cttctcaagt ctctacaaca tccgagtacc      5520
catcacaacc ttcatctcca cccaacacac cacgccagta gttacttaaa aacatatat      5580 cacaaaaagc catgaccaac ttaaacagaa tcaaaataaa ctctggggca aataacaatg      5640
gagttgctaa tcctcaaagc aaatgcaatt accacaatcc tcactgcagt cacattttgt      5700
tttgcttctg gtcaaaacat cactgaagaa ttttatcaat caacatgcag tgcagttagc      5760
aaaggctatc ttagtgctct gagaactggt tggtatacca gtgttataac tatagaatta      5820
agtaatatca aggaaaataa gtgtaatgga acagatgcta aggtaaaatt gataaaacaa      5880
gaattagata aatataaaaa tgctgtaaca gaattgcagt tgctcatgca aagcacacca      5940
ccaacaaaca atcgagccag aagagaacta ccaaggttta tgaattatac actcaacaat      6000
gccaaaaaaa ccaatgtaac attaagcaag aaaaggaaaa gaagatttct tgtttttttg      6060
ttaggtgttg gatctgcaat cgccagtggc gttgctgtat ctaaggtcct gcacctagaa      6120
ggggaagtga acaagatcaa aagtgctcta ctatccacaa acaaggctct agtcagctta      6180
tcaaatggag ttagtgtctt aaccagcaaa gtgttagacc tcaaaaacta tatagataaa      6240
caattgttac ctattgtgaa caagcaaagc tgcagcatat caaatataga aactgtgata      6300
gagttccaac aaaagaacaa cagactacta gagattacca gggaatttag tgttaatgca      6360
ggtgtaacta cacctgtaag cacttacatg ttaactaata gtgaattatt gtcattaatc      6420
aatgatatgc ctataacaaa tgatcagaaa aagttaatgt ccaacaatgt tcaaatagtt      6480
agacagcaaa gttactctat catgtccata ataaaagagg aagtcttagc atatgtagta      6540
caattaccac tatatggtgt tatagataca ccctgttgga aactacacac atcccctcta      6600
tgtacaacca acacaaaaga agggtccaac atctgtttaa caagaactga cagaggatgg      6660
tactgtgaca atgcaggatc agtatctttc ttcccacaag ctgaaacatg taaagttcaa      6720
tcaaatcgag tattttgtga cacaatgaac agtttaacat taccaagtga aataaatctc      6780
tgcaatgttg acatattcaa ccccaaatat gattgtaaaa ttatgacttc aaaaacagat      6840
gtaagcagct ccgttatcac atctctagga gccattgtgt catgctatgg caaaactaaa      6900
tgtacagcat ccaataaaaa tcgtggaatc ataaagacat tttctaacgg gtgcgattat      6960
gtatcaaata aagggatgga cactgtgtct gtaggtaaca cattatatta tgtaaataag      7020
caagaaggta aaagtctcta tgtaaaaggt gaaccaataa taaatttcta tgacccatta      7080
gtattcccct ctgatgaatt tgatgcatca atatctcaag tcaacgagaa gattaaccag      7140
agcctagcat ttattcgtaa atccgatgaa ttattacata atgtaaatgc tggtaaatcc      7200
accacaaata tcatgataac tactataatt atagtgatta tagtaatatt gttatcatta      7260
```

-continued

```
attgctgttg gactgctctt atactgtaag gccagaagca caccagtcac actaagcaaa      7320
gatcaactga gtggtataaa taatattgca tttagtaact aaataaaaat agcacctaat      7380
catgttctta caatggttta ctatctgctc atagacaacc catctgtcat tggattttct      7440
taaaatctga acttcatcga aactctcatc tataaaccat ctcacttaca ctatttaagt      7500
agattcctag tttatagtta tataaaacac aattgaatgc cagattaact taccatctgt      7560
aaaaatgaaa actggggcaa atatgtcacg aaggaatcct tgcaaatttg aaattcgagg      7620
tcattgctta aatggtaaga ggtgtcattt tagtcataat tattttgaat ggccacccca      7680
tgcactgctt gtaagacaaa actttatgtt aaacagaata cttaagtcta tggataaaag      7740
tatagatacc ttatcagaaa taagtggagc tgcagagttg gacagaacag aagagtatgc      7800
tcttggtgta gttggagtgc tagagagtta tataggatca ataaacaata taactaaaca      7860
atcagcatgt gttgccatga gcaaactcct cactgaactc aatagtgatg atatcaaaaa      7920
gctgagggac aatgaagagc taaattcacc caagataaga gtgtacaata ctgtcatatc      7980
atatattgaa agcaacagga aaaacaataa acaaactatc catctgttaa aaagattgcc      8040
agcagacgta ttgaagaaaa ccatcaaaaa cacattggat atccataaga gcataaccat      8100
caacaaccca aaagaatcaa ctgttagtga tacaaatgac catgccaaaa ataatgatac      8160
tacctgacaa atatccttgt agtataactt ccatactaat aacaagtaga tgtagagtta      8220
ctatgtataa tcaaaagaac acactatatt tcaatcaaaa caacccaaat aaccatatgt      8280
actcaccgaa tcaaacattc aatgaaatcc attggacctc tcaagaattg attgacacaa      8340
ttcaaatttt tctacaacat ctaggtatta ttgaggatat atatacaata tatatattag      8400
tgtcataaca ctcaattcta acactcacca catcgttaca ttattaattc aaacaattca      8460
agttgtggga caaaatggat cccattatta atggaaattc tgctaatgtt tatctaaccg      8520
atagttattt aaaaggtgtt atctctttct cagagtgtaa tgctttagga agttacatat      8580
tcaatggtcc ttatctcaaa aatgattata ccaacttaat tagtagacaa aatccattaa      8640
tagaacacat gaatctaaag aaactaaata taacacagtc cttaatatct aagtatcata      8700
aaggtgaaat aaaattagaa gaacctactt attttcagtc attacttatg acatacaaga      8760
gtatgacctc gtcagaacag attgctacca ctaatttact taaaaagata ataagaagag      8820
ctatagaaat aagtgatgtc aaagtctatg ctatattgaa taaactaggg cttaaagaaa      8880
aggacaagat taaatccaac aatggacaag atgaagacaa ctcagttatt acgaccataa      8940
tcaaagatga tatactttca gctgttaaag ataatcaatc tcatcttaaa gcagacaaaa      9000
atcactctac aaaacaaaaa gacacaatca aaacaacact cttgaagaaa ttgatgtgtt      9060
caatgcaaca tcctccatca tggttaatac attggtttaa cttatacaca aaattaaaca      9120
acatattaac acagtatcga tcaaatgagg taaaaaacca tgggtttaca ttgatagata      9180
atcaaactct tagtggattt caatttattt tgaaccaata tggttgtata gtttatcata      9240
aggaactcaa aagaattact gtgacaacct ataatcaatt cttgacatgg aaagatatta      9300
gccttagtag attaaatgtt tgtttaatta catggattag taactgcttg aacacattaa      9360
ataaaagctt aggcttaaga tgcggattca ataatgttat cttgacacaa ctattccttt      9420
atggagattg tatactaaag ctatttcaca atgaggggtt ctacataata aaagaggtag      9480
agggatttat tatgtctcta attttaaata taacagaaga agatcaattc agaaaacgat      9540
tttataatag tatgctcaac aacatcacag atgctgctaa taaagctcag aaaaatctgc      9600
```

-continued

```
tatcaagagt atgtcataca ttattagata agacagtgtc cgataatata ataaatggca  9660
gatggataat tctattaagt aagttcctta aattaattaa gcttgcaggt gacaataacc  9720
ttaacaatct gagtgaacta tattttttgt tcagaatatt tggacaccca atggtagatg  9780
aaagacaagc catggatgct gttaaaatta attgcaatga gaccaaattt tacttgttaa  9840
gcagtctgag tatgttaaga ggtgccttta tatatagaat tataaaaggg tttgtaaata  9900
attacaacag atggcctact ttaagaaatg ctattgtttt acccttaaga tggttaactt  9960
actataaact aaacacttat ccttctttgt tggaacttac agaaagagat ttgattgtgt 10020
tatcaggact acgtttctat cgtgagtttc ggttgcctaa aaaagtggat cttgaaatga 10080
ttataaatga taaagctata tcacctccta aaaatttgat atggactagt ttccctagaa 10140
attacatgcc atcacacata caaaactata tagaacatga aaaattaaaa ttttccgaga 10200
gtgataaatc aagaagagta ttagagtatt atttaagaga taacaaattc aatgaatgtg 10260
atttatacaa ctgtgtagtt aatcaaagtt atctcaacaa ccctaatcat gtggtatcat 10320
tgacaggcaa agaaagagaa ctcagtgtag gtagaatgtt tgcaatgcaa ccgggaatgt 10380
tcagacaggt tcaaatattg gcagagaaaa tgatagctga aaacatttta caattctttc 10440
ctgaaagtct tacaagatat ggtgatctag aactacaaaa aatattagaa ttgaaagcag 10500
gaataagtaa caaatcaaat cgctacaatg ataattacaa caattacatt agtaagtgct 10560
ctatcatcac agatctcagc aaattcaatc aagcatttcg atatgaaacg tcatgtattt 10620
gtagtgatgt gctggatgaa ctgcatggtg tacaatctct attttcctgg ttacatttaa 10680
ctattcctca tgtcacaata atatgcacat ataggcatgc accccctat ataggagatc 10740 atattgtaga tcttaacaat gtagatgaac aaagtggatt atatagatat cacatgggtg 10800
gcatcgaagg gtggtgtcaa aaactgtgga ccatagaagc tatatcacta ttggatctaa 10860
tatctctcaa agggaaattc tcaattactg ctttaattaa tggtgacaat caatcaatag 10920
atataagcaa accaatcaga ctcatggaag gtcaaactca tgctcaagca gattatttgc 10980
tagcattaaa tagccttaaa ttactgtata aagagtatgc aggcataggc cacaaattaa 11040
aaggaactga gacttatata tcacgagata tgcaatttat gagtaaaaca attcaacata 11100
acggtgtata ttacccagct agtataaaga aagtcctaag agtgggaccg tggataaaca 11160
ctatacttga tgatttcaaa gtgagtctag aatctatagg tagtttgaca caagaattag 11220
aatatagagg tgaaagtcta ttatgcagtt taatatttag aaatgtatgg ttatataatc 11280
agattgctct acaattaaaa aatcatgcat tatgtaacaa taaactatat ttggacatat 11340
taaaggttct gaaacactta aaaacctttt ttaatcttga taatattgat acagcattaa 11400
cattgtatat gaatttaccc atgttatttg gtggtggtga tcccaacttg ttatatcgaa 11460
gtttctatag aagaactcct gacttcctca cagaggctat agttcactct gtgttcatac 11520
ttagttatta tacaaaccat gacttaaaag ataaacttca agatctgtca gatgatagat 11580
tgaataagtt cttaacatgc ataatcacgt ttgacaaaaa ccctaatgct gaattcgtaa 11640
cattgatgag agatcctcaa gctttagggt ctgagagaca agctaaaatt actagcgaaa 11700
tcaatagact ggcagttaca gaggtttttga gtacagctcc aaacaaaata ttctccaaaa 11760
gtgcacaaca ttatactact acagagatag atctaaatga tattatgcaa aatatagaac 11820
ctacatatcc tcatgggcta agagttgttt atgaaagttt acccttttat aaagcagaga 11880
aaatagtaaa tcttatatca ggtacaaaat ctataactaa catactggaa aaaacttctg 11940
ccatagactt aacagatatt gatagagcca ctgagatgat gaggaaaaac ataactttgc 12000
```

-continued

```
ttataaggat acttccattg gattgtaaca gagataaaag agagatattg agtatggaaa    12060
acctaagtat tactgaatta agcaaatatg ttagggaaag atcttggtct ttatccaata    12120
tagttggtgt tacatcaccc agtatcatgt atacaatgga catcaaatat actacaagca    12180
ctatatctag tggcataatt atagagaaat ataatgttaa cagtttaaca cgtggtgaga    12240
gaggacccac taaaccatgg gttggttcat ctacacaaga gaaaaaaaca atgccagttt    12300
ataatagaca agtcttaacc aaaaaacaga gagatcaaat agatctatta gcaaaattgg    12360
attgggtgta tgcatctata gataacaagg atgaattcat ggaagaactc agcataggaa    12420
cccttgggtt aacatatgaa aaggccaaga aattatttcc acaatattta agtgtcaatt    12480
atttgcatcg ccttacagtc agtagtagac catgtgaatt ccctgcatca ataccagctt    12540
atagaacaac aaaattatcac tttgacacta gccctattaa tcgcatatta acagaaaagt    12600
atggtgatga agatattgac atagtattcc aaaactgtat aagctttggc cttagtttaa    12660
tgtcagtagt agaacaattt actaatgtat gtcctaacag aattattctc atacctaagc    12720
ttaatgagat acatttgatg aaacctccca tattcacagg tgatgttgat attcacaagt    12780
taaaacaagt gatacaaaaa cagcatatgt ttttaccaga caaaataagt ttgactcaat    12840
atgtggaatt attcttaagt aataaaacac tcaaatctgg atctcatgtt aattctaatt    12900
taatattggc acataaaata tctgactatt ttcataatac ttacattta agtactaatt    12960 tagctggaca ttggattctg attatacaac ttatgaaaga ttctaaaggt attttttgaaa   13020 aagattgggg agagggatat ataactgatc atatgtttat taatttgaaa gttttcttca   13080
atgcttataa gacctatctc ttgtgttttc ataaaggtta tggcaaagca aagctggagt   13140
gtgatatgaa cacttcagat cttctatgtg tattggaatt aatagacagt agttattgga   13200
agtctatgtc taaggtattt ttagaacaaa aagttatcaa atacattctt agccaagatg   13260
caagtttaca tagagtaaaa ggatgtcata gcttcaaatt atggtttctt aaacgtctta   13320
atgtagcaga attcacagtt tgcccttggg ttgttaacat agattatcat ccaacacata   13380
tgaaagcaat attaacttat atagatcttg ttagaatggg attgataaat atagatagaa   13440
tacacattaa aaataaacac aaattcaatg atgaattttta tacttctaat ctcttctaca   13500
ttaattataa cttctcagat aatactcatc tattaactaa acatataagg attgctaatt   13560
ctgaattaga aaataattac aacaaattat atcatcctac accagaaacc ctagagaata   13620
tactagccaa tccgattaaa agtaatgaca aaaagacact gaatgactat tgtataggta   13680
aaaatgttga ctcaataatg ttaccattgt tatctaataa gaagcttatt aaatcgtctg   13740
caatgattag aaccaattac agcaaacaag atttgtataa tttattccct atggttgtga   13800
ttgatagaat tatagatcat tcaggcaata cagccaaatc caaccaactt tacactacta   13860
cttcccacca aatatcttta gtccacaata gcacatcact ttactgcatg cttccttggc   13920
atcatattaa tagattcaat tttgtattta gttctacagg ttgtaaaatt agtatagagt   13980
atatttaaaa agatcttaaa attaaagatc ccaattgtat agcattcata ggtgaaggag   14040
cagggaattt attattgcgt acagtagtgg aacttcatcc tgacataaga tatatttaca   14100
gaagtctgaa agattgcaat gatcatagtt tacctattga gtttttaagg ctgtacaatg   14160
gacatatcaa cattgattat ggtgaaaatt tgaccattcc tgctacagat gcaaccaaca   14220
acattcattg gtcttatttta catataaagt ttgctgaacc tatcagtctt tttgtctgtg   14280
atgccgaatt gtctgtaaca gtcaactgga gtaaaattat aatagaatgg agcaagcatg   14340
```

-continued

```
taagaaagtg caagtactgt tcctcagtta ataaatgtat gttaatagta aaatatcatg   14400
ctcaagatga tattgatttc aaattagaca atataactat attaaaaact tatgtatgct   14460
taggcagtaa gttaaaggga tcggaggttt acttagtcct tacaataggt cctgcgaata   14520
tattcccagt atttaatgta gtacaaaatg ctaaattgat actatcaaga accaaaaatt   14580
tcatcatgcc taagaaagct gataaagagt ctattgatgc aaatattaaa agtttgatac   14640
cctttctttg ttaccctata acaaaaaaag gaattaatac tgcattgtca aaactaaaga   14700
gtgttgttag tggagatata ctatcatatt ctatagctgg acgtaatgaa gttttcagca   14760
ataaacttat aaatcataag catatgaaca tcttaaaatg gttcaatcat gtttttaaatt   14820 tcagatcaac agaactaaac tataaccatt tatatatggt agaatctaca tatccttacc   14880
taagtgaatt gttaaacagc ttgacaacca atgaacttaa aaaactgatt aaaatcacag   14940
gtagtctgtt atacaacttt cataatgaat aatgaataaa gatcttataa taaaaattcc   15000
catagctata cactaacact gtattcaatt atagttatta aaaattaaaa atcatataat   15060
tttttaaata acttttagtg aactaatcct aaagttatca ttttaatctt ggaggaataa   15120
atttaaaccc taatctaatt ggtttatatg tgtattaact aaaattacgag atattagttt   15180 ttgacacttt ttttctcgt                                               15199
```

```
<210> SEQ ID NO 15
<211> LENGTH: 671
<212> TYPE: DNA
<213> ORGANISM: Artificial Sequence
<220> FEATURE:
<223> OTHER INFORMATION: GS-NlucP-GE

<400> SEQUENCE: 15
ggggcaaata aatcaatggt cttcacactc gaagatttcg ttgggggactg gcgacagaca    60 gccggctaca acctggacca agtccttgaa cagggaggtg tgtccagttt gtttcagaat   120
ctcggggtgt ccgtaactcc gatccaaagg attgtcctga gcggtgaaaa tgggctgaag   180
atcgacatcc atgtcatcat cccgtatgaa ggtctgagcg gcgaccaaat gggccagatc   240
gaaaaaattt ttaaggtggt gtaccctgtg gatgatcatc actttaaggt gatcctgcac   300
tatggcacac tggtaatcga cggggttacg ccgaacatga tcgactattt cggacggccg   360
tatgaaggca tcgccgtgtt cgacggcaaa aagatcactg taacagggac cctgtggaac   420
ggcaacaaaa ttatcgacga gcgcctgatc aaccccgacg ctccctgct gttccgagta   480 accatcaacg gagtgaccgg ctggcggctg tgcgaacgca ttctggcgaa ttctcacggc   540
tttccgcctg aggttgaaga gcaagccgcc ggtacattgc ctatgtcctg cgcacaagaa   600
agcggtatgg accggcaccc agccgcttgt gcttcagctc gcatcaacgt ctaaattata   660
gtaatttaaa a                                                       671
```

```
<210> SEQ ID NO 16
<211> LENGTH: 15
<212> TYPE: DNA
<213> ORGANISM: Artificial Sequence
<220> FEATURE:
<223> OTHER INFORMATION: RSV gene start sequence

<400> SEQUENCE: 16
ggggcaaata aatca                                                    15
```

```
<210> SEQ ID NO 17
<211> LENGTH: 17
```

```
<212> TYPE: DNA
<213> ORGANISM: Artificial Sequence
<220> FEATURE:
<223> OTHER INFORMATION: RSV gene end sequence

<400> SEQUENCE: 17
attatagtaa tttaaaa                                                             17

<210> SEQ ID NO 18
<211> LENGTH: 639
<212> TYPE: DNA
<213> ORGANISM: Artificial Sequence
<220> FEATURE:
<223> OTHER INFORMATION: NanolucP gene

<400> SEQUENCE: 18
atggtcttca cactcgaaga tttcgttggg gactggcgac agacagccgg ctacaacctg       60
gaccaagtcc ttgaacaggg aggtgtgtcc agtttgtttc agaatctcgg ggtgtccgta      120
actccgatcc aaaggattgt cctgagcggt gaaaatgggc tgaagatcga catccatgtc      180
atcatcccgt atgaaggtct gagcggcgac caaatgggcc agatcgaaaa aatttttaag      240
gtggtgtacc ctgtggatga tcatcacttt aaggtgatcc tgcactatgg cacactggta      300
atcgacgggg ttacgccgaa catgatcgac tatttcggac ggccgtatga aggcatcgcc      360
gtgttcgacg gcaaaaagat cactgtaaca gggaccctgt ggaacggcaa caaaattatc      420
gacgagcgcc tgatcaaccc cgacggctcc ctgctgttcc gagtaaccat caacggagtg      480
accggctggc ggctgtgcga acgcattctg gcgaattctc acggctttcc gcctgaggtt      540
gaagagcaag ccgccggtac attgcctatg tcctgcgcac aagaaagcgg tatggaccgg      600
cacccagccg cttgtgcttc agctcgcatc aacgtctaa                              639

<210> SEQ ID NO 19
<211> LENGTH: 57
<212> TYPE: DNA
<213> ORGANISM: Artificial Sequence
<220> FEATURE:
<223> OTHER INFORMATION: Forward primer for NanolucP

<400> SEQUENCE: 19
tatagttaca aaaaaggaa ggggcaaata aatcaatggt cttcacactc gaagatt        57

<210> SEQ ID NO 20
<211> LENGTH: 57
<212> TYPE: DNA
<213> ORGANISM: Artificial Sequence
<220> FEATURE:
<223> OTHER INFORMATION: Reverse primer for NanolucP

<400> SEQUENCE: 20
ttccatattt gccccaccct ttttaaatta ctataattta gacgttgatg cgagctg        57

<210> SEQ ID NO 21
<211> LENGTH: 23708
<212> TYPE: DNA
<213> ORGANISM: Artificial Sequence
<220> FEATURE:
<223> OTHER INFORMATION: pSMART RS A2 NLucP

<400> SEQUENCE: 21
ggcgcgccta atacgactca ctatagggac gggaaaaaat gcgtacaaca aacttgcata       60
aaccaaaaaa atggggcaaa taagaatttg ataagtacca cttaaattta actcccttgg      120
```

-continued

```
ttagagatgg gcagcaattc attgagtatg ataaaagtta gattacaaaa tttgtttgac      180
aatgatgaag tagcattgtt aaaaataaca tgctatactg ataaattaat acatttaact      240
aacgctttgg ctaaggcagt gatacataca atcaaattga atggcattgt gtttgtgcat      300
gttattacaa gtagtgatat ttgccctaat aataatattg tagtaaaatc caatttcaca      360
acaatgccag tactacaaaa tggaggttat atatgggaaa tgatggaatt aacacattgc      420
tctcaaccta atggtctact agatgacaat tgtgaaatta aattctccaa aaaactaagt      480
gattcaacaa tgaccaatta tatgaatcaa ttatctgaat tacttggatt tgatcttaat      540
ccataaatta taattaatat caactagcaa atcaatgtca ctaacaccat tagttaatat      600
aaaacttaac agaagacaaa aatggggcaa ataaatcaat tcagccaacc caaccatgga      660
cacaacccac aatgataata caccacaaag actgatgatc acagacatga gaccgttgtc      720
acttgagacc ataataacat cactaaccag agacatcata acacacaaat ttatatactt      780
gataaatcat gaatgcatag tgagaaaact tgatgaaaaa caggccacat ttacattcct      840
ggtcaactat gaaatgaaac tattacacaa agtaggaagc actaaatata aaaaatatac      900
tgaatacaac acaaaaatatg gcactttccc tatgccaata ttcatcaatc atgatgggtt      960
cttagaatgc attggcatta agcctacaaa gcatactccc ataatataca agtatgatct     1020
caatccataa atttcaacac aatattcaca caatctaaaa caacaactct atgcataact     1080
atactccata gtccagatgg agcctgaaaa ttatagtaat ttaaaattaa ggagagatat     1140
aagatagaag atggggcaaa tacaaagatg gctcttagca aagtcaagtt gaatgataca     1200
ctcaacaaag atcaacttct gtcatccagc aaatacacca tccaacggag cacaggagat     1260
agtattgata ctcctaatta tgatgtgcag aaacacatca ataagttatg tggcatgtta     1320
ttaatcacag aagatgctaa tcataaattc actgggttaa taggtatgtt atatgcgatg     1380
tctaggttag gaagagaaga caccataaaa atactcagag atgcgggata tcatgtaaaa     1440
gcaaatggag tagatgtaac aacacatcgt caagacatta atggaaaaga aatgaaattt     1500
gaagtgttaa cattggcaag cttaacaact gaaattcaaa tcaacattga gatagaatct     1560
agaaaatcct acaaaaaaat gctaaaagaa atgggagagg tagctccaga atacaggcat     1620
gactctcctg attgtgggat gataatatta tgtatagcag cattagtaat aactaaatta     1680
gcagcagggg acagatctgg tcttacagcc gtgattagga gagctaataa tgtcctaaaa     1740
aatgaaatga aacgttacaa aggcttacta cccaaggaca tagccaacag cttctatgaa     1800
gtgtttgaaa aacatcccca ctttatagat gtttttgttc attttggtat agcacaatct     1860
tctaccagag gtggcagtag agttgaaggg attttttgcag gattgtttat gaatgcctat     1920
ggtgcagggc aagtgatgtt acggtgggga gtcttagcaa aatcagttaa aaatattatg     1980
ttaggacatg ctagtgtgca agcagaaatg gaacaagttg ttgaggttta tgaatatgcc     2040
caaaaattgg gtggtgaagc aggattctac catatattga caacccaaa agcatcatta     2100 ttatctttga ctcaatttcc tcacttctcc agtgtagtat taggcaatgc tgctggccta     2160
ggcataatgg gagagtacag aggtacaccg aggaatcaag atctatatga tgcagcaaag     2220
gcatatgctg aacaactcaa agaaaatggt gtgattaact acagtgtact agacttgaca     2280
gcagaagaac tagaggctat caaacatcag cttaatccaa aagataatga tgtagagctt     2340
tgagttaata aaaaatgggg caaataaatc atcatggaaa agtttgctcc tgaattccat     2400
ggagaagatg caaacaacag ggctactaaa ttcctagaat caataaaggg caaattcaca     2460
tcacccaaag atcccaagaa aaaagatagt atcatatctg tcaactcaat agatatagaa     2520
```

-continued

```
gtaaccaaag aaagccctat aacatcaaat tcaactatta tcaacccaac aaatgagaca   2580
gatgatactg cagggaacaa gcccaattat caaagaaaac ctctagtaag tttcaaagaa   2640
gaccctacac caagtgataa tcccttttct aaactataca aagaaaccat agaaacattt   2700
gataacaatg aagaagaatc cagctattca tacgaagaaa taaatgatca gacaaacgat   2760
aatataacag caagattaga taggattgat gaaaaattaa gtgaaatact aggaatgctt   2820
cacacattag tagtggcaag tgcaggacct acatctgctc gggatggtat aagagatgcc   2880
atgattggtt taagagaaga aatgatagaa aaaatcagaa ctgaagcatt aatgaccaat   2940
gacagattag aagctatggc aagactcagg aatgaggaaa gtgaaaagat ggcaaaagac   3000
acatcagatg aagtgtctct caatccaaca tcagagaaat tgaacaacct attggaaggg   3060
aatgatagtg acaatgatct atcacttgaa gatttctgat tagttaccac tcttcacatc   3120
aacacacaat accaacagaa gaccaacaaa ctaaccaacc caatcatcca accaaacatc   3180
catccgccaa tcagccaaac agccaacaaa acaaccagcc aatccaaaac taaccacccg   3240
gaaaaaatct ataatatagt tacaaaaaaa ggaaggggca aataaatcaa tggtcttcac   3300
actcgaagat ttcgttgggg actggcgaca gacagccggc tacaacctgg accaagtcct   3360
tgaacaggga ggtgtgtcca gtttgtttca gaatctcggg gtgtccgtaa ctccgatcca   3420
aaggattgtc ctgagcggtg aaaatgggct gaagatcgac atccatgtca tcatcccgta   3480
tgaaggtctg agcggcgacc aaatgggcca gatcgaaaaa atttttaagg tggtgtaccc   3540
tgtggatgat catcacttta aggtgatcct gcactatggc acactggtaa tcgacgcgggt   3600 tacgccgaac atgatcgact atttcggacg gccgtatgaa ggcatcgccg tgttcgacgg   3660
caaaaagatc actgtaacag ggaccctgtg gaacggcaac aaaattatcg acgagcgcct   3720
gatcaacccc gacggctccc tgctgttccg agtaaccatc aacggagtga ccggctggcg   3780
gctgtgcgaa cgcattctgg cgaattctca cggctttccg cctgaggttg aagagcaagc   3840
cgccggtaca ttgcctatgt cctgcgcaca agaaagcggt atggaccggc acccagccgc   3900
ttgtgcttca gctcgcatca acgtctaaat tatagtaatt taaaaagggt ggggcaaata   3960
tggaaacata cgtgaacaag cttcacgaag gctccacata cacagctgct gttcaataca   4020
atgtcttaga aaaagacgat gaccctgcat cacttacaat atgggtgccc atgttccaat   4080
catctatgcc agcagattta cttataaaag aactagctaa tgtcaacata ctagtgaaac   4140
aaatatccac acccaaggga ccttcactaa gagtcatgat aaactcaaga agtgcagtgc   4200
tagcacaaat gcccagcaaa tttaccatat gcgctaatgt gtccttggat gaaagaagca   4260
aactagcata tgatgtaacc acaccctgtg aaatcaaggc atgtagtcta acatgcctaa   4320
aatcaaaaaa tatgttgact acagttaaag atctcactat gaagacactc aaccctacac   4380
atgatattat tgctttatgt gaatttgaaa acatagtaac atcaaaaaaa gtcataatac   4440
caacatacct aagatccatc agtgtcagaa ataaagatct gaacacactt gaaaatataa   4500
caaccactga attcaaaaat gctatcacaa atgcaaaaat catcccttac tcaggattac   4560
tattagtcat cacagtgact gacaacaaag gagcattcaa atacataaag ccacaaagtc   4620
aattcatagt agatcttgga gcttacctag aaaaagaaag tatatattat gttaccacaa   4680
attggaagca cacagctaca cgatttgcaa tcaaacccat ggaagattaa ccttttttcct   4740 ctacatcagt gtgttaattc atacaaactt tctacctaca ttcttcactt caccatcaca   4800
atcacaaaca ctctgtggtt caaccaatca aacaaaactt atctgaagtc ccagatcatc   4860
```

-continued

```
ccaagtcatt gtttatcaga tctagtactc aaataagtta ataaaaaata tacacatggg       4920
gcaaataatc attggaggaa atccaactaa tcacaatatc tgttaacata gacaagtcca       4980
cacaccatac agaatcaacc aatggaaaat acatccataa caatagaatt ctcaagcaaa       5040 ttctggccctt actttacact aatacacatg atcacaacaa taatctcttt gctaatcata      5100
atctccatca tgattgcaat actaaacaaa ctttgtgaat ataacgtatt ccataacaaa       5160
acctttgagt taccaagagc tcgagtcaac acatagcatt catcaatcca acagcccaaa       5220
acagtaacct tgcatttaaa aatgaacaac ccctacctct ttacaacacc tcattaacat       5280
cccaccatgc aaaccactat ccatactata aagtagttaa ttaaaaatag tcataacaat       5340
gaactaggat atcaagacta acaataacat tggggcaaat gcaaacatgt ccaaaaacaa       5400
ggaccaacgc accgctaaga cattagaaag gacctgggac actctcaatc atttattatt       5460
catatcatcg tgcttatata agttaaatct taaatctgta gcacaaatca cattatccat       5520
tctggcaatg ataatctcaa cttcacttat aattgcagcc atcatattca tagcctcggc       5580
aaaccacaaa gtcacaccaa caactgcaat catacaagat gcaacaagcc agatcaagaa       5640
cacaacccca acatacctca cccagaatcc tcagcttgga atcagtccct ctaatccgtc       5700
tgaaattaca tcacaaatca ccaccatact agcttcaaca acaccaggag tcaagtcaac       5760
cctgcaatcc acaacagtca agaccaaaaa cacaacaaca actcaaacac aacccagcaa       5820
gcccaccaca aaacaacgcc aaaacaaacc accaagcaaa cccaataatg attttcactt       5880
tgaagtgttc aactttgtac cctgcagcat atgcagcaac aatccaacct gctgggctat       5940
ctgcaaaaga ataccaaaca aaaaaccagg aaagaaaacc actaccaagc ccacaaaaaa       6000
accaaccctc aagacaacca aaaaagatcc caaacctcaa accactaaat caaaggaagt       6060
acccaccacc aagcccacag aagagccaac catcaacacc accaaaacaa acatcataac       6120
tacactactc acctccaaca ccacaggaaa tccagaactc acaagtcaaa tggaaacctt       6180
ccactcaact tcctccgaag gcaatccaag cccttctcaa gtctctacaa catccgagta       6240
cccatcacaa ccttcatctc cacccaacac accacgccag tagttactta aaaacatatt       6300
atcacaaaaa gccatgacca acttaaacag aatcaaaata aactctgggg caaataacaa       6360
tggagttgct aatcctcaaa gcaaatgcaa ttaccacaat cctcactgca gtcacatttt       6420
gttttgcttc tggtcaaaac atcactgaag aattttatca atcaacatgc agtgcagtta       6480
gcaaaggcta tcttagtgct ctgagaactg gttggtatac cagtgttata actatagaat       6540
taagtaatat caaggaaaat aagtgtaatg gaacagatgc taaggtaaaa ttgataaaac       6600
aagaattaga taaatataaa aatgctgtaa cagaattgca gttgctcatg caaagcacac       6660
caccaacaaa caatcgagcc agaagagaac taccaaggtt tatgaattat acactcaaca       6720
atgccaaaaa aaccaatgta acattaagca agaaaaggaa aagaagattt cttgttttttt     6780 tgttaggtgt tggatctgca atcgccagtg gcgttgctgt atctaaggtc ctgcacctag       6840 aagggaagt gaacaagatc aaaagtgctc tactatccac aaacaaggct ctagtcagct        6900
tatcaaatgg agttagtgtc ttaaccagca aagtgttaga cctcaaaaac tatatagata       6960
aacaattgtt acctattgtg aacaagcaaa gctgcagcat atcaaatata gaaactgtga       7020
tagagttcca acaaaagaac aacagactac tagagattac cagggaattt agtgttaatg       7080
caggtgtaac tacacctgta agcacttaca tgttaactaa tagtgaatta ttgtcattaa       7140
tcaatgatat gcctataaca aatgatcaga aaaagttaat gtccaacaat gttcaaatag       7200
ttagacagca aagttactct atcatgtcca taataaaaga ggaagtctta gcatatgtag       7260
```

-continued

```
tacaattacc actatatggt gttatagata caccctgttg gaaactacac acatcccctc    7320
tatgtacaac caacacaaaa gaagggtcca acatctgttt aacaagaact gacagaggat    7380
ggtactgtga caatgcagga tcagtatctt tcttcccaca agctgaaaca tgtaaagttc    7440
aatcaaatcg agtattttgt gacacaatga acagtttaac attaccaagt gaaataaatc    7500
tctgcaatgt tgacatattc aaccccaaat atgattgtaa aattatgact tcaaaaacag    7560
atgtaagcag ctccgttatc acatctctag gagccattgt gtcatgctat ggcaaaacta    7620
aatgtacagc atccaataaa aatcgtggaa tcataaagac attttctaac gggtgcgatt    7680
atgtatcaaa taaagggatg gacactgtgt ctgtaggtaa cacattatat tatgtaaata    7740
agcaagaagg taaaagtctc tatgtaaaag gtgaaccaat aataaatttc tatgacccat    7800
tagtattccc ctctgatgaa tttgatgcat caatatctca agtcaacgag aagattaacc    7860
agagcctagc atttattcgt aaatccgatg aattattaca taatgtaaat gctggtaaat    7920
ccaccacaaa tatcatgata actactataa ttatagtgat tatagtaata ttgttatcat    7980
taattgctgt tggactgctc ttatactgta aggccagaag cacaccagtc acactaagca    8040
aagatcaact gagtggtata aataatattg catttagtaa ctaaataaaa atagcaccta    8100
atcatgttct tacaatggtt tactatctgc tcatagacaa cccatctgtc attggatttt    8160
cttaaaatct gaacttcatc gaaactctca tctataaacc atctcactta cactatttaa    8220
gtagattcct agtttatagt tatataaaac acaattgaat gccagattaa cttaccatct    8280
gtaaaaatga aaactggggc aaatatgtca cgaaggaatc cttgcaaatt tgaaattcga    8340
ggtcattgct taaatggtaa gaggtgtcat tttagtcata attattttga atggccaccc    8400
catgcactgc ttgtaagaca aaactttatg ttaaacagaa tacttaagtc tatggataaa    8460
agtatagata ccttatcaga aataagtgga gctgcagagt tggacagaac agaagagtat    8520
gctcttggtg tagttggagt gctagagagt tatataggat caataaacaa tataactaaa    8580
caatcagcat gtgttgccat gagcaaactc ctcactgaac tcaatagtga tgatatcaaa    8640
aagctgaggg acaatgaaga gctaaattca cccaagataa gagtgtacaa tactgtcata    8700
tcatatattg aaagcaacag gaaaaacaat aaacaaacta tccatctgtt aaaaagattg    8760
ccagcagacg tattgaagaa aaccatcaaa aacacattgg atatccataa gagcataacc    8820
atcaacaacc caaagaatc aactgttagt gatacaaatg accatgccaa aaataatgat    8880
actacctgac aaatatcctt gtagtataac ttccatacta ataacaagta gatgtagagt    8940
tactatgtat aatcaaaaga acacactata tttcaatcaa aacaacccaa ataaccatat    9000
gtactcaccg aatcaaacat tcaatgaaat ccattggacc tctcaagaat tgattgacac    9060
aattcaaatt tttctacaac atctaggtat tattgaggat atatacaa tatatatatt    9120 agtgtcataa cactcaattc taacactcac cacatcgtta cattattaat tcaaacaatt    9180
caagttgtgg gacaaaatgg atcccattat taatggaaat tctgctaatg tttatctaac    9240
cgatagttat ttaaaaggtg ttatctcttt ctcagagtgt aatgctttag gaagttacat    9300
attcaatggt cccttatctca aaaatgatta taccaactta attagtagac aaaatccatt    9360
aatagaacac atgaatctaa agaaactaaa tataacacag tccttaatat ctaagtatca    9420
taaaggtgaa ataaaattag aagaacctac ttattttcag tcattactta tgacatacaa    9480
gagtatgacc tcgtcagaac agattgctac cactaatttta cttaaaaaga taataagaag    9540
agctatagaa ataagtgatg tcaaagtcta tgctatattg aataaactag ggcttaaaga    9600
```

-continued

```
aaaggacaag attaaatcca acaatggaca agatgaagac aactcagtta ttacgaccat    9660
aatcaaagat gatatacttt cagctgttaa agataatcaa tctcatctta aagcagacaa    9720
aaatcactct acaaaacaaa aagacacaat caaaacaaca ctcttgaaga aattgatgtg    9780
ttcaatgcaa catcctccat catggttaat acattggttt aacttataca caaaattaaa    9840
caacatatta acacagtatc gatcaaatga ggtaaaaaac catgggttta cattgataga    9900
taatcaaact cttagtggat ttcaatttat tttgaaccaa tatggttgta tagtttatca    9960
taaggaactc aaaagaatta ctgtgacaac ctataatcaa ttcttgacat ggaaagatat   10020
tagccttagt agattaaatg tttgtttaat tacatggatt agtaactgct tgaacacatt   10080
aaataaaagc ttaggcttaa gatgcggatt caataatgtt atcttgacac aactattcct   10140
ttatggagat tgtatactaa agctatttca caatgagggg ttctacataa taaaagaggt   10200
agagggattt attatgtctc taattttaaa tataacagaa gaagatcaat tcagaaaacg   10260
attttataat agtatgctca acaacatcac agatgctgct aataaagctc agaaaaatct   10320
gctatcaaga gtatgtcata cattattaga taagacagtg tccgataata taataaatgg   10380
cagatggata attctattaa gtaagttcct taaattaatt aagcttgcag gtgacaataa   10440
ccttaacaat ctgagtgaac tatatttttt gttcagaata tttggacacc caatggtaga   10500
tgaaagacaa gccatggatg ctgttaaaat taattgcaat gagaccaaat tttacttgtt   10560
aagcagtctg agtatgttaa gaggtgcctt tatatataga attataaaag ggtttgtaaa   10620
taattacaac agatggccta ctttaagaaa tgctattgtt ttacccttaa gatggttaac   10680
ttactataaa ctaaacactt atccttcttt gttggaactt acagaaagag atttgattgt   10740
gttatcagga ctacgtttct atcgtgagtt tcggttgcct aaaaaagtgg atcttgaaat   10800
gattataaat gataaagcta tatcacctcc taaaaatttg atatggacta gtttccctag   10860
aaattacatg ccatcacaca tacaaaacta tatagaacat gaaaaattaa aattttccga   10920
gagtgataaa tcaagaagag tattagagta ttatttaaga gataacaaat tcaatgaatg   10980
tgatttatac aactgtgtag ttaatcaaag ttatctcaac aaccctaatc atgtggtatc   11040
attgacaggc aaagaaagag aactcagtgt aggtagaatg tttgcaatgc aaccgggaat   11100
gttcagacag gttcaaatat tggcagagaa aatgatagct gaaaacattt tacaattctt   11160
tcctgaaagt cttacaagat atggtgatct agaactacaa aaaatattag aattgaaagc   11220
aggaataagt aacaaatcaa atcgctacaa tgataattac aacaattaca ttagtaagtg   11280
ctctatcatc acagatctca gcaaattcaa tcaagcattt cgatatgaaa cgtcatgtat   11340
ttgtagtgat gtgctggatg aactgcatgg tgtacaatct ctattttcct ggttacattt   11400
aactattcct catgtcacaa taatatgcac atataggcat gcacccccct atataggaga   11460
tcatattgta gatcttaaca atgtagatga acaaagtgga ttatatagat atcacatggg   11520
tggcatcgaa gggtggtgtc aaaaactgtg gaccatagaa gctatatcac tattggatct   11580
aatatctctc aaagggaaat tctcaattac tgctttaatt aatggtgaca atcaatcaat   11640
agatataagc aaaccaatca gactcatgga aggtcaaact catgctcaag cagattattt   11700
gctagcatta aatagcctta aattactgta taaagagtat gcaggcatag gccacaaatt   11760
aaaaggaact gagacttata tatcacgaga tatgcaattt atgagtaaaa caattcaaca   11820
taacggtgta tattacccag ctagtataaa gaaagtccta agagtgggac cgtggataaa   11880
cactatactt gatgatttca aagtgagtct agaatctata ggtagtttga cacaagaatt   11940
agaatataga ggtgaaagtc tattatgcag tttaatattt agaaatgtat ggttatataa   12000
```

-continued

```
tcagattgct ctacaattaa aaaatcatgc attatgtaac aataaactat atttggacat   12060
attaaaggtt ctgaaacact taaaaacctt ttttaatctt gataatattg atacagcatt   12120
aacattgtat atgaatttac ccatgttatt tggtggtggt gatcccaact tgttatatcg   12180
aagtttctat agaagaactc ctgacttcct cacagaggct atagttcact ctgtgttcat   12240
acttagttat tatacaaacc atgacttaaa agataaactt caagatctgt cagatgatag   12300
attgaataag ttcttaacat gcataatcac gtttgacaaa aaccctaatg ctgaattcgt   12360
aacattgatg agagatcctc aagctttagg gtctgagaga caagctaaaa ttactagcga   12420
aatcaataga ctggcagtta cagaggtttt gagtacagct ccaaacaaaa tattctccaa   12480
aagtgcacaa cattatacta ctacagagat agatctaaat gatattatgc aaaatataga   12540
acctacatat cctcatgggc taagagttgt ttatgaaagt ttacccttt ataaagcaga    12600 gaaaatagta aatcttatat caggtacaaa atctataact aacatactgg aaaaaacttc   12660
tgccatagac ttaacagata ttgatagagc cactgagatg atgaggaaaa acataacttt   12720
gcttataagg atacttccat tggattgtaa cagagataaa agagagatat tgagtatgga   12780
aaacctaagt attactgaat taagcaaata tgttagggaa agatcttggt ctttatccaa   12840
tatagttggt gttacatcac ccagtatcat gtatacaatg gacatcaaat atactacaag   12900
cactatatct agtggcataa ttatagagaa atataatgtt aacagtttaa cacgtggtga   12960
gagaggaccc actaaaccat gggttggttc atctacacaa gagaaaaaaa caatgccagt   13020
ttataataga caagtcttaa ccaaaaaaca gagagatcaa atagatctat tagcaaaatt   13080
ggattgggtg tatgcatcta tagataacaa ggatgaattc atggaagaac tcagcatagg   13140
aacccttggg ttaacatatg aaaaggccaa gaaattattt ccacaatatt taagtgtcaa   13200
ttatttgcat cgccttacag tcagtagtag accatgtgaa ttccctgcat caataccagc   13260
ttatagaaca acaaattatc actttgacac tagccctatt aatcgcatat taacagaaaa   13320
gtatggtgat gaagatattg acatagtatt ccaaaactgt ataagctttg gccttagttt   13380
aatgtcagta gtagaacaat ttactaatgt atgtcctaac agaattattc tcatacctaa   13440
gcttaatgag atacatttga tgaaacctcc catattcaca ggtgatgttg atattcacaa   13500
gttaaaacaa gtgatacaaa aacagcatat gttttttacca gacaaaataa gtttgactca   13560
atatgtggaa ttattcttaa gtaataaaac actcaaatct ggatctcatg ttaattctaa   13620
tttaatattg gcacataaaa tatctgacta ttttcataat acttacattt taagtactaa   13680
tttagctgga cattggattc tgattataca acttatgaaa gattctaaag gtatttttga   13740
aaaagattgg ggagagggat atataactga tcatatgttt attaatttga aagttttctt   13800
caatgcttat aagacctatc tcttgtgttt tcataaaggt tatggcaaag caaagctgga   13860
gtgtgatatg aacacttcag atcttctatg tgtattggaa ttaatagaca gtagttattg   13920
gaagtctatg tctaaggtat ttttagaaca aaaagttatc aaatacattc ttagccaaga   13980
tgcaagttta catagagtaa aaggatgtca tagcttcaaa ttatggtttc ttaaacgtct   14040
taatgtagca gaattcacag tttgcccttg ggttgttaac atagattatc atccaacaca   14100
tatgaaagca atattaactt atatagatct tgttagaatg ggattgataa atatagatag   14160
aatacacatt aaaaataaac acaaattcaa tgatgaattt tatacttcta atctcttcta   14220
cattaattat aacttctcag ataatactca tctattaact aaacatataa ggattgctaa   14280
ttctgaatta gaaaataatt acaacaaatt atatcatcct acaccagaaa ccctagagaa   14340
```

-continued

```
tatactagcc aatccgatta aaagtaatga caaaaagaca ctgaatgact attgtatagg   14400
taaaaatgtt gactcaataa tgttaccatt gttatctaat aagaagctta ttaaatcgtc   14460
tgcaatgatt agaaccaatt acagcaaaca agatttgtat aatttattcc ctatggttgt   14520
gattgataga attatagatc attcaggcaa tacagccaaa tccaaccaac tttacactac   14580
tacttcccac caaatatctt tagtccacaa tagcacatca ctttactgca tgcttccttg   14640
gcatcatatt aatagattca attttgtatt tagttctaca ggttgtaaaa ttagtataga   14700
gtatatttta aaagatctta aaattaaaga tcccaattgt atagcattca taggtgaagg   14760
agcagggaat ttattattgc gtacagtagt ggaacttcat cctgacataa gatatattta   14820
cagaagtctg aaagattgca atgatcatag tttacctatt gagtttttaa ggctgtacaa   14880
tggacatatc aacattgatt atggtgaaaa tttgaccatt cctgctacag atgcaaccaa   14940
caacattcat tggtcttatt tacatataaa gtttgctgaa cctatcagtc tttttgtctg   15000
tgatgccgaa ttgtctgtaa cagtcaactg gagtaaaatt ataatagaat ggagcaagca   15060
tgtaagaaag tgcaagtact gttcctcagt taataaatgt atgttaatag taaaatatca   15120
tgctcaagat gatattgatt tcaaattaga caatataact atattaaaaa cttatgtatg   15180
cttaggcagt aagttaaagg gatcggaggt ttacttagtc cttacaatag gtcctgcgaa   15240
tatattccca gtatttaatg tagtacaaaa tgctaaattg atactatcaa gaaccaaaaa   15300
tttcatcatg cctaagaaag ctgataaaga gtctattgat gcaaatatta aaagtttgat   15360 acccttttctt tgttaccccta taacaaaaaa aggaattaat actgcattgt caaaactaaa   15420
gagtgttgtt agtggagata tactatcata ttctatagct ggacgtaatg aagtttttcag   15480 caataaactt ataaatcata agcatatgaa catcttaaaa tggttcaatc atgtttttaaa   15540 tttcagatca acagaactaa actataacca tttatatatg gtagaatcta catatcctta   15600
cctaagtgaa ttgttaaaca gcttgacaac caatgaactt aaaaaactga ttaaaatcac   15660
aggtagtctg ttatacaact ttcataatga ataatgaata aagatcttat aataaaaatt   15720
cccatagcta tacactaaca ctgtattcaa ttatagttat taaaaattaa aaatcatata   15780
attttttaaa taacttttag tgaactaatc ctaaagttat cattttaatc ttggaggaat   15840
aaatttaaac cctaatctaa ttggtttata tgtgtattaa ctaaattacg agatattagt   15900
ttttgacact ttttttctcg tgggtcggca tggcatctcc acctcctcgc ggtccgacct   15960
gggcatccga aggaggacgc acgtccactc ggatggctaa gggagagcct gcagtagcat   16020
aaccccttgg ggcctctaaa cgggtcttga ggggtttttt ggtgaaagga ggaactatag   16080
gccggcccac cgcatatgtc tcagtacaat ctgctctgat gccgcatagc catcacattg   16140
tacacgtgga caagttgtcg cggccgcttc tatagtgtca cctaaatact agtgactcca   16200
gcgtaactgg actggccaca gttaggccgc aaatgtaatc acactggctc accttcgggt   16260
gggcctttct gcgttcgcga gtggacccga taagctcatg gagcggcgta accgtcgcac   16320
aggaaggaca gagaaagcgc ggatctggga agtgacggac agaacggtca ggacctggat   16380
tggggaggcg gttgccgccg ctgctgctga cggtgtgacg ttctctgttc cggtcacacc   16440
acatacgttc cgccattcct atgcgatgca catgctgtat gccggtatac cgctgaaagt   16500
tctgcaaagc ctgatgggac ataagtccat cagttcaacg gaagtctaca cgaaggtttt   16560
tgcgctggat gtggctgccc ggcaccgggt gcagtttgcg atgccggagt ctgatgcggt   16620
tgcgatgctg aaacaattat cctgagaata aatgccttgg cctttatatg gaaatgtgga   16680
actgagtgga tatgctgttt ttgtctgtta aacagagaag ctggctgtta ccactgaga   16740
```

-continued

```
agcgaacgaa acagtcggga aaatctccca ttatcgtaga gatccgcatt attaatctca   16800
ggagcctgtg tagcgtttat aggaagtagt gttctgtcat gatgcctgca agcggtaacg   16860
aaaacgattt gaatatgcct tcaggaacaa tagaaatctt cgtgcggtgt tacgttgaag   16920
tggagcggat tatgtcagca atggacagaa caacctaatg aacacagaac catgatgtgg   16980
tctgtccttt tacagccagt agtgctcgcc gcagtcgagc gacagggcga agccctcggc   17040
tggttgccct cgccgctggg ctggcggccg tctatggccc tgcaaacgcg ccagaaacgc   17100
cgtcgaagcc gtgtgcgaga caccgcggcc ggccgccggc gttgtggata cctcgcggaa   17160
aacttggccc tcactgacag atgaggggcg gacgttgaca cttgaggggc cgactcaccc   17220
ggcgcggcgt tgacagatga ggggcaggct cgatttcggc cggcgacgtg gagctggcca   17280
gcctcgcaaa tcggcgaaaa cgcctgattt tacgcgagtt tcccacagat gatgtggaca   17340
agcctgggga taagtgccct gcggtattga cacttgaggg gcgcgactac tgacagatga   17400
ggggcgcgat ccttgacact tgaggggcag agtgctgaca gatgaggggc gcacctattg   17460
acatttgagg ggctgtccac aggcagaaaa tccagcattt gcaagggttt ccgcccgttt   17520
ttcggccacc gctaacctgt cttttaacct gcttttaaac caatatttat aaaccttgtt   17580
tttaaccagg gctgcgccct gtgcgcgtga ccgcgcacgc cgaagggggg tgcccccct   17640 tctcgaaccc tcccggtcga gtgagcgagg aagcaccagg gaacagcact tatatattct   17700
gcttacacac gatgcctgaa aaaacttccc ttggggttat ccacttatcc acggggatat   17760
ttttataatt attttttta tagttttag atcttctttt ttagagcgcc ttgtaggcct   17820
ttatccatgc tggttctaga gaaggtgttg tgacaaattg cccttttcagt gtgacaaatc   17880 accctcaaat gacagtcctg tctgtgacaa attgccctta accctgtgac aaattgccct   17940
cagaagaagc tgtttttttca caaagttatc cctgcttatt gactcttttt tatttagtgt   18000
gacaatctaa aaacttgtca cacttcacat ggatctgtca tggcggaaac agcggttatc   18060
aatcacaaga aacgtaaaaa tagcccgcga atcgtccagt caaacgacct cactgaggcg   18120
gcatatagtc tctcccggga tcaaaaacgt atgctgtatc tgttcgttga ccagatcaga   18180
aaatctgatg gcaccctaca ggaacatgac ggtatctgcg agatccatgt tgctaaatat   18240
gctgaaatat tcggattgac ctctgcggaa gccagtaagg atatacggca ggcattgaag   18300
agtttcgcgg ggaaggaagt ggtttttttat cgccctgaag aggatgccgg cgatgaaaaa   18360
ggctatgaat cttttccttg gtttatcaaa cgtgcgcaca gtccatccag agggctttac   18420
agtgtacata tcaacccata tctcattccc ttctttatcg ggttacagaa ccggtttacg   18480
cagtttcggc ttagtgaaac aaaagaaatc accaatccgt atgccatgcg tttatacgaa   18540
tccctgtgtc agtatcgtaa gccggatggc tcaggcatcg tctctctgaa aatcgactgg   18600
atcatagagc gttaccagct gcctcaaagt taccagcgta tgcctgactt ccgccgccgc   18660
ttcctgcagg tctgtgttaa tgagatcaac agcagaactc caatgcgcct ctcatacatt   18720
gagaaaaaga aaggccgcca gacgactcat atcgtatttt ccttccgcga tatcacttcc   18780
atgacgacag gatagtctga gggttatctg tcacagattt gagggtggtt cgtcacattt   18840
gttctgacct actgagggta atttgtcaca gttttgctgt ttccttcagc ctgcatggat   18900
tttctcatac tttttgaact gtaatttta aggaagccaa atttgagggc agtttgtcac   18960
agttgatttc cttctctttc ccttcgtcat gtgacctgat atcgggggtt agttcgtcat   19020
cattgatgag ggttgattat cacagtttat tactctgaat tggctatccg cgtgtgtacc   19080
```

-continued

```
tctacctgga gttttttccca cggtggatat ttcttcttgc gctgagcgta agagctatct   19140
gacagaacag ttcttctttg cttcctcgcc agttcgctcg ctatgctcgg ttacacggct   19200
gcggcgagcg ctagtgataa taagtgactg aggtatgtgc tcttcttatc tccttttgta   19260
gtgttgctct tattttaaac aactttgcgg ttttttgatg actttgcgat tttgttgttg   19320
ctttgcagta aattgcaaga tttaataaaa aaacgcaaag caatgattaa aggatgttca   19380
gaatgaaact catggaaaca cttaaccagt gcataaacgc tggtcatgaa atgacgaagg   19440
ctatcgccat tgcacagttt aatgatgaca gcccggaagc gaggaaaata acccggcgct   19500
ggagaatagg tgaagcagcg gatttagttg gggtttcttc tcaggctatc agagatgccg   19560
agaaagcagg gcgactaccg caccggata tggaaattcg aggacgggtt gagcaacgtg   19620
ttggttatac aattgaacaa attaatcata tgcgtgatgt gtttggtacg cgattgcgac   19680
gtgctgaaga cgtatttcca ccggtgatcg gggttgctgc ccataaagga ggcgtttaca   19740
aaacctcagt ttctgttcat cttgctcagg atctggctct gaaggggcta cgtgttttgc   19800
tcgtggaagg taacgacccc cagggaacag cctcaatgta tcacggatgg gtaccagatc   19860
ttcatattca tgcagaagac actctcctgc ctttctatct tggggaaaag gacgatgtca   19920
cttatgcaat aaagcccact tgctggccgg ggcttgacat tattccttcc tgtctggctc   19980
tgcaccgtat tgaaactgag ttaatgggca aatttgatga aggtaaactg cccaccgatc   20040
cacacctgat gctccgactg gccattgaaa ctgttgctca tgactatgat gtcatagtta   20100
ttgacagcgc gcctaacctg ggtatcggca cgattaatgt cgtatgtgct gctgatgtgc   20160
tgattgttcc cacgcctgct gagttgtttg actacacctc cgcactgcag tttttcgata   20220
tgcttcgtga tctgctcaag aacgttgatc ttaaagggtt cgagcctgat gtacgtattt   20280
tgcttaccaa atacagcaat agtaatggct ctcagtcccc gtggatggag gagcaaattc   20340
gggatgcctg gggaagcatg gttctaaaaa atgttgtacg tgaaacggat gaagttggta   20400
aaggtcagat ccggatgaga actgtttttg aacaggccat tgatcaacgc tcttcaactg   20460
gtgcctggag aaatgctctt tctatttggg aacctgtctg caatgaaatt ttcgatcgtc   20520
tgattaaacc acgctgggag attagataat gaagcgtgcg cctgttattc caaaacatac   20580
gctcaatact caaccggttg aagatacttc gttatcgaca ccagctgccc cgatggtgga   20640
ttcgttaatt gcgcgcgtag gagtaatggc tcgcggtaat gccattactt tgcctgtatg   20700
tggtcgggat gtgaagttta ctcttgaagt gctccggggt gatagtgttg agaagacctc   20760
tcgggtatgg tcaggtaatg aacgtgacca ggagctgctt actgaggacg cactggatga   20820
tctcatccct tcttttctac tgactggtca acagacaccg gcgttcggtc gaagagtatc   20880
tggtgtcata gaaattgccg atgggagtcg ccgtcgtaaa gctgctgcac ttaccgaaag   20940
tgattatcgt gttctggttg gcgagctgga tgatgagcag atggctgcat tatccagatt   21000
gggtaacgat tatcgcccaa caagtgctta tgaacgtggt cagcgttatg caagccgatt   21060
gcagaatgaa tttgctggaa atatttctgc gctggctgat gcggaaaata tttcacgtaa   21120
gattattacc cgctgtatca acaccgccaa attgcctaaa tcagttgttg ctcttttttc   21180
tcaccccggt gaactatctg cccggtcagg tgatgcactc caaaaagcct ttacagataa   21240
agaggaatta cttaagcagc aggcatctaa ccttcatgag cagaaaaaag ctggggtgat   21300
atttgaagct gaagaagtta tcactctttt aacttctgtg cttaaaacgt catctgcatc   21360
aagaactagt ttaagctcac gacatcagtt tgctcctgga gcgacagtat tgtataaggg   21420
cgataaaatg gtgcttaacc tggacaggtc tcgtgttcca actgagtgta tagagaaaat   21480
```

-continued

```
tgaggccatt cttaaggaac ttgaaaagcc agcaccctga tgcgaccacg ttttagtcta   21540
cgtttatctg tctttactta atgtcctttg ttacaggcca gaaagcataa ctggcctgaa   21600
tattctctct gggcccactg ttccacttgt atcgtcggtc tgataatcag actgggacca   21660
cggtcccact cgtatcgtcg gtctgattat tagtctggga ccacggtccc actcgtatcg   21720
tcggtctgat tattagtctg ggaccacggt cccactcgta tcgtcggtct gataatcaga   21780
ctgggaccac ggtcccactc gtatcgtcgg tctgattatt agtctgggac catggtccca   21840
ctcgtatcgt cggtctgatt attagtctgg gaccacggtc ccactcgtat cgtcggtctg   21900
attattagtc tggaaccacg gtcccactcg tatcgtcggt ctgattatta gtctgggacc   21960
acggtcccac tcgtatcgtc ggtctgatta ttagtctggg accacgatcc cactcgtgtt   22020
gtcggtctga ttatcggtct gggaccacgg tcccacttgt attgtcgatc agactatcag   22080
cgtgagacta cgattccatc aatgcctgtc aagggcaagt attgacatgg tcgtcgtaac   22140
ctgtagaacg gagtaacctc ggtgtgcggt tgtatgcctg ctgtggattg ctgctgtgtc   22200
ctgcttatcc acaacatttt gcgcacggtt atgtggacaa aatacctggt tacccaggcc   22260
gtgccggcac gttaaccggg ctgcatccga tgcaagtgtg tcgctgtcga cgagctcgcg   22320
agctcggaca tgaggttgcc ccgtattcag tgtcgctgat ttgtattgtc tgaagttgct   22380
tttacgttaa gttgatgcag atcaattaat acgatacctg cgtcataatt gattatttga   22440
cgtggtttga tggcctccac gcacgttgtg atatgtagat gataatcatt atcactttac   22500
gggtcctttc cggtgatccg acaggttacg gggcggcgac ctcgcgggtt ttcgctattt   22560
atgaaaattt tccggtttaa ggcgtttccg ttcttcttcg tcataactta atgttttat   22620 ttaaatacc ctctgaaaag aaaggaaacg acaggtgctg aaagcgagct ttttggcctc   22680
tgtcgtttcc tttctctgtt tttgtccgtg gaatgaacaa tggaagtccg agctcatcgc   22740
taataacttc gtatagcata cattatacga agttatattc gatgcggccg atctagcaga   22800
aagtcaaaag cctccgaccg gaggcttttg acttctgtca cctaggttac gccccgccct   22860
gccactcatc gcagtactgt tgtaattcat taagcattct gccgacatgg aagccatcac   22920
aaacggcatg atgaacctga atcgccagcg gcatcagcac cttgtcgcct tgcgtataat   22980
atttgcccat ggtgaaaacg ggggcgaaga agttgtccat attggccacg tttaaatcaa   23040
aactggtgaa actcacccag ggattggctg agacgaaaaa catattctca ataaaccctt   23100
tagggaaata ggccaggttt tcaccgtaac acgccacatc ttgcgaatat atgtgtagaa   23160
actgccggaa atcgtcgtgg tattcactcc agagcgatga aaacgtttca gtttgctcat   23220
ggaaaacggt gtaacaaggg tgaacactat cccatatcac cagctcaccg tctttcattg   23280
ccatacgaaa ttccggatga gcattcatca ggcgggcaag aatgtgaata aaggccggat   23340
aaaacttgtg cttatttttc tttacggtct ttaaaaaggc cgtaatatcc agctgaacgg   23400
tctggttata ggtacattga gcaactgact gaaatgcctc aaaatgttct ttacgatgcc   23460
attgggatat atcaacggtg gtatatccag tgattttttt ctccatttta gcttccttag   23520
ctcctgaaaa tctcgataac tcaaaaaata cgcccggtag tgatcttatt tcattatggt   23580
gaaagttgga acctcttacg tgccgatcag attaaaacga aaggcccagt ctttcgactg   23640
agcctttcgt tttatttgac catgttggta tgatttaaat tcagtgcggc cgcgacttca   23700
agtcacgt                                                            23708
```

<210> SEQ ID NO 22

-continued

```
<211> LENGTH: 15565
<212> TYPE: DNA
<213> ORGANISM: Artificial Sequence
<220> FEATURE:
<223> OTHER INFORMATION: RSV A2 NLucP (without vector)

<400> SEQUENCE: 22
atgggcagca attcattgag tatgataaaa gttagattac aaaatttgtt tgacaatgat      60
gaagtagcat tgttaaaaat aacatgctat actgataaat taatacattt aactaacgct     120
ttggctaagg cagtgataca tacaatcaaa ttgaatggca ttgtgtttgt gcatgttatt     180
acaagtagtg atatttgccc taataataat attgtagtaa aatccaattt cacaacaatg     240
ccagtactac aaaatggagg ttatatatgg gaaatgatgg aattaacaca ttgctctcaa     300
cctaatggtc tactagatga caattgtgaa attaaattct ccaaaaaact aagtgattca     360
acaatgacca attatatgaa tcaattatct gaattacttg gatttgatct taatccataa     420
attataatta atatcaacta gcaaatcaat gtcactaaca ccattagtta atataaaaact     480 taacagaaga caaaaatggg gcaaataaat caattcagcc aacccaacca tggacacaac     540
ccacaatgat aatacaccac aaagactgat gatcacagac atgagaccgt tgtcacttga     600
gaccataata acatcactaa ccagagacat cataacacac aaatttatat acttgataaa     660
tcatgaatgc atagtgagaa aacttgatga aaaacaggcc acatttacat tcctggtcaa     720
ctatgaaatg aaactattac acaaagtagg aagcactaaa tataaaaaat atactgaata     780
caacacaaaa tatggcactt tccctatgcc aatattcatc aatcatgatg ggttcttaga     840
atgcattggc attaagccta caaagcatac tcccataata tacaagtatg atctcaatcc     900
ataaatttca acacaatatt cacacaatct aaaacaacaa ctctatgcat aactatactc     960
catagtccag atggagcctg aaaattatag taatttaaaa ttaaggagag atataagata    1020
gaagatgggg caaatacaaa gatggctctt agcaaagtca agttgaatga tacactcaac    1080
aaagatcaac ttctgtcatc cagcaaatac accatccaac ggagcacagg agatagtatt    1140
gatactccta attatgatgt gcagaaacac atcaataagt tatgtggcat gttattaatc    1200
acagaagatc taatcataa attcactggg ttaataggta tgttatatgc gatgtctagg    1260
ttaggaagag aagacaccat aaaaatactc agagatgcgg gatatcatgt aaaagcaaat    1320
ggagtagatg taacaacaca tcgtcaagac attaatggaa aagaaatgaa atttgaagtg    1380
ttaacattgg caagcttaac aactgaaatt caaatcaaca ttgagataga atctagaaaa    1440
tcctacaaaa aaatgctaaa agaaatggga gaggtagctc cagaatacag gcatgactct    1500
cctgattgtg ggatgataat attatgtata gcagcattag taataactaa attagcagca    1560
ggggacagat ctggtcttac agccgtgatt aggagagcta ataatgtcct aaaaaatgaa    1620
atgaaacgtt acaaaggctt actacccaag gacatagcca acagcttcta tgaagtgttt    1680
gaaaaacatc cccactttat agatgttttt gttcattttg gtatagcaca atcttctacc    1740
agaggtggca gtagagttga agggatttt gcaggattgt ttatgaatgc ctatggtgca    1800
gggcaagtga tgttacggtg gggagtctta gcaaaatcag ttaaaaatat tatgttagga    1860
catgctagtg tgcaagcaga aatggaacaa gttgttgagg tttatgaata tgcccaaaaa    1920
ttgggtggtg aagcaggatt ctaccatata ttgaacaacc aaaagcatc attattatct    1980 ttgactcaat ttcctcactt ctccagtgta gtattaggca atgctgctgg cctaggcata    2040
atgggagagt acagaggtac accgaggaat caagatctat atgatgcagc aaaggcatat    2100
gctgaacaac tcaaagaaaa tggtgtgatt aactacagtg tactagactt gacagcagaa    2160
```

-continued

```
gaactagagg ctatcaaaca tcagcttaat ccaaaagata atgatgtaga gctttgagtt      2220
aataaaaaat ggggcaaata aatcatcatg gaaaagtttg ctcctgaatt ccatggagaa      2280
gatgcaaaca acagggctac taaattccta gaatcaataa agggcaaatt cacatcaccc      2340
aaagatccca agaaaaaaga tagtatcata tctgtcaact caatagatat agaagtaacc      2400
aaagaaagcc ctataacatc aaattcaact attatcaacc caacaaatga gacagatgat      2460
actgcaggga acaagcccaa ttatcaaaga aaacctctag taagtttcaa agaagaccct      2520
acaccaagtg ataatccctt ttctaaacta tacaaagaaa ccatagaaac atttgataac      2580
aatgaagaag aatccagcta ttcatacgaa gaaataaatg atcagacaaa cgataatata      2640
acagcaagat tagataggat tgatgaaaaa ttaagtgaaa tactaggaat gcttcacaca      2700
ttagtagtgg caagtgcagg acctacatct gctcgggatg gtataagaga tgccatgatt      2760
ggtttaagag aagaaatgat agaaaaaatc agaactgaag cattaatgac caatgacaga      2820
ttagaagcta tggcaagact caggaatgag gaaagtgaaa agatggcaaa agacacatca      2880
gatgaagtgt ctctcaatcc aacatcagag aaattgaaca acctattgga agggaatgat      2940
agtgacaatg atctatcact tgaagatttc tgattagtta ccactcttca catcaacaca      3000
caataccaac agaagaccaa caaactaacc aacccaatca tccaaccaaa catccatccg      3060
ccaatcagcc aaacagccaa caaaacaacc agccaatcca aaactaacca cccggaaaaa      3120
atctataata tagttacaaa aaaaggaagg ggcaaataaa tcaatggtct tcacactcga      3180
agatttcgtt ggggactggc gacagacagc cggctacaac ctggaccaag tccttgaaca      3240
gggaggtgtg tccagtttgt ttcagaatct cggggtgtcc gtaactccga tccaaaggat      3300
tgtcctgagc ggtgaaaatg ggctgaagat cgacatccat gtcatcatcc cgtatgaagg      3360
tctgagcggc gaccaaatgg gccagatcga aaaaattttt aaggtggtgt accctgtgga      3420
tgatcatcac tttaaggtga tcctgcacta tggcacactg gtaatcgacg gggttacgcc      3480
gaacatgatc gactatttcg gacggccgta tgaaggcatc gccgtgttcg acggcaaaaa      3540
gatcactgta acagggaccc tgtggaacgg caacaaaatt atcgacgagc gcctgatcaa      3600
ccccgacggc tccctgctgt tccgagtaac catcaacgga gtgaccggct ggcggctgtg      3660
cgaacgcatt ctggcgaatt ctcacggctt tccgcctgag gttgaagagc aagccgccgg      3720
tacattgcct atgtcctgcg cacaagaaag cggtatggac cggcacccag ccgcttgtgc      3780
ttcagctcgc atcaacgtct aaattatagt aatttaaaaa gggtggggca aatatggaaa      3840
catacgtgaa caagcttcac gaaggctcca catacacagc tgctgttcaa tacaatgtct      3900
tagaaaaaga cgatgaccct gcatcactta caatatgggt gcccatgttc caatcatcta      3960
tgccagcaga tttacttata aaagaactag ctaatgtcaa catactagtg aaacaaatat      4020
ccacacccaa gggaccttca ctaagagtca tgataaactc aagaagtgca gtgctagcac      4080
aaatgcccag caaatttacc atatgcgcta atgtgtcctt ggatgaaaga agcaaactag      4140
catatgatgt aaccacaccc tgtgaaatca aggcatgtag tctaacatgc ctaaaatcaa      4200
aaaatatgtt gactacagtt aaagatctca ctatgaagac actcaaccct acacatgata      4260
ttattgcttt atgtgaattt gaaaacatag taacatcaaa aaaagtcata ataccaacat      4320
acctaagatc catcagtgtc agaaataaag atctgaacac acttgaaaat ataacaacca      4380
ctgaattcaa aaatgctatc acaaatgcaa aaatcatccc ttactcagga ttactattag      4440
tcatcacagt gactgacaac aaaggagcat tcaaatacat aaaagccaca agtcaattca      4500
```

-continued

```
tagtagatct tggagcttac ctagaaaaag aaagtatata ttatgttacc acaaattgga    4560
agcacacagc tacacgattt gcaatcaaac ccatggaaga ttaacctttt tcctctacat    4620
cagtgtgtta attcatacaa actttctacc tacattcttc acttcaccat cacaatcaca    4680
aacactctgt ggttcaacca atcaaacaaa acttatctga agtcccagat catcccaagt    4740
cattgtttat cagatctagt actcaaataa gttaataaaa aatatacaca tggggcaaat    4800
aatcattgga ggaaatccaa ctaatcacaa tatctgttaa catagacaag tccacacacc    4860
atacagaatc aaccaatgga aaatacatcc ataacaatag aattctcaag caaattctgg    4920
ccttacttta cactaataca catgatcaca acaataatct ctttgctaat cataatctcc    4980
atcatgattg caatactaaa caaactttgt gaatataacg tattccataa caaaacctttt    5040 gagttaccaa gagctcgagt caacacatag cattcatcaa tccaacagcc caaaacagta    5100
accttgcatt taaaaatgaa caacccctac ctctttacaa cacctcatta acatcccacc    5160
atgcaaacca ctatccatac tataaagtag ttaattaaaa atagtcataa caatgaacta    5220
ggatatcaag actaacaata acattggggc aaatgcaaac atgtccaaaa acaaggacca    5280
acgcaccgct aagacattag aaaggacctg ggacactctc aatcatttat tattcatatc    5340
atcgtgctta tataagttaa atcttaaatc tgtagcacaa atcacattat ccattctggc    5400
aatgataatc tcaacttcac ttataattgc agccatcata ttcatagcct cggcaaacca    5460
caaagtcaca ccaacaactg caatcataca agatgcaaca agccagatca agaacacaac    5520
cccaacatac ctcacccaga atcctcagct tggaatcagt ccctctaatc cgtctgaaat    5580
tacatcacaa atcaccacca tactagcttc aacaacacca ggagtcaagt caaccctgca    5640
atccacaaca gtcaagacca aaaacacaac aacaactcaa acacaaccca gcaagcccac    5700
cacaaaacaa cgccaaaaca aaccaccaag caaacccaat aatgattttc actttgaagt    5760
gttcaacttt gtaccctgca gcatatgcag caacaatcca acctgctggg ctatctgcaa    5820
aagaatacca aacaaaaaac caggaaagaa aaccactacc aagcccacaa aaaaaccaac    5880
cctcaagaca accaaaaaag atcccaaacc tcaaaccact aaatcaaagg aagtacccac    5940
caccaagccc acagaagagc caaccatcaa caccaccaaa acaaacatca taactacact    6000
actcacctcc aacaccacag gaaatccaga actcacaagt caaatggaaa ccttccactc    6060
aacttcctcc gaaggcaatc caagcccttc tcaagtctct acaacatccg agtacccatc    6120
acaaccttca tctccaccca acacaccacg ccagtagtta cttaaaaaca tattatcaca    6180
aaaagccatg accaacttaa acagaatcaa aataaactct ggggcaaata acaatggagt    6240
tgctaatcct caaagcaaat gcaattacca caatcctcac tgcagtcaca ttttgttttg    6300
cttctggtca aaacatcact gaagaatttt atcaatcaac atgcagtgca gttagcaaag    6360
gctatcttag tgctctgaga actggttggt ataccagtgt tataactata gaattaagta    6420
atatcaagga aaataagtgt aatggaacag atgctaaggt aaaattgata aaacaagaat    6480
tagataaata taaaaatgct gtaacagaat tgcagttgct catgcaaagc acaccaccaa    6540
caaacaatcg agccagaaga gaactaccaa ggtttatgaa ttatacactc aacaatgcca    6600
aaaaaaccaa tgtaacatta agcaagaaaa ggaaagaag atttcttgtt tttttgttag    6660
gtgttggatc tgcaatcgcc agtggcgttg ctgtatctaa ggtcctgcac ctagaagggg    6720
aagtgaacaa gatcaaaagt gctctactat ccacaaacaa ggctctagtc agcttatcaa    6780
atggagttag tgtcttaacc agcaaagtgt tagacctcaa aaactatata gataaacaat    6840
tgttacctat tgtgaacaag caaagctgca gcatatcaaa tatagaaact gtgatagagt    6900
```

-continued

```
tccaacaaaa gaacaacaga ctactagaga ttaccaggga atttagtgtt aatgcaggtg      6960
taactacacc tgtaagcact tacatgttaa ctaatagtga attattgtca ttaatcaatg      7020
atatgcctat aacaaatgat cagaaaaagt taatgtccaa caatgttcaa atagttagac      7080
agcaaagtta ctctatcatg tccataataa aagaggaagt cttagcatat gtagtacaat      7140
taccactata tggtgttata gatacaccct gttggaaact acacacatcc cctctatgta      7200
caaccaacac aaaagaaggg tccaacatct gtttaacaag aactgacaga ggatggtact      7260
gtgacaatgc aggatcagta tctttcttcc cacaagctga aacatgtaaa gttcaatcaa      7320
atcgagtatt ttgtgacaca atgaacagtt taacattacc aagtgaaata aatctctgca      7380
atgttgacat attcaacccc aaatatgatt gtaaaattat gacttcaaaa acagatgtaa      7440
gcagctccgt tatcacatct ctaggagcca ttgtgtcatg ctatggcaaa actaaatgta      7500
cagcatccaa taaaaatcgt ggaatcataa agacattttc taacgggtgc gattatgtat      7560
caaataaagg gatggacact gtgtctgtag gtaacacatt atattatgta aataagcaag      7620
aaggtaaaag tctctatgta aaaggtgaac caataataaa tttctatgac ccattagtat      7680
tcccctctga tgaatttgat gcatcaatat ctcaagtcaa cgagaagatt aaccagagcc      7740
tagcatttat tcgtaaatcc gatgaattat tacataatgt aaatgctggt aaatccacca      7800
caaatatcat gataactact ataattatag tgattatagt aatattgtta tcattaattg      7860
ctgttggact gctcttatac tgtaaggcca gaagcacacc agtcacacta agcaaagatc      7920
aactgagtgg tataaataat attgcattta gtaactaaat aaaaatagca cctaatcatg      7980
ttcttacaat ggtttactat ctgctcatag acaacccatc tgtcattgga ttttcttaaa      8040
atctgaactt catcgaaact ctcatctata aaccatctca cttacactat ttaagtagat      8100 tcctagtttta tagttatata aaacacaatt gaatgccaga ttaacttacc atctgtaaaa      8160
atgaaaactg gggcaaatat gtcacgaagg aatccttgca aatttgaaat tcgaggtcat      8220
tgcttaaatg gtaagaggtg tcattttagt cataattatt ttgaatggcc accccatgca      8280
ctgcttgtaa gacaaaactt tatgttaaac agaatactta agtctatgga taaaagtata      8340
gataccttat cagaaataag tggagctgca gagttggaca gacagaaga gtatgctctt      8400 ggtgtagttg gagtgctaga gagttatata ggatcaataa acaatataac taaacaatca      8460
gcatgtgttg ccatgagcaa actcctcact gaactcaata gtgatgatat caaaaagctg      8520
agggacaatg aagagctaaa ttcacccaag ataagagtgt acaatactgt catatcatat      8580
attgaaagca acaggaaaaa caataaacaa actatccatc tgttaaaaag attgccagca      8640
gacgtattga agaaaccat caaaaacaca ttggatatcc ataagagcat aaccatcaac      8700
aacccaaaag aatcaactgt tagtgataca aatgaccatg ccaaaaataa tgatactacc      8760
tgacaaatat ccttgtagta aacttccat actaataaca agtagatgta gagttactat      8820
gtataatcaa aagaacacac tatatttcaa tcaaacaac ccaaataacc atatgtactc      8880
accgaatcaa acattcaatg aaatccattg gacctctcaa gaattgattg acacaattca      8940 aattttcta caacatctag gtattattga ggatatatat acaatatata tattagtgtc      9000
ataacactca attctaacac tcaccacatc gttacattat taattcaaac aattcaagtt      9060
gtgggacaaa atggatccca ttattaatgg aaattctgct aatgtttatc taaccgatag      9120
ttatttaaaa ggtgttatct ctttctcaga gtgtaatgct ttaggaagtt acatattcaa      9180
tggtccttat ctcaaaaatg attataccaa cttaattagt agacaaaatc cattaataga      9240
```

-continued

```
acacatgaat ctaaagaaac taaatataac acagtcctta atatctaagt atcataaagg    9300
tgaaataaaa ttagaagaac ctacttattt tcagtcatta cttatgacat acaagagtat    9360
gacctcgtca gaacagattg ctaccactaa tttacttaaa aagataataa gaagagctat    9420
agaaataagt gatgtcaaag tctatgctat attgaataaa ctagggctta aagaaaagga    9480
caagattaaa tccaacaatg gacaagatga agacaactca gttattacga ccataatcaa    9540
agatgatata ctttcagctg ttaaagataa tcaatctcat cttaaagcag acaaaaatca    9600
ctctacaaaa caaaaagaca caatcaaaac aacactcttg aagaaattga tgtgttcaat    9660
gcaacatcct ccatcatggt taatacattg gtttaactta tacacaaaat taaacaacat    9720
attaacacag tatcgatcaa atgaggtaaa aaaccatggg tttacattga tagataatca    9780
aactcttagt ggatttcaat ttattttgaa ccaatatggt tgtatagttt atcataagga    9840
actcaaaaga attactgtga caacctataa tcaattcttg acatggaaag atattagcct    9900
tagtagatta aatgtttgtt taattacatg gattagtaac tgcttgaaca cattaaataa    9960
aagcttaggc ttaagatgcg gattcaataa tgttatcttg acacaactat tcctttatgg   10020
agattgtata ctaaagctat ttcacaatga ggggttctac ataataaaag aggtagaggg   10080
atttattatg tctctaattt taaatataac agaagaagat caattcagaa aacgatttta   10140
taatagtatg ctcaacaaca tcacagatgc tgctaataaa gctcagaaaa atctgctatc   10200
aagagtatgt catacattat tagataagac agtgtccgat aatataataa atggcagatg   10260
gataattcta ttaagtaagt tccttaaatt aattaagctt gcaggtgaca ataaccttaa   10320
caatctgagt gaactatatt ttttgttcag aatatttgga cacccaatgg tagatgaaag   10380
acaagccatg gatgctgtta aaattaattg caatgagacc aaattttact tgttaagcag   10440
tctgagtatg ttaagaggtg cctttatata tagaattata aaagggtttg taaataatta   10500
caacagatgg cctactttaa gaaatgctat tgttttaccc ttaagatggt aacttacta    10560 taaactaaac acttatcctt ctttgttgga acttacagaa agagatttga ttgtgttatc   10620
aggactacgt ttctatcgtg agtttcggtt gcctaaaaaa gtggatcttg aaatgattat   10680
aaatgataaa gctatatcac ctcctaaaaa tttgatatgg actagtttcc ctagaaatta   10740
catgccatca cacatacaaa actatataga acatgaaaaa ttaaaatttt ccgagagtga   10800
taaatcaaga gagtattag agtattattt aagagataac aaattcaatg aatgtgattt    10860
atacaactgt gtagttaatc aaagttatct caacaaccct aatcatgtgg tatcattgac   10920
aggcaaagaa agagaactca gtgtaggtag aatgtttgca atgcaaccgg gaatgttcag   10980
acaggttcaa atattggcag agaaaatgat agctgaaaac attttacaat tctttcctga   11040
aagtcttaca agatatggtg atctagaact acaaaaaaata ttagaattga aagcaggaat   11100
aagtaacaaa tcaaatcgct acaatgataa ttacaacaat tacattagta agtgctctat   11160
catcacagat ctcagcaaat tcaatcaagc atttcgatat gaaacgtcat gtatttgtag   11220
tgatgtgctg gatgaactgc atggtgtaca atctctattt tcctggttac atttaactat   11280
tcctcatgtc acaataatat gcacatatag gcatgcaccc ccctatatag gagatcatat   11340
tgtagatctt aacaatgtag atgaacaaag tggattatat agatatcaca tgggtggcat   11400
cgaagggtgg tgtcaaaaac tgtggaccat agaagctata tcactattgg atctaatatc   11460
tctcaaaggg aaattctcaa ttactgcttt aattaatggt gacaatcaat caatagatat   11520
aagcaaacca atcagactca tggaaggtca aactcatgct caagcagatt atttgctagc   11580
attaaatagc cttaaattac tgtataaaga gtatgcaggc ataggccaca aattaaaagg   11640
```

-continued

```
aactgagact tatatatcac gagatatgca atttatgagt aaaacaattc aacataacgg   11700
tgtatattac ccagctagta taaagaaagt cctaagagtg ggaccgtgga taaacactat   11760
acttgatgat ttcaaagtga gtctagaatc tataggtagt ttgacacaag aattagaata   11820
tagaggtgaa agtctattat gcagtttaat atttagaaat gtatggttat ataatcagat   11880
tgctctacaa ttaaaaaatc atgcattatg taacaataaa ctatatttgg acatattaaa   11940
ggttctgaaa cacttaaaaa ccttttttaa tcttgataat attgatacag cattaacatt   12000
gtatatgaat ttacccatgt tatttggtgg tggtgatccc aacttgttat atcgaagttt   12060
ctatagaaga actcctgact tcctcacaga ggctatagtt cactctgtgt tcatacttag   12120
ttattataca aaccatgact taaaagataa acttcaagat ctgtcagatg atagattgaa   12180
taagttctta acatgcataa tcacgtttga caaaaaccct aatgctgaat tcgtaacatt   12240
gatgagagat cctcaagctt tagggtctga gagacaagct aaaattacta gcgaaatcaa   12300
tagactggca gttacagagg tttttgagtac agctccaaac aaaatattct ccaaaagtgc   12360
acaacattat actactacag agatagatct aaatgatatt atgcaaaata tagaacctac   12420
atatcctcat gggctaagag ttgtttatga aagtttaccc ttttataaag cagagaaaat   12480
agtaaatctt atatcaggta caaaatctat aactaacata ctggaaaaaa cttctgccat   12540
agacttaaca gatattgata gagccactga gatgatgagg aaaaacataa ctttgcttat   12600
aaggatactt ccattggatt gtaacagaga taaaagagag atattgagta tggaaaacct   12660
aagtattact gaattaagca aatatgttag ggaaagatct tggtctttat ccaatatagt   12720
tggtgttaca tcacccagta tcatgtatac aatggacatc aaatatacta caagcactat   12780
atctagtggc ataattatag agaaatataa tgttaacagt ttaacacgtg gtgagagagg   12840
acccactaaa ccatgggttg gttcatctac acaagagaaa aaaacaatgc cagtttataa   12900
tagacaagtc ttaaccaaaa aacagagaga tcaaatagat ctattagcaa aattggattg   12960
ggtgtatgca tctatagata acaaggatga attcatggaa gaactcagca taggaaccct   13020
tgggttaaca tatgaaaagg ccaagaaatt atttccacaa tatttaagtg tcaattattt   13080
gcatcgcctt acagtcagta gtagaccatg tgaattccct gcatcaatac cagcttatag   13140
aacaacaaat tatcactttg acactagccc tattaatcgc atattaacag aaaagtatgg   13200
tgatgaagat attgacatag tattccaaaa ctgtataagc tttggcctta gtttaatgtc   13260
agtagtagaa caatttacta atgtatgtcc taacagaatt attctcatac ctaagcttaa   13320
tgagatacat ttgatgaaac ctcccatatt cacaggtgat gttgatattc acaagttaaa   13380
acaagtgata caaaaacagc atatgttttt accagacaaa ataagtttga ctcaatatgt   13440
ggaattattc ttaagtaata aaacactcaa atctggatct catgttaatt ctaatttaat   13500
attggcacat aaaatatctg actattttca taatacttac attttaagta ctaatttagc   13560
tggacattgg attctgatta tacaacttat gaaagattct aaaggtattt ttgaaaaaga   13620 ttgggggagag ggatatataa ctgatcatat gtttattaat ttgaaagttt tcttcaatgc   13680
ttataagacc tatctcttgt gttttcataa aggttatggc aaagcaaagc tggagtgtga   13740
tatgaacact tcagatcttc tatgtgtatt ggaattaata gacagtagtt attggaagtc   13800
tatgtctaag gtattttttag aacaaaaagt tatcaaatac attcttagcc aagatgcaag   13860
tttacataga gtaaaaggat gtcatagctt caaattatgg tttcttaaac gtcttaatgt   13920
agcagaattc acagtttgcc cttgggttgt taacatagat tatcatccaa cacatatgaa   13980
```

-continued

```
agcaatatta acttatatag atcttgttag aatgggattg ataaatatag atagaataca  14040
cattaaaaat aaacacaaat tcaatgatga attttatact tctaatctct tctacattaa  14100
ttataacttc tcagataata ctcatctatt aactaaacat ataaggattg ctaattctga  14160
attagaaaat aattacaaca aattatatca tcctacacca gaaaccctag agaatatact  14220
agccaatccg attaaaagta atgacaaaaa gacactgaat gactattgta taggtaaaaa  14280
tgttgactca ataatgttac cattgttatc taataagaag cttattaaat cgtctgcaat  14340
gattagaacc aattacagca aacaagattt gtataattta ttccctatgg ttgtgattga  14400
tagaattata gatcattcag gcaatacagc caaatccaac caactttaca ctactacttc  14460
ccaccaaata tctttagtcc acaatagcac atcactttac tgcatgcttc cttggcatca  14520
tattaataga ttcaattttg tatttagttc tacaggttgt aaaattagta tagagtatat  14580
tttaaaagat cttaaaatta aagatcccaa ttgtatagca ttcataggtg aaggagcagg  14640
gaatttatta ttgcgtacag tagtggaact tcatcctgac ataagatata tttacagaag  14700
tctgaaagat tgcaatgatc atagtttacc tattgagttt ttaaggctgt acaatggaca  14760
tatcaacatt gattatggtg aaaatttgac cattcctgct acagatgcaa ccaacaacat  14820
tcattggtct tatttacata taaagtttgc tgaacctatc agtcttttg tctgtgatgc  14880 cgaattgtct gtaacagtca actggagtaa aattataata gaatggagca agcatgtaag  14940
aaagtgcaag tactgttcct cagttaataa atgtatgtta atagtaaaat atcatgctca  15000
agatgatatt gatttcaaat tagacaatat aactatatta aaaacttatg tatgcttagg  15060
cagtaagtta aagggatcgg aggtttactt agtccttaca ataggtcctg cgaatatatt  15120
cccagtattt aatgtagtac aaaatgctaa attgatacta tcaagaacca aaaatttcat  15180
catgcctaag aaagctgata aagagtctat tgatgcaaat attaaaagtt tgataccctt  15240
tctttgttac cctataacaa aaaaaggaat taatactgca ttgtcaaaac taaagagtgt  15300
tgttagtgga gatatactat catattctat agctggacgt aatgaagttt tcagcaataa  15360
acttataaat cataagcata tgaacatctt aaaatggttc aatcatgttt taaatttcag  15420
atcaacagaa ctaaactata accatttata tatggtagaa tctacatatc cttacctaag  15480
tgaattgtta aacagcttga caaccaatga acttaaaaaa ctgattaaaa tcacaggtag  15540
tctgttatac aactttcata atgaa                                        15565
```

ANTI-RESPIRATORY SYNCYTIAL VIRUS (RSV) ANTIBODY CELL-BASED POTENCY ASSAY

CROSS-REFERENCE TO RELATED APPLICATIONS

This application is a national stage application of International Patent Application No. PCT/US2021/058377 filed Nov. 8, 2021, published as WO2022103671 on May 19, 2022; which claims the benefit of U.S. provisional patent application No. 63/112,978, filed Nov. 12, 2020, each of which is incorporated by reference in its entirety herein.

REFERENCE TO SEQUENCE LISTING SUBMITTED ELECTRONICALLY

The sequence listing of the present application is submitted electronically via EFS-Web as an ASCII formatted sequence listing with a file name "25140WOPCTSEQ.txt", filed Nov. 8, 2021 as part of international application number PCT/US2021/058377, and a size of 85 Kb. This sequence listing submitted electronically is part of the specification and is herein incorporated by reference in its entirety.

FIELD OF THE INVENTION

The present disclosure describes a cell-based potency assay for measuring anti-Respiratory Syncytial Virus (RSV) antibody activity using a cultured system with A549 cells and an RSV reporter virus.

BACKGROUND OF THE INVENTION

The human RSV genome is a single-stranded negative-sense RNA molecule of approximately 15 kb that encodes 11 proteins. Two of these proteins are the main surface glycoproteins of the virion. These are (i) the attachment (G) protein, which mediates virus binding to cells, and (ii) the fusion (F) protein, which promotes both fusion of the viral and cell membranes at the initial stages of the infectious cycle and fusion of the membrane of infected cells with those of adjacent cells to form characteristic syncytia. The attachment protein G binds cellular surface receptors and interacts with F. This interaction triggers a conformational change in F to induce membrane fusion, thereby releasing the viral ribonucleoprotein complex into the host cell cytoplasm.

Monoclonal antibodies against the F protein or the G protein have been shown to have neutralizing effect in vitro and prophylactic effects in vivo. See, e.g., Beeler and Coelingh 1989, J. Virol. 63:2941-50; Garcia-Barreno et al., 1989, J. Virol. 63:925-32; Taylor et al., 1984, Immunology 52: 137-142; Walsh et al., 1984, Infection and Immunity 43:756-758; and U.S. Pat. Nos. 5,842,307 and 6,818,216. Neutralizing epitopes on the F glycoprotein were originally mapped by identifying amino acids that were altered in antibody escape variants and by assessing antibody binding to RSV F-derived peptides.

Several anti-RSV antibodies are in clinical development for use as a passive immunotherapy agent to protect against RSV infection in infants and the elderly who have immature or compromised immune systems. Such anti-RSV antibodies must be highly potent in order to act effectively as passive immunotherapy agents. Thus, there is a need for RSV neutralization assay as a cell-based potency assay, for example, to confirm potency of clinical batches of anti-RSV antibodies.

The industry standard of virus neutralization assay is the plaque reduction neutralization test (PRNT) (McKimm-Breschkin J L. 2004) . The PRNT is based on manual plaque counting and is low throughput, requires significant resources, and has high variability. Thus, an assay for determining the potency of anti-RSV antibodies that is fast, easy to use, and has low variability would be an asset for the development of anti-RSV antibody clinical candidates.

SUMMARY OF THE INVENTION

The present invention provides respiratory syncytial viruses engineered to encode reporter genes, nucleic acids encoding such viruses, and cell-based potency assays for measuring anti-RSV antibody activity using a cell culture system.

In one aspect, the disclosure provides an expression vector for producing an infectious recombinant respiratory syncytial virus (RSV) comprising: a) a nucleic acid sequence encoding a respiratory syncytial virus; and b) a reporter gene flanked by an RSV gene start sequence and an RSV gene end sequence, the reporter gene and flanking RSV gene start and RSV gene end sequences located between the P and M genes of the respiratory syncytial virus.

In another aspect, the disclosure provides a respiratory syncytial virus comprising: a) a nucleic acid sequence encoding a respiratory syncytial virus; and b) a reporter gene flanked by an RSV gene start sequence and an RSV gene end sequence, the reporter gene and flanking RSV gene start and RSV gene end sequences located between the P and M genes of the respiratory syncytial virus.

In some embodiments of the foregoing expression vector and respiratory syncytial virus, a) the reporter gene encodes a luminescent enzyme that catalyzes a luminescent substrate; or b) the reporter gene encodes a fluorescent protein. In some embodiments, the luminescent enzyme is a luciferase. In some embodiments, the RSV gene start sequence is SEQ ID NO: 16 and the RSV gene end sequence is SEQ ID NO: 17. In some embodiments, the sequence of the reporter gene is SEQ ID NO: 18. In some embodiments, the reporter gene flanked by an RSV gene start sequence and an RSV gene end sequence is SEQ ID NO: 15. In some embodiments, the respiratory syncytial virus is strain A2 or comprises a nucleic acid of SEQ ID NO: 14.

In another aspect, the disclosure provides a method for measuring the activity of an anti-respiratory syncytial virus (RSV) antibody or antigen binding fragment thereof, the method comprising the steps of: a) combining (i) the anti-RSV antibody or antigen binding fragment thereof, (ii) an RSV virus comprising a reporter gene, and (iii) one or more cells infectable by the RSV virus; and b) detecting expression of the reporter gene.

In some embodiments of the foregoing method, the one or more cells infectable by the RSV virus are combined with the anti-RSV antibody or antigen binding fragment thereof before the RSV virus is added. In some embodiments, a) the reporter gene encodes a luminescent enzyme that catalyzes a luminescent substrate, and detecting expression of the reporter gene comprises detecting luminescence of the luminescent substrate; or b) the reporter gene encodes a fluorescent protein, and detecting expression of the reporter gene comprises detecting fluorescent light emission from the fluorescent protein. In some embodiments, the reporter gene is a luminescent enzyme. In some embodiments, the luminescent enzyme is a luciferase. In some embodiments, the reporter gene is a fluorescent protein. In some embodiments, the fluorescent protein is a protein excited in the UV wavelength, such as Sirius, Sandercyanin, shBFP-N158S/L173I. In some embodiments, the fluorescent protein is a protein excited by a blue wavelength of light, such as Azurite, EBFP2, mKalama1, mTagBFP2, TagBFP, or shBFP. In some embodiments, the fluorescent protein is a protein excited by a cyan wavelength of light, such as ECFP, Cerulean, mCerulean3, SCFP3A, CyPet, mTurquoise, mTurquoise2, TagCFP, mTFP1, monmeric Midoriishi-Cyan, or Aquamarine. In some embodiments, the fluorescent protein is a protein excited by a green wavelength of light, such as GFP, TurboGFP, TagGFP2, mUKG, Superfolder GFP, Emerald, EGFP, Monomeric Azami Green, mWasabi, Clover, mNeonGreen, NowGFP, or mClover3. In some embodiments, the fluorescent protein is a protein excited by a yellow wavelength of light, such as TagYFP, EYFP, Topaz, Venus SYFP2, Citrine, Ypet, IanRFP-deltaS83, mPapayal, or mCyRFP1. In some embodiments, the fluorescent protein is a protein excited by an orange wavelength of light, such as Monomeric Kusabira-Orange, mOrange, mOrange2, mKOkappa, or mKO2, In some embodiments, the fluorescent protein is a protein excited by a red wavelength of light, such as TagRFP, TagRFP-T, RRvT, mRuby, mRuby2, mTangerine, mApple, mStrawberry, FusionRed, mCherry, mNectarine, mRuby3, mScarlet, or mScarlet-I. In some embodiments, the fluorescent protein is a protein excited by a far-red wavelength of light, such as mKate2, hcRed-Tandem, mPlum, mRaspberry, mNeptune, NirFP, TagRFP657, TagRFP675, mCardinal, mStable, mMaroon1, or mGarnet2. In some embodiments, the fluorescent protein is a protein excited by a near infra-red wavelength of light, such as iFP1.4, iRFP713 (iRFP), iRFP670, iRFP682, iRFP702, iRFP720, iFP2.0, mIFP, TDsmURFP, or miRFP670. In some embodiments, the fluorescent protein is Sapphire, T-Sapphire, or mAmetrine. In some embodiments, the fluorescent protein has a long Stokes shift, such as mKeima, mBeRFP, LSS-mKate2, LSS-mKate1, LSSmOrange, CyOFP1, or Sandercyanin.

In some embodiments of the foregoing method, the method further comprises a step of adding a luciferase substrate.

In some embodiments of the foregoing method, the one or more cells infectable by the RSV virus are A549 cells.

In another aspect, the disclosure provides a method for measuring the activity of an anti-respiratory syncytial virus (RSV) antibody or antigen binding fragment thereof, the method comprising the steps of: a) combining the anti-RSV antibody or antigen-binding fragment thereof with an RSV virus comprising a nucleic acid sequence encoding a luciferase; b) adding the mixture of step a) to one or more A549 cells; c) adding a luciferase substrate to the mixture of step b); and d) detecting luminescence of the luciferase substrate.

In some embodiments of any one of the foregoing methods wherein the reporter gene is a luciferase, the nucleic acid sequence encoding the luciferase encodes a nanoluciferase.

In some embodiments of any one of the foregoing aspects, the anti-RSV antibody or antigen binding fragment thereof comprises: (a) three heavy chain complementarity determining regions (HC-CDRs), wherein HC-CDR1 is SEQ ID NO: 1, HC-CDR2 is SEQ ID NO: 2, and HC-CDR3 is SEQ ID NO: 3; and (b) three light chain complementarity determining regions (LC-CDRs), wherein LC-CDR1 is SEQ ID NO: 4, LC-CDR2 is SEQ ID NO: 5, and LC-CDR3 is SEQ ID NO: 6. In some embodiments, the anti-RSV antibody or antigen binding fragment thereof comprises a heavy chain variable region of SEQ ID NO: 7 and a light chain variable region of SEQ ID NO: 8. In some embodiments, the anti-RSV antibody or antigen binding fragment thereof comprises a heavy chain and a light chain, and wherein the heavy chain comprises SEQ ID NO: 9 and the light chain comprises SEQ ID NO: 10. In some embodiments, the anti-RSV antibody or antigen binding fragment thereof is an antibody comprising two heavy chains of SEQ ID NO: 9 and two light chains of SEQ ID NO: 10.

In some embodiments of the foregoing methods, the RSV virus comprises a) a nucleic acid sequence encoding a respiratory syncytial virus; and b) a reporter gene flanked by an RSV gene start sequence and an RSV gene end sequence, the reporter gene and flanking RSV gene start and RSV gene end sequences located between the P and M genes of the respiratory syncytial virus. In some embodiments, a) the reporter gene encodes a luminescent enzyme that catalyzes a luminescent substrate, and detecting expression of the reporter gene comprises detecting luminescence of the luminescent substrate; or b) the reporter gene encodes a fluorescent protein, and detecting expression of the reporter gene comprises detecting fluorescent light emission from the fluorescent protein. In some embodiments, the luminescent enzyme is a luciferase. In some embodiments, the RSV gene start sequence is SEQ ID NO: 16 and the RSV gene end sequence is SEQ ID NO: 17. In some embodiments, the sequence of the reporter gene is SEQ ID NO: 18. In some embodiments, the reporter gene flanked by an RSV gene start sequence and an RSV gene end sequence is SEQ ID NO: 15. In some embodiments, the respiratory syncytial virus is strain A2 or comprises a nucleic acid of SEQ ID NO: 14.

BRIEF DESCRIPTION OF THE DRAWINGS

FIGS. 2A-2C show exemplary dilution plate maps. Maps for plates 1-3 are shown in FIGS. 2A, 2B and 2C, respectively.

DETAILED DESCRIPTION

Figure 1:
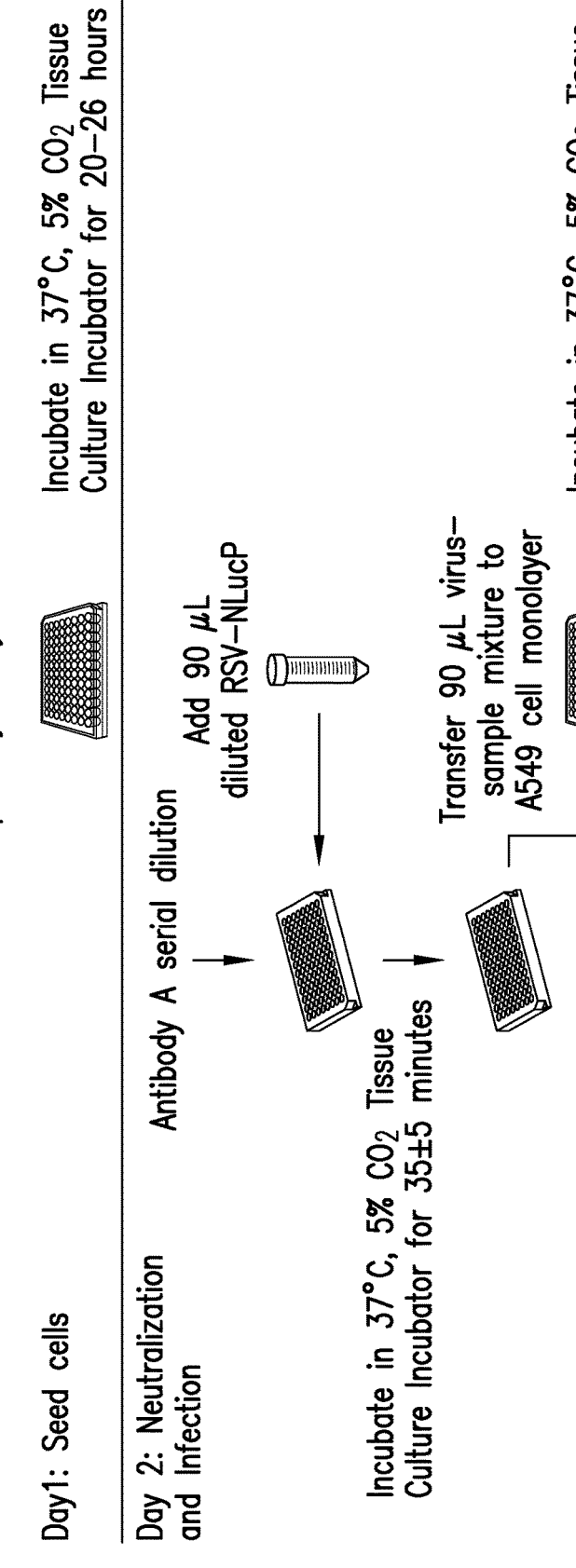
FIG. 1 shows a schematic diagram of a cell-based potency assay with anti-RSV Antibody A.
Figure 3:
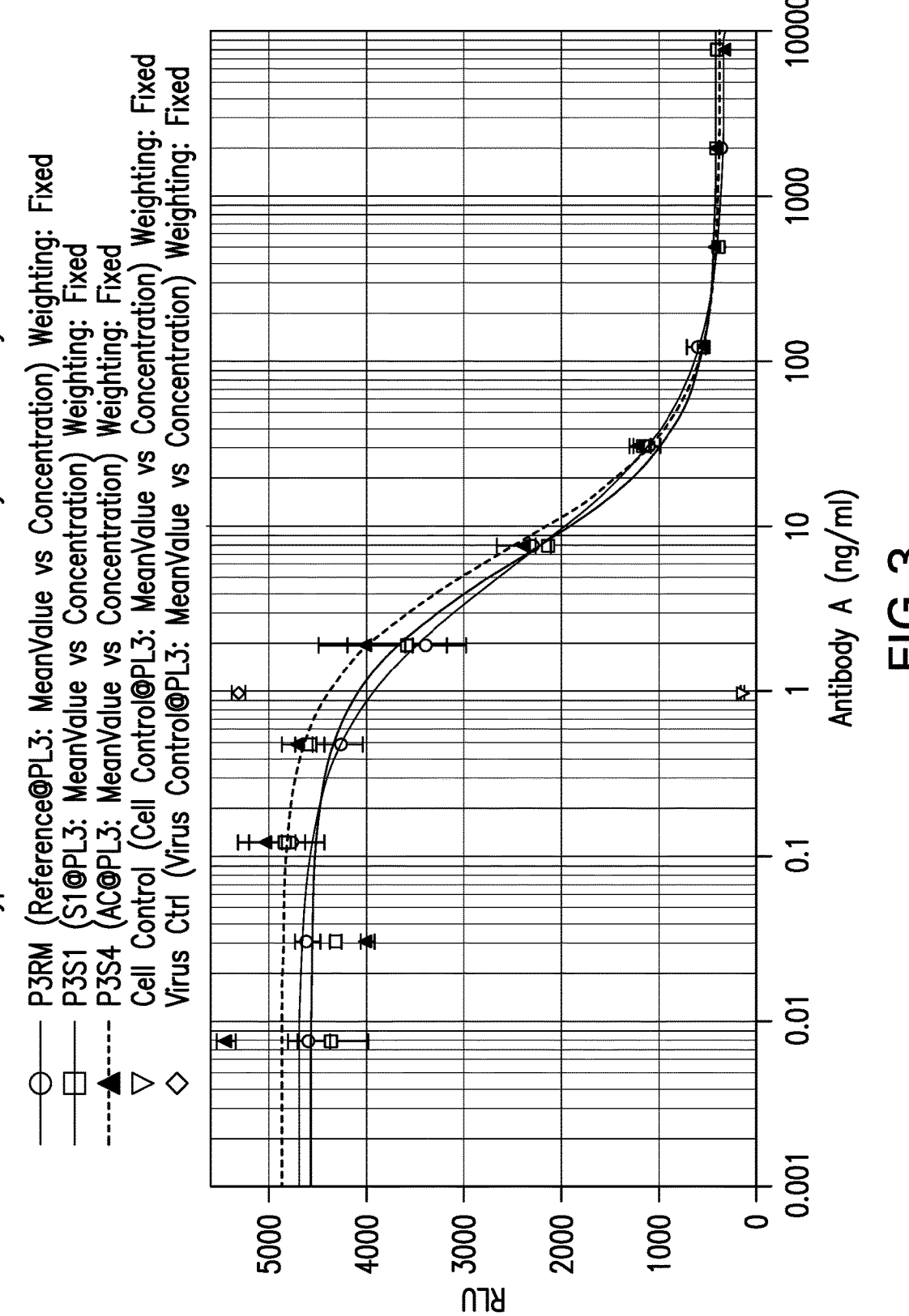
FIG. 3 shows a graph of a typical result of cell-based potency assay for Antibody A.

Disclosed herein is a cell-based potency assay for measuring anti-RSV antibody activity using a cultured system with cells including for example A549 cells. In one embodiment, the assay utilizes an RSV reporter virus, RSV-NLucP, which encodes a gene for NanoLuc® luciferase enzyme within the RSV genome. After infecting cells, the RSV-NLucP expresses the NanoLuc® luciferase, which generates luminescence signal upon the addition of the luciferase substrate. Luminescence signal is directly proportional to RSV-NLucP infectivity. Introduction of anti-RSV antibody blocks the entry of RSV-NLucP into the host cells and therefore inhibit luminescence signal. In one embodiment, the anti-RSV antibody is Antibody A having two heavy chains of SEQ ID NO: 9 and two light chains of SEQ ID NO: 10. The assay is robust, quantitative and accurate.

Certain technical and scientific terms are defined below. Unless specifically defined elsewhere in this specification, all other technical and scientific terms used herein have the meaning commonly understood by one of ordinary skill in the art to which this invention belongs.

As used herein, including the appended claims, the singular forms of words such as "a," "an," and "the," include their corresponding plural references unless the context clearly dictates otherwise.

As used herein, the term "antibody" refers to any form of antibody that exhibits the desired biological or binding activity. Thus, it is used in the broadest sense and specifically covers, but is not limited to, monoclonal antibodies (including full length monoclonal antibodies), polyclonal antibodies, multispecific antibodies (e.g., bispecific antibodies), humanized, fully human antibodies, chimeric antibodies and camelized single domain antibodies. "Parental antibodies" are antibodies obtained by exposure of an immune system to an antigen prior to modification of the antibodies for an intended use, such as humanization of an antibody for use as a human therapeutic.

In general, the basic (or "full-length") antibody structural unit comprises a tetramer. Each tetramer includes two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of the heavy chain may define a constant region primarily responsible for effector function. Typically, human light chains are classified as kappa and lambda light chains. Furthermore, human heavy chains are typically classified as mu, delta, gamma, alpha, or epsilon, and define the antibody's isotype as IgM, IgD, IgG, IgA, and IgE, respectively. Within light and heavy chains, the variable and constant regions are joined by a "J" region of about 12 or more amino acids, with the heavy chain also including a "D" region of about 10 more amino acids. See generally, Fundamental Immunology Ch. 7 (Paul, W., ed., 2nd ed. Raven Press, N.Y. (1989). In the context of an antibody or antigen binding fragment thereof, the terms "domain" and "region" can be used interchangeably, where appropriate.

The variable regions of each light/heavy chain pair form the antibody binding site. Thus, in general, an intact antibody has two binding sites. Except in bifunctional or bispecific antibodies, the two binding sites are, in general, the same.

Typically, the variable domains of both the heavy and light chains comprise three hypervariable regions, also called complementarity determining regions (CDRs), which are located within relatively conserved framework regions (FR). The CDRs are usually aligned by the framework regions, enabling binding to a specific epitope. In general, from N-terminal to C-terminal, both light and heavy chains variable domains comprise FR1, CDR1, FR2, CDR2, FR3, CDR3 and FR4. The assignment of amino acids to each domain is, generally, in accordance with the definitions of Sequences of Proteins of Immunological Interest, Kabat, et al.; National Institutes of Health, Bethesda, Md.; 5$^{th}$ ed.; NIH Publ. No. 91-3242 (1991); Kabat (1978) Adv. Prot. Chem. 32:1-75; Kabat, et al., (1977) J. Biol. Chem. 252: 6609-6616; Chothia, et al., (1987) J Mol. Biol. 196:901-917 or Chothia, et al., (1989) Nature 342:878-883.

As used herein, unless otherwise indicated, "antibody fragment" or "antigen binding fragment" refers to antigen binding fragments of antibodies, i.e. antibody fragments that retain the ability to bind specifically to the antigen bound by the full-length antibody, e.g. fragments that retain one or more CDR regions. Examples of antibody binding fragments include, but are not limited to, Fab, Fab', F(ab')$_2$, and Fv fragments; diabodies; linear antibodies; single-chain antibody molecules, e.g., sc-Fv; nanobodies and multispecific antibodies formed from antibody fragments.

An antibody that "specifically binds to" a specified target protein is an antibody that exhibits preferential binding to that target as compared to other proteins, but this specificity does not require absolute binding specificity. An antibody is considered "specific" for its intended target if its binding is determinative of the presence of the target protein in a sample, e.g. without producing undesired results such as false positives. Antibodies, or binding fragments thereof, useful in the present invention will bind to the target protein with an affinity that is at least two fold greater, preferably at least ten times greater, more preferably at least 20-times greater, and most preferably at least 100-times greater than the affinity with non-target proteins. As used herein, an antibody is said to bind specifically to a polypeptide comprising a given amino acid sequence, e.g. the amino acid sequence of an RSV antigen, if it binds to polypeptides comprising that sequence but does not bind to proteins lacking that sequence.

"Chimeric antibody" refers to an antibody in which a portion of the heavy and/or light chain is identical with or homologous to corresponding sequences in an antibody derived from a particular species (e.g., human) or belonging to a particular antibody class or subclass, while the remainder of the chain(s) is identical with or homologous to corresponding sequences in an antibody derived from another species (e.g., mouse) or belonging to another antibody class or subclass, as well as fragments of such antibodies, so long as they exhibit the desired biological activity.

"Human antibody" refers to an antibody that comprises human immunoglobulin protein sequences only. A human antibody may contain murine carbohydrate chains if produced in a mouse, in a mouse cell, or in a hybridoma derived from a mouse cell. Similarly, "mouse antibody" or "rat antibody" refer to an antibody that comprises only mouse or rat immunoglobulin sequences, respectively.

"Humanized antibody" refers to forms of antibodies that contain sequences from non-human (e.g., murine) antibodies as well as human antibodies. Such antibodies contain minimal sequence derived from non-human immunoglobulin. In general, the humanized antibody will comprise substantially all of at least one, and typically two, variable domains, in which all or substantially all of the hypervariable loops correspond to those of a non-human immunoglobulin and all or substantially all of the FR regions are those of a human immunoglobulin sequence. The humanized antibody optionally also will comprise at least a portion of an immunoglobulin constant region (Fc), typically that of a human immunoglobulin. The prefix "hum", "hu" or "h" is added to antibody clone designations when necessary to distinguish humanized antibodies from parental rodent antibodies. The humanized forms of rodent antibodies will generally comprise the same CDR sequences of the parental rodent antibodies, although certain amino acid substitutions may be included to increase affinity, increase stability of the humanized antibody, or for other reasons.

"Comprising" or variations such as "comprise", "comprises" or "comprised of" are used throughout the specification and claims in an inclusive sense, i.e., to specify the presence of the stated features but not to preclude the presence or addition of further features that may materially enhance the operation or utility of any of the embodiments of the invention, unless the context requires otherwise due to express language or necessary implication.

"Conservatively modified variants" or "conservative substitution" refers to substitutions of amino acids in a protein with other amino acids having similar characteristics (e.g. charge, side-chain size, hydrophobicity/hydrophilicity, backbone conformation and rigidity, etc.), such that the changes can frequently be made without altering the biological activity or other desired property of the protein, such as antigen affinity and/or specificity. Those of skill in this art recognize that, in general, single amino acid substitutions in non-essential regions of a polypeptide do not substantially alter biological activity (see, e.g., Watson et al. (1987) *Molecular Biology of the Gene*, The Benj amin/Cummings Pub. Co., p. 224 (4th Ed.)). In addition, substitutions of structurally or functionally similar amino acids are less likely to disrupt biological activity. Exemplary conservative substitutions are set forth in Table 1 below.

TABLE 1

| Exemplary Conservative Amino Acid Substitutions | |
|---|---|
| Original residue | Conservative substitution |
| Ala (A) | Gly; Ser |
| Arg (R) | Lys; His |
| Asn (N) | Gln; His |
| Asp (D) | Glu; Asn |
| Cys (C) | Ser; Ala |
| Gln (Q) | Asn |
| Glu (E) | Asp; Gln |
| Gly (G) | Ala |
| His (H) | Asn; Gln |
| Ile (I) | Leu; Val |
| Leu (L) | Ile; Val |
| Lys (K) | Arg; His |
| Met (M) | Leu; Ile; Tyr |
| Phe (F) | Tyr; Met; Leu |
| Pro (P) | Ala |
| Ser (S) | Thr |
| Thr (T) | Ser |
| Trp (W) | Tyr; Phe |
| Tyr (Y) | Trp; Phe |
| Val (V) | Ile; Leu |

"Consists essentially of," and variations such as "consist essentially of" or "consisting essentially of," as used throughout the specification and claims, indicate the inclusion of any recited elements or group of elements, and the optional inclusion of other elements, of similar or different nature than the recited elements, that do not materially change the basic or novel properties of the specified dosage regimen, method, or composition. As a non-limiting example, an anti-RSV antibody that consists essentially of a recited amino acid sequence may also include one or more amino acids, including substitutions of one or more amino acid residues, which do not materially affect the properties of the binding compound.

"Framework region" or "FR" as used herein means immunoglobulin variable regions excluding the CDR regions.

"Kabat" as used herein means an immunoglobulin alignment and numbering system pioneered by Elvin A. Kabat ((1991) Sequences of Proteins of Immunological Interest, 5th Ed. Public Health Service, National Institutes of Health, Bethesda, Md.).

"Anti-RSV antibody" means an antibody or antigen-binding fragment thereof that binds human RSV F protein, preferably from both RSV A strains and B strains, that binds both the pre-fusion F protein and the post-fusion F protein. In some embodiments, the anti-RSV F-protein antibodies are isolated. The antibodies described herein bind to an epitope at site IV of the F protein. In any of the embodiments of the invention described herein, in certain embodiments, the heavy chain or heavy chain variable region does not comprise the amino acid sequence of SEQ ID NO: 9 and/or the light chain or light chain variable region does not comprise the amino acid sequence of SEQ ID NO: 8. In certain embodiments, the heavy chain comprises, consists essentially of, or consists of, the amino acid sequence of SEQ ID NO: 23 and the light chain comprises, consists essentially of, or consists of, the amino acid sequence of SEQ ID NO: 25.

In one embodiment, the anti-RSV F-protein antibodies are fully human.

As used herein, an anti-RSV F-protein antibody or antigen-binding fragment thereof refers to an antibody or antigen-binding fragment thereof that specifically binds to human RSV F protein. An antibody or antigen-binding fragment thereof that "specifically binds to human RSV" is an antibody or antigen-binding fragment thereof that binds to the pre-fusion or post-fusion human RSV F protein with a Kd of about 1 nM or a higher affinity (e.g., 1 nM-2 pM, 1 nM, 100 pM, 10 pM or 2 pM), but does not bind to other proteins lacking RSV F protein sequences. In one embodiment, the antibody of the invention which specifically binds to human RSV F protein is also cross-reactive with bovine RSV F protein. As used herein "cross-reactivity" refers to the ability of an antibody to react with a homologous protein from other species. Whether an antibody specifically binds to human RSV F protein can be determined using any assay known in the art. Examples of assays known in the art to determining binding affinity include surface plasmon resonance (e.g., BIACORE) or a similar technique (e.g., KinExa or OCTET).

In some embodiments of any of the foregoing aspects, the anti-RSV antibody or antigen binding fragment thereof is a "Fab fragment". A "Fab fragment" is comprised of one light chain and the $C_H1$ and variable regions of one heavy chain. The heavy chain of a Fab molecule cannot form a disulfide bond with another heavy chain molecule. A "Fab fragment" can be the product of papain cleavage of an antibody.

In some embodiments of any of the foregoing aspects, the anti-RSV antibody or antigen binding fragment thereof comprises an Fc region. An "Fc" region contains two heavy chain fragments comprising the $C_H1$ and $C_H2$ domains of an antibody. The two heavy chain fragments are held together by two or more disulfide bonds and by hydrophobic interactions of the $C_H3$ domains.

In some embodiments of any of the foregoing aspects, the anti-RSV antibody or antigen binding fragment thereof is a Fab' fragment. A "Fab' fragment" contains one light chain and a portion or fragment of one heavy chain that contains the $V_H$ domain and the $C_H1$ domain and also the region between the $C_H1$ and $C_H2$ domains, such that an interchain disulfide bond can be formed between the two heavy chains of two Fab' fragments to form a F(ab')$_2$ molecule.

In some embodiments of any of the foregoing aspects, the anti-RSV antibody or antigen binding fragment thereof is a F(ab')$_2$ fragment. A "F(ab')$_2$ fragment" contains two light chains and two heavy chains containing a portion of the constant region between the $C_H1$ and $C_H2$ domains, such that an interchain disulfide bond is formed between the two heavy chains. A F(ab')$_2$ fragment thus is composed of two Fab' fragments that are held together by a disulfide bond between the two heavy chains. A "F(ab')$_2$ fragment" can be the product of pepsin cleavage of an antibody.

In some embodiments of any of the foregoing aspects, the anti-RSV antibody or antigen binding fragment thereof is a Fv fragment. The "Fv region" comprises the variable regions from both the heavy and light chains, but lacks the constant regions. In some embodiments of any of the foregoing aspects, the anti-RSV antibody or antigen binding fragment thereof is a scFv fragment. The term "single-chain Fv" or "scFv" antibody refers to antibody fragments comprising the $V_H$ and $V_L$ domains of an antibody, wherein these domains are present in a single polypeptide chain. Generally, the scFv polypeptide further comprises a polypeptide linker between the $V_H$ and $V_L$ domains which enables the scFv to form the desired structure for antigen-binding. For a review of scFv, see Pluckthun (1994) THE PHARMACOLOGY OF MONOCLONAL ANTI- BODIES, vol. 113, Rosenburg and Moore eds. Springer-Verlag, New York, pp. 269-315. See also, International Patent Application Publication No. WO 88/01649 and U.S. Pat. Nos. 4,946,778 and 5,260,203.

In some embodiments of any of the foregoing aspects, the anti-RSV antibody or antigen binding fragment thereof is a domain antibody. A "domain antibody" is an immunologically functional immunoglobulin fragment containing only the variable region of a heavy chain or the variable region of a light chain. In some instances, two or more $V_H$ regions are covalently joined with a peptide linker to create a bivalent domain antibody. The two $V_H$ regions of a bivalent domain antibody may target the same or different antigens.

In some embodiments of any of the foregoing aspects, the anti-RSV antibody or antigen binding fragment thereof is a bivalent antibody. A "bivalent antibody" comprises two antigen-binding sites. In some instances, the two binding sites have the same antigen specificities. However, bivalent antibodies may be bispecific (see below).

In some embodiments of any of the foregoing aspects, the anti-RSV antibody or antigen binding fragment thereof is a diabody. As used herein, the term "diabodies" refers to small antibody fragments with two antigen-binding sites, which fragments comprise a heavy chain variable domain ($V_H$) connected to a light chain variable domain ($V_L$) in the same polypeptide chain ($V_H$-$V_L$ or $V_L$-$V_H$). By using a linker that is too short to allow pairing between the two domains on the same chain, the domains are forced to pair with the complementary domains of another chain and create two antigen-binding sites. Diabodies are described more fully in, e.g., EP 404,097; WO 93/11161; and Holliger et al. (1993) *Proc. Natl. Acad. Sci. USA* 90: 6444-6448. For a review of engineered antibody variants generally see Holliger and Hudson (2005) *Nat. Biotechnol.* 23 :1126-1136.

Typically, an antibody or antigen-binding fragment as described herein which is modified in some way retains at least 10% of its binding activity (when compared to the parental antibody) when that activity is expressed on a molar basis. Preferably, an antibody or antigen-binding fragment retains at least 20%, 50%, 70%, 80%, 90%, 95% or 100% or more of the RSV F-protein binding affinity as the parental antibody. It is also intended that an antibody or antigen-binding fragment can include conservative or non-conservative amino acid substitutions (referred to as "conservative variants" or "function conserved variants" of the antibody) that do not substantially alter its biologic activity.

In some embodiments of any of the foregoing aspects, the anti-RSV antibodys or antigen binding fragments thereof are isolated anti-hRSV F-protein antibodies and antigen-binding fragments thereof. "Isolated" antibodies or antigen-binding fragments thereof are at least partially free of other biological molecules from the cells or cell cultures in which they are produced. Such biological molecules include nucleic acids, proteins, lipids, carbohydrates, or other material such as cellular debris and growth medium. An isolated antibody or antigen-binding fragment may further be at least partially free of expression system components such as biological molecules from a host cell or of the growth medium thereof. Generally, the term "isolated" is not intended to refer to a complete absence of such biological molecules or to an absence of water, buffers, or salts or to components of a pharmaceutical formulation that includes the antibodies or fragments.

In some embodiments of any of the foregoing aspects, the anti-RSV antibodys or antigen binding fragments thereof are monoclonal anti-hRSV F-protein antibodies and antigen-binding fragments thereof. The term "monoclonal antibody" or "mAb" or "Mab", as used herein, refers to a population of substantially homogeneous antibodies, i.e., the antibody molecules comprising the population are identical in amino acid sequence except for possible naturally occurring mutations that may be present in minor amounts. In contrast, conventional (polyclonal) antibody preparations typically include a multitude of different antibodies having different amino acid sequences in their variable domains, particularly their CDRs that are often specific for different epitopes. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al. (1975) *Nature* 256: 495, or may be made by recombinant DNA methods (see, e.g., U.S. Pat. No. 4,816,567). The "monoclonal antibodies" may also be isolated from phage antibody libraries using the techniques described in Clackson et al. (1991) *Nature* 352: 624-628 and Marks et al. (1991) *J. Mol. Biol.* 222: 581-597, for example. See also Presta (2005) *J. Allergy Clin. Immunol.* 116:731.

In one embodiment, the anti-RSV antibody or antigen-binding fragment thereof is Antibody A, comprising two heavy chains of SEQ ID NO: 9 and two light chains of SEQ ID NO: 10.

In one embodiment, the anti-RSV antibody or antigen-binding fragment thereof comprises a heavy chain of SEQ ID NO: 9 and a light chain of SEQ ID NO: 10.

In one embodiment, the anti-RSV antibody or antigen-binding fragment thereof comprises a heavy chain variable region comprising SEQ ID NO: 7 and the light chain variable region comprising SEQ ID NO: 8.

As used herein, the term "hypervariable region" refers to the amino acid residues of an antibody or antigen-binding fragment thereof that are responsible for antigen-binding. The hypervariable region comprises amino acid residues from a "complementarity determining region" or "CDR" (i.e. CDRL1, CDRL2 and CDRL3 in the light chain variable domain and CDRH1, CDRH2 and CDRH3 in the heavy chain variable domain). See Kabat et al. (1991) Sequences of Proteins of Immunological Interest, 5th Ed. Public Health Service, National Institutes of Health, Bethesda, Md. (defining the CDR regions of an antibody by sequence); see also Chothia and Lesk, 1987, *J. Mol. Biol.* 196: 901-917 (defining the CDR regions of an antibody by structure). As used herein, the term "framework" or "FR" residues refers to those variable domain residues other than the hypervariable region residues defined herein as CDR residues.

"Isolated nucleic acid molecule" or "isolated polynucleotide" means a DNA or RNA of genomic, mRNA, cDNA, or synthetic origin or some combination thereof which is not associated with all or a portion of a polynucleotide in which the isolated polynucleotide is found in nature, or is linked to a polynucleotide to which it is not linked in nature. For purposes of this disclosure, it should be understood that "a nucleic acid molecule comprising" a particular nucleotide sequence does not encompass intact chromosomes. Isolated nucleic acid molecules "comprising" specified nucleic acid sequences may include, in addition to the specified sequences, coding sequences for up to ten or even up to twenty or more other proteins or portions or fragments thereof, or may include operably linked regulatory sequences that control expression of the coding region of the recited nucleic acid sequences, and/or may include vector sequences.

A "virus", "viral particle", "virus particle", or "recombinant infectious virus particle" as used herein refers to a single particle derived from a viral nucleic acid, which is located outside a cell. The viral particle thus represents the mature and infectious form of a virus. As the viral particle contains genetic information, it is able to replicate and/or it can be propagated in a susceptible host cell. Depending on the complexity of a virus, the viral particle comprises nucleic acid and polypeptide sequences and, optionally lipids, preferably in the form of a lipid membrane derived from the host cell. A virus having nucleic acid sequences may include genes encoding non-native proteins, called a "genetic payload"

A "polynucleotide sequence", "nucleic acid sequence" or "nucleotide sequence" is a series of nucleotide bases (also called "nucleotides") in a nucleic acid, such as DNA or RNA, and means any chain of two or more nucleotides.

The nucleic acids herein may be flanked by natural regulatory (expression control) sequences, or may be associated with heterologous sequences, including promoters, internal ribosome entry sites (IRES) and other ribosome binding site sequences, enhancers, response elements, suppressors, signal sequences, polyadenylation sequences, introns, 5'- and 3'-non-coding regions, and the like.

A "coding sequence" or a sequence "encoding" an expression product, such as a RNA, polypeptide, protein, or enzyme, is a nucleotide sequence that, when expressed, results in production of the product.

The term "gene" means a DNA sequence that codes for or corresponds to a particular sequence of ribonucleotides or amino acids which comprise all or part of one or more RNA molecules, proteins or enzymes, and may or may not include regulatory DNA sequences, such as promoter sequences, which determine, for example, the conditions under which the gene is expressed. Genes may be transcribed from DNA to RNA which may or may not be translated into an amino acid sequence.

In general, a "promoter" or "promoter sequence" is a DNA regulatory region capable of binding an RNA polymerase in a cell (e.g., directly or through other promoter-bound proteins or substances) and initiating transcription of a coding sequence. A promoter sequence is, in general, bounded at its 3' terminus by the transcription initiation site and extends upstream (5' direction) to include the minimum number of bases or elements necessary to initiate transcription at any level. Within the promoter sequence may be found a transcription initiation site (conveniently defined, for example, by mapping with nuclease S1), as well as protein binding domains (consensus sequences) responsible for the binding of RNA polymerase. The promoter may be operably associated with other expression control sequences, including enhancer and repressor sequences or with a reporter gene.

A coding sequence is "under the control of", "functionally associated with", "operably linked", or "operably associated with" transcriptional and translational control sequences in a cell when the sequences direct RNA polymerase mediated transcription of the coding sequence into RNA, preferably mRNA, which then may be RNA spliced (if it contains introns) and, optionally, translated into a protein encoded by the coding sequence.

The terms "express" and "expression" mean allowing or causing the information in a gene, RNA or DNA sequence to become manifest; for example, producing a protein by activating the cellular functions involved in transcription and translation of a corresponding gene. A DNA sequence is expressed in or by a cell to form an "expression product" such as an RNA (e.g., mRNA) or a protein. The expression product itself may also be said to be "expressed" by the cell.

The term "upstream" refers that the gene is to the 5' end of the other gene.

The term "transformation" means the introduction of a nucleic acid into a cell. The introduced gene or sequence may be called a "clone". A host cell that receives the introduced DNA or RNA has been "transformed" and is a "transformant" or a "clone." The DNA or RNA introduced to a host cell can come from any source, including cells of the same genus or species as the host cell, or from cells of a different genus or species.

A "reporter gene" is a gene encoding a protein that is detectable by fluorescence, luminescence, color change, enzyme assay, or histochemistry. For example, a fluorescent reporter protein encoded by a reporter gene may be a fluorescent protein that fluoresces when exposed to a certain wavelength of light (e.g., GFP). A reporter protein may be a reporter enzyme that catalyzes a reaction with a substrate to produce an observable change in that substrate. Enzymes such as luciferase (exemplary substrate luciferin) or β-lactamase (exemplary substrate CCF4) can cause luminescence or allow fluorescence on substrate cleavage, and enzymes such as β-galactosidase (exemplary substrate X-gal (5-bromo-4-chloro- 3-indolyl-P-D-galactopyranoside)) and secreted alkaline phosphatase (exemplary substrate PNPP (p-Nitrophenyl Phosphate, Disodium Salt)) can result in a visualizable precipitate upon substrate cleavage. The term "luminescent substrate" is a substrate that luminesces upon catalysis by a reporter enzyme, e.g. luciferin. The term "luminescent enzyme" or "luminescent reporter enzyme" refers to an enzyme that catalyzes a reaction with a luminescent substrate. In some embodiments, a reporter protein is detectable by an antibody binding interaction.

The term "luminescent substrate" refers to a substrate that luminesces upon catalysis by a reporter enzyme, e.g. luciferin. The term "luminescent enzyme" or "luminescent reporter enzyme" refers to an enzyme that catalyzes a reaction with a luminescent substrate, e.g. luciferase or nanoluciferase. Various luciferase genes encoding luciferase are commercially available for use in the invention, including luciferase genes from fireflies, sea pansy (*Renilla reniformis*), ostracods (*Cypridina hilgendorfii*), and copepods (*Gaussia princeps*) (see Bioconjug Chem. 2016 May 18; 27(5): 1175-1187, incorporated herein by reference). One luciferase enzyme is NanoLuc® (also called Nluc), a modified 19 kDa luciferase derived from deep sea shrimp (*Oplophorus gracihrostris*) that can be purchased from Promega Corp. Nluc uses the substrate furimazine to produce high intensity, glow-type luminescence when expressed in cells.

The term "fluorescent protein" refers to a protein that emits light at some wavelength after excitation by light at another wavelength. Exemplary fluorescent proteins that emit in the green spectrum range include, but are not limited to: green fluorescent protein (GFP); enhanced GFP (eGFP); superfolder GFP; AcGFP1; and ZsGreen1. Exemplary fluorescent proteins that emit light in the blue spectrum range include, but are not limited to: enhanced blue fluorescent protein (EBFP), EBFP2, Azurite, and mKalama. Exemplary fluorescent proteins that emit light in the cyan spectrum range include, but are not limited to: cyan fluorescent protein (CFP); enhanced CFP (ECFP); Cerulean; mHoneydew; and CyPet. Exemplary fluorescent proteins that emit light in the yellow spectrum range include, but are not limited to: yellow fluorescent protein (YFP); Citrine; Venus; mBanana; ZsYellow 1; and Ypet. Exemplary fluorescent proteins that emit in the orange spectrum range include, but are not limited to: mOrange; tdTomato; Exemplary fluorescent proteins that emit light in the red and far-red spectrum range include, but are not limited to: DsRed; DsRed-monomer; DsRed-Express2; mRFPi; mCherry; mStrawberry; mRaspberry; niPluni; E2-Crimson; iRFP670; iRFP682; iRFP702; iRFP720. Exemplary listings of fluorescent proteins and their characteristics may be found in Day and Davidson, Chem Soc Rev 2009 October; 38(10): 2887-2921, incorporated herein by reference.

Fluorescent proteins may include chimeric combinations of fluorescent proteins that transfer and receive energy through fluorescent resonance energy transfer (FRET) when exposed to a particular wavelength of light. In some embodiments, an acceptor in a FRET pair may emit light at a certain wavelength after accepting energy from a donor molecule exposed to another wavelength of light. Exemplary chimeric FRET pairs, include, but are not limited to ECFP-EYFP; mTurquoise2-SeYFP; EGFP-mCherry; and Clover-mRuby. In some embodiments, the acceptor molecule of chimeric fluorescent molecule may quench the light emission of a donor molecule exposed to its preferred wavelength of light. Quenching between different portions of chimeric fluorescent proteins may occur using a photoactivatable acceptor. For example, a chimeric fluorescent protein may include a photoactivatable GFP that can then quench photoemission by CFP. Examples of FRET proteins are discussed in Ehldebrandt et al., Sensors (Basel). 2016 September; 16(9): 1488, incorporated herein by reference.

"Read-out signal" refers to a signal produced from the reporter gene protein expression. The signal can be emitted by the protein or reaction of the protein with a substrate. In one embodiment, the signal is fluorescence or luminescence.

"Stably transfected" refers to the foreign gene being part of the host genome and is therefore replicated. This is typically initiated by transiently transfecting a cell with the foreign gene but through a process of careful selection and amplification, and stable clones are generated. One method to select for stable clones is to use selectable markers expressed on the plasmid DNA to enable the selection of any cells that have successfully integrated the gene into their genome. A common method used is to design the plasmid DNA to also contain a gene that expresses antibiotic resistance. Continued antibiotic treatment of the cells for long-term results in the expansion of only the stably-transfected cells. Descendants of these stably-transfected cells, also express the foreign gene, resulting in a stably transfected cell line.

The term "vector" includes a vehicle (e.g., a plasmid) by which a DNA or RNA sequence can be introduced into a host cell, so as to transform the host and, optionally, promote expression and/or replication of the introduced sequence.

"Assay media" refers to a solution comprising a nutrient(s) for cells such as glucose, vitamins, amino acids, or a combination thereof and serum, and optionally antibiotics and a buffer.

In some embodiments, the A549 stable cell line is used to test anti-RSV antibodies in an anti-RSV functional cell-based assay. The A549 cell line is a lung epithelial cell line derived from a human carcinoma.

GENERAL METHODS

Standard methods in molecular biology are described in Sambrook, Fritsch and Maniatis (1982 & 1989 2$^{nd}$ Edition, 2001 3$^{rd}$ Edition) *Molecular Cloning, A Laboratory Manual*, Cold Spring Harbor Laboratory Press, Cold Spring Harbor, NY; Sambrook and Russell (2001) *Molecular Cloning, 3$^{rd}$* ed., Cold Spring Harbor Laboratory Press, Cold Spring Harbor, NY; Wu (1993) *Recombinant DNA*, Vol. 217, Academic Press, San Diego, CA). Standard methods also appear in Ausbel, et al. (2001) *Current Protocols in Molecular Biology, Vols.* 1-4, John Wiley and Sons, Inc. New York, NY, which describes cloning in bacterial cells and DNA mutagenesis (Vol. 1), cloning in mammalian cells and yeast (Vol. 2), glycoconjugates and protein expression (Vol. 3), and bioinformatics (Vol. 4).

Methods for protein purification including immunoprecipitation, chromatography, electrophoresis, centrifugation, and crystallization are described (Coligan, et al. (2000) *Current Protocols in Protein Science, Vol.* 1, John Wiley and Sons, Inc., New York). Chemical analysis, chemical modification, post-translational modification, production of fusion proteins, glycosylation of proteins are described (see, e.g., Coligan, et al. (2000) *Current Protocols in Protein Science, Vol.* 2, John Wiley and Sons, Inc., New York; Ausubel, et al. (2001) *Current Protocols in Molecular Biology, Vol.* 3, John Wiley and Sons, Inc., NY, NY, pp. 16.0.5-16.22.17; Sigma-Aldrich, Co. (2001) *Products for Life Science Research*, St. Louis, MO; pp. 45-89; Amersham Pharmacia Biotech (2001) *BioDirectory*, Piscataway, N.J., pp. 384-391). Production, purification, and fragmentation of polyclonal and monoclonal antibodies are described (Coligan, et al. (2001) *Current Protcols in Immunology, Vol.* 1, John Wiley and Sons, Inc., New York; Harlow and Lane (1999) *Using Antibodies*, Cold Spring Harbor Laboratory Press, Cold Spring Harbor, NY; Harlow and Lane, supra). Standard techniques for characterizing ligand/receptor interactions are available (see, e.g., Coligan, et al. (2001) *Current Protocols in Immunology, Vol.* 4, John Wiley, Inc., New York).

Monoclonal, polyclonal, and humanized antibodies can be prepared (see, e.g., Sheperd and Dean (eds.) (2000) *Monoclonal Antibodies*, Oxford Univ. Press, New York, NY; Kontermann and Dubel (eds.) (2001) *Antibody Engineering*, Springer-Verlag, New York; Harlow and Lane (1988) *Antibodies A Laboratory Manual*, Cold Spring Harbor Laboratory Press, Cold Spring Harbor, NY, pp. 139-243; Carpenter, et al. (2000) *J. Immunol.* 165:6205; He, et al. (1998) *J. Immunol.* 160:1029; Tang et al. (1999) J. Biol. Chem. 274:27371-27378; Baca et al. (1997) *J. Biol. Chem.* 272: 10678-10684; Chothia et al. (1989) *Nature* 342:877-883; Foote and Winter (1992) *J. Mol. Biol.* 224:487-499; U.S. Pat. No. 6,329,511).

An alternative to humanization is to use human antibody libraries displayed on phage or human antibody libraries in transgenic mice (Vaughan et al. (1996) *Nature Biotechnol.* 14:309-314; Barbas (1995) *Nature Medicine* 1:837 -839; Mendez et al. (1997) *Nature Genetics* 15:146-156; Hoogenboom and Chames (2000) *Immunol. Today* 21:371-377; Barbas et al. (2001) *Phage Display: A Laboratory Manual*, Cold Spring Harbor Laboratory Press, Cold Spring Harbor, New York; Kay et al. (1996) *Phage Display of Peptides and*

*Proteins: A Laboratory Manual*, Academic Press, San Diego, CA; de Bruin et al. (1999) *Nature Biotechnol.* 17:397-399).

Purification of antigen is not necessary for the generation of antibodies. Animals can be immunized with cells bearing the antigen of interest. Splenocytes can then be isolated from the immunized animals, and the splenocytes can fuse with a myeloma cell line to produce a hybridoma (see, e.g., Meyaard et al. (1997) *Immunity* 7:283-290; Wright et al. (2000) *Immunity* 13:233-242; Preston et al., supra; Kaithamana et al. (1999) *J. Immunol.* 163:5157-5164).

Methods for flow cytometry, including fluorescence activated cell sorting (FACS), are available (see, e.g., Owens, et al. (1994) *Flow Cytometry Principles for Clinical Laboratory Practice*, John Wiley and Sons, Hoboken, NJ; Givan (2001) *Flow Cytometry, 2^{nd}* ed.; Wiley-Liss, Hoboken, NJ; Shapiro (2003) *Practical Flow Cytometry*, John Wiley and Sons, Hoboken, NJ). Fluorescent reagents suitable for modifying nucleic acids, including nucleic acid primers and probes, polypeptides, and antibodies, for use, e.g., as diagnostic reagents, are available (Molecular Probesy (2003) *Catalogue*, Molecular Probes, Inc., Eugene, OR; Sigma-Aldrich (2003) *Catalogue*, St. Louis, MO).

EXAMPLES

Definitions for the abbreviations used herein are provided below.
BSC Biological Safety Cabinet
BSL Bio Safety Level
CDR Complementarity determining region
COA Certificate of Analysis Conc. Concentration
DP Drug Product
DS Drug Substance
ELN Electronic Laboratory Notebook
FBS HI Fetal Bovine Serum, Heat Inactivated
h hour(s)
HC heavy chain
LC light chain
mg Milligram
min/min. Minute(s)
mL Milliliter
No. Number
RPM Revolutions Per Minute
RSV Respiratory Syncytial Virus
RSV-NLucP Respiratory Syncytial Virus-Nanoluc Luciferase-PEST
RT Room Temperature
SDS Safety Data Sheets
SOP Standard Operating Procedure
TC-treated Tissue Culture-Treated
Temp. Temperature
uL/µL Micro liter
WCB Working Cell Bank
WVS Working Virus Seed Equipment used in the examples described here are listed in Table 1 below. Equivalent equipment can also be used.

TABLE 1

| Name | Manufacturer | Model/Part No. |
|---|---|---|
| a. Biological Safety Cabinet, Class II Type A2 | The Baker Company | SterilGARD III |
| b. Humidified $CO_2$ Incubator, 37 ± 1° C., 5 ± 1% $CO_2$ | Thermo Fisher Scientific | Steri-Cult |
| c. Centrifuge with Swing Rotor (for 15- and 50-mL tubes) | Beckman Coulter | Allegra 6R |
| d. Light Inverted Microscope | Zeiss | Invertoskop |
| e. Vi-Cell Automated Cell Counter | Beckman Coulter | Vi-Cell XR |
| f. C-Chip Disposable Hemocytometer (for Manual Cell Counting, optional) | SKC, Inc. | 22-600-107 |
| g. Refrigerator (5 ± 3° C.) | Any Suitable | NA |
| h. Freezer (−20 ± 5° C.) | Any Suitable | NA |
| i. Ultra-Low Freezer (−80 ± 10° C.) | Any Suitable | NA |
| j. Water Bath (37 ± 2° C.) | Thermo Fisher Scientific | Isotemp 210 |
| k. Vortexer | Any Suitable | NA |
| l. Microtiter Plate Shaker | Thermo Fisher Scientific | 4625 |
| m. Wellpro 3000-PG3025 (for serial dilution and reagent transfer, optional) | Wellpro Group | PG3025 |
| n. Viaflo 384 Handheld Electronic 24, 96 and 384 Channel Pipette (for reagent addition or transfer, optional) | Integra | 18030703 |
| o. SpectraMax Plate Reader | Molecular Devices | M5 or M5E |

Consumables and Materials used in the examples are provided in Table 2 below.

TABLE 2

| Name | Manufacturer | Model/Part No. |
|---|---|---|
| a. PET Media Bottle, sterile, 250 mL | Thermo Fisher Scientific | 342040-0250 |
| b. 0.2 µm Nalgene Rapid Flow Sterile Filter Unit with PES Membrane, 500 mL and 1000 mL | Thermo Fisher Scientific | 566-0020 and 567-0020 |

TABLE 2-continued

| Name | Manufacturer | Model/Part No. |
|------|-------------|----------------|
| c. 96-well Polypropylene Round Bottom Microplates with Polystyrene Lids, Sterile | Corning | 3879 |
| d. 96-well white polystyrene CellBind Microplate, sterile, flat bottom clear wells | Corning or PerkinElmer | 3809 (CellBIND) or 6005181 (PerkinElmer) |
| e. 15-mL and 50-mL centrifuge tubes, sterile, polypropylene | Thermo Fisher Scientific | 05-539-12 and 05-539-8 |
| f. 5-mL Macro Centrifuge Tube, Sterile | Argos | T2076S-CA |
| g. Wellpro tips (for serial dilution and reagent transfer, optional) | Wellpro Group | T00802 |
| h. GripTip Pipette Tips, 5 racks of 96 tips, 300 μL low retention sterile tips with filter | Integra | 6535 |
| i. Automation Friendly Reagent Reservoirs, 150 mL & 300 mL sterile polypropylene reservoirs with base and lid | Integra | 6348 (300 mL), 6305 (bases), 6306 (lids), 6338 (150 mL), 6301 (bases), 6302 (lids) |
| j. Vi-Cell sample vials | Beckman Coulter | 723908-D |
| k. Pipette-Aid | Drummond | Any Suitable |
| l. Serological pipettes, sterile | Any suitable | NA |
| m. Single-channel, 8- and 12-channel pipettes | Any suitable | N/A |
| n. Pipette tips with filter | Any suitable | N/A |
| o. Solution reservoirs (100 ml), sterile | Any suitable | N/A |
| p. 50-mL dark polypropylene tubes (for light-sensitive reagents) | CellTreat Scientific or Argos | 229434 (CellTreat Scientific) or TB5000 (Argos) |
| q. Black 96-well assay plate lids (for light-protection of assay plates) | Corning | 3935 |

Reagents used in the examples are provided in Table 3 below.

TABLE 3

| Reagent Name | Manufacturer | Cat. No. |
|--------------|-------------|----------|
| a. A549 working cell bank (WCB), currently qualified lot | Merck | Merck WCB, do not substitute |
| b. RSV-NLucP (RSV-NLP) virus bank (WVS), currently qualified lot | Merck | Merck virus bank, do not substitute |
| c. F-12K Nutrient Mixture | Corning, or equivalent from ATCC, Gibco | 10-025-CV (Corning), 30-2004 (ATCC), 21127-022 (Gibco) |
| d. FBS-HI (Fetal Bovine Serum, heat inactivated) | Sigma or equivalent from Hyclone | F-4135 (Sigma) or SH30071.03 (Hyclone) |
| e. Penicillin-Streptomycin solution (10,000 U/mL) | Gibco | 15140-122 |
| f. Cell Dissociation Buffer (CellStripper or Cell Dissociation Buffer-Enzyme Free) | Corning Inc or Gibco | 25056CI (Corning) or 13151-014 (Gibco) |
| g. PBS, 1X, pH 7.1-7.4 | Thermo Fisher Scientific | 10010-031 |
| h. Trypan Blue 0.4% solution | Thermo Fisher Scientific | 15250-061 |
| i. Nano-Glo ™ Luciferase Assay System | Promega | N1150 |

Standards and Controls

Standards and controls used in the following examples are described as follows. Currently qualified Antibody A Reference Standard lot was used in each assay. Assay control material was drug substance material which is different from the Reference Standard lot. Currently qualified Assay Control lot was used for each dilution plate to ensure the method and related equipment functions as expected.

This method is suitable for testing anti-RSV antibodies such as Antibody A drug substance and drug product release and stability samples, as well as for miscellaneous samples supporting various studies, for example, extended characterization, analytical comparability etc.

Example 1

Generation of RSV-NLucP (RSV-NLP)

The respiratory syncytial virus P3 (RSV-P3) was first used to carry a reporter gene, placing nanoluciferase and luciferase in between the coding sequences for the M and G protein of RSV-P3. However, expression of the reporters was not successful. Insertion of the nanoluciferase reporter gene between the coding sequences for P and M genes of RSV strain A2 was successful, as described below.

The nucleic acid sequence encoding respiratory syncytial virus A2 (RSV-A2) was cloned into a pSMART vector using multiple portions. A gene cassette comprising rpsL flanked by Mlu restriction sites (rpsL-neo selection/counter-selection cassette; pRedET (tc$^R$) plasmid; GeneBridges, Heidelberg, Germany) was cloned into the intergenic sequence between P and M using the following recombineering technique.

Amplification of rpsL Cassette

The rpsL-neo cassette (SEQ ID NO: 11) was PCR amplified using the forward and reverse primers of SEQ ID NO: 12 and 13. PCR amplification with Q5 polymerase (New England BioLabs, Ipswich, MA, USA) used 1-2 ng rpsL-neo pRedET (tc$^R$) plasmid template isolated from Dam+*E. Coli* with the following PCR cycle: 94° C. for 15 sec., 60° C. for 30 sec., 72° C. for 1 min., for 30 cycles. To remove plasmid template methylated by the Dam+*E. Coli*, 1-2 µl DpnI was added per 25 µl reaction, mixed, and incubated at 37° C. for 1 hour. DpnI cleaves the methylated the rpsL plasmid template, but does not cleave the unmethylated PCR products. The DpnI-digested PCR product was gel-purified. A strong PCR band was purified, and eluted in 50 µl ddH$_2$O, and then used to transform electrocompetent SW102 cells (2.5 µl, approximately 10-30 ng).

Insertion of rpsL-neo Cassette into RSV-A2 BAC (Making A2-rpsL BAC)

An overnight culture of SW102 cells containing the RSV-A2 BAC was inoculated in 5 ml LB and chloramphenicol and incubated at 32° C. A portion (500 µl) of the overnight SW102 culture containing the target BAC was diluted in 25 ml LB with chloramphenicol (12.5 mg/ml) in a 50 ml baffled conical flask and incubated at 32° C. in a shaking water bath to an OD600 of approximately. (0.55-0.6), for 3-4 hours. Another portion (10 ml) of the inoculated cells was transferred to another baffled 50 ml conical flask and heat-shocked at 42° C. for exactly 15 minutes in a shaking waterbath. The remaining culture was left at 32° C. as the un-induced control. After 15 minutes, induced and un-induced samples were briefly cooled in an ice/waterbath slurry and then transferred to two 15 ml tubes and pelleted using a centrifuge spun at 5000 RPM at 0° C. for 5 minutes. The supernatant was removed, and the pellet was resuspended in 1 ml ice-cold ddH2O by gently swirling the tubes in the ice/waterbath slurry. When resuspended, another 9 ml ice-cold ddH2O was added and the samples were re-pelleted. The resuspension/re-pelleting step was repeated. After the second washing and centrifugation step, all supernatant was removed by inverting the tubes, and the pellet (approximately 50 ml each) was kept on ice until electroporated with PCR product.

The electrocompetent SW102 cells were then transformed. Each electroporation used 25 µl cells in a 0.1 cm cuvette (BioRad) at 25 mF, 1.75 kV, and 200 ohms. After electroporation of the PCR product, the bacteria were recovered in 1 ml LB (15 ml tube) for 1 hour in a 32° C. shaking waterbath. Following the recovery period, the bacteria were placed on an LB/chloramphenicol+kanamycin agar plate and maintained at 32° C. A clone was picked and checked using colony PCR.

PCR Amplification of Nanoluciferase Cassette (GS-Nlucp-GE Cassette)

A nanoluciferase gene cassette comprising nanoluciferase gene flanked by the gene start (GS) and gene end (GE)

sequences of RSV NS2 (GS-Nlucp-GE; SEQ ID NO: 15) was PCR amplified using the forward and reverse primers of SEQ ID NO: 19 and 20.

PCR amplification with Q5 polymerase (New England BioLabs, Ipswich MA) used 1-2 ng template (a GS-Nlucp-GE plasmid) isolated from Dam+*E. Coli* with the following PCR cycle: 94° C. for 15 sec., 60° C. for 30 sec., 72° C. for 1 min., for 30 cycles. To remove plasmid template methylated by the Dam+*E. Coli*, 1-2 µl DpnI was added per 25 µl reaction, mixed, and incubated at 37° C. for 1 hour. DpnI cleaves the methylated the rpsL plasmid template, but does not cleave the unmethylated PCR products. The DpnI-digested PCR product was purified using Qiagen quick spin columns.

Transform Bacteria with A2-rpsL BAC

Cells containing the A2-rpsL BAC were cultured (20 ml), and DNA was isolated from the cells and eluted in 30 ul water. The A2-rpsL BAC (1 µl) was then used to transform replication competent *E. coli* via electroporation (25 µl of cells in a 0.1 cm cuvette at 25 mF, 1.75 kV and 200 ohms). After electroporation, the bacteria were recovered in 1 ml LB (15 ml tube) for 1 hour in a 32° C. shaking waterbath. After the recovery period the bacteria were placed on an LB/chloramphenicol+kanamycin agar plate and maintained at 32° C.

Gibson Assembly to Replace the rpsL Cassette with GS-Nlucp-GE Cassette

The A2-rpsL BAC-transformed bacteria were cultured to a volume of 200 ml in LB+chloramphenicol+0.01% arabinose. The A2-rpsL BAC was then purified using the BAC-MAX™ DNA Purification Kit (Cambio, Cambridge, UK).

The purified A2-rpsL BAC was digested using 1 µl DpnI to digest the template DNA at 37° C. for 1 hour, and the PCR products were cleaned using Qiaquick PCR Purification Kit (Qiagen, Hilden, Germany).

Assembly product was mixed using purified A2-rpsL BAC fragment (Mlu I digestion; 9 ul), GS-Nlucp-GE cassette PCR product (1:20 dilution; 1 µl), ddH$_2$O (8 µl), and Gibson Assembly Master Mix (2×) (10 µl). Assembly product was warmed to 50° C. for 15 minutes, then chilled.

Competent cells were thawed on ice, and 20 µl of the chilled assembly product were added to the competent cells, mixing gently. The mixture was placed on ice for 30 minutes, then heat shocked at 42° C. for 30 seconds. Tubes were then transferred to ice for 2 minutes, and 500 µl of room-temperature SOC media was added to the tube. The tube was incubated at 37° C. for 60 minutes, then shaken vigorously (250 rpm) or rotated. The cells (100 µl) were then spread on warmed selection plates (37° C.) and incubated overnight at 37° C.

Two colonies from each of two positive plates were picked, inoculated in 5 ml LB with chloramphenicol and grown overnight with shaking. Colony PCR was used to amplify product using forward and reverse primers for nanolucP (SEQ ID NO: 19 and 20, respectively). PCR cycle initial denaturation 98° C. for 2 minutes, followed by 35 Cycles of : 98° C. for 10 seconds, 52° C. for 30 seconds, and 72° C. for 2 minutes 30 seconds. Final extension was 72° C. for 2 minutes.

The resulting plasmid pSMART RS A2 NLucP is listed in SEQ ID NO: 21.

Example 2

Viral Rescue

Initial Cell Culture

For transfections, BSR T7/5 cells from "donor" cultures were subpassed into 6 well plates to be 80-90% confluent at time of transfection. One 25 cm² culture was used to prepare one 6 well plate (1:2.5 passage ratio) (or 2 ml of 4e5 cells/ml).

Six-well cell culture plates were prepared for transfection from 25 cm² donor cultures. Growth medium was aspirated from the flasks, and then 0.25 mL of warm trypsin-EDTA was added per 25 cm² flask. Flasks were shaken to distribute the trypsin-EDTA and incubated at 37° C. for 5 to 10 minutes. When cells started to dislodge from the flask, 12 mL of medium was added to each flask, and the cells were suspended by pipetting. Two mL of the cell suspension were added to each well in the 6-well cell culture plates. The cell culture plates were incubated at 37° C. in the tissue culture incubator overnight.

Reagent Preparation for Transfection

Lipofectamine and plasmid/helper plasmid were mixed in a 3:1 ratio (μL/μg), as well as lipofectamine-only and wild type virus-only controls. Each component was diluted with Opti-MEM to make 100 μL of lipofectamine/plasmid/helper plasmid (3:1), lipofectamine-only control, and wild-type virus-only control. Each dilution was incubated at room temperature for 5 minutes.

After incubating the diluted lipofectamine/plasmid/helper plasmid and controls, the following six components were combined in one vial, mixed gently. and incubate the transfection mixture at room temperature for 20 minutes (transfection mixtures should be 600 μL total, Opti-MEM, Lipofectin, and DNA).

The following amounts of each component was used per transfection:
  i. RSV antigenome 0.8 μg (8 μL of 0.1 μg/μL)+92 μL Opti-MEM
  ii. pCDNA3-L, L protein 0.2 μg (2 μL of 0.1 μg/μL)+98 μL Opti-MEM
  iii. pCDNA3-N, N protein 0.4 μg (4 μL of 0.1 μg/μL)+96 μL Opti-MEM
  iv. pCDNA3-P, P protein 0.4 μg (4 μL of 0.1 μg/μL)+96 μL Opti-MEM
  v. pCDNA3-M2-1, M2-1 protein 0.4 μg (4 μL of 0.1 μg/μL)+96 μL Opti-MEM
  vi. Lipofectamine 2000 6.6 μL+93.4 μL Opti-MEM Cell Transfection The media from the B SR T7/5 cell culture wells was aspirated, and cells were washed twice with 1 mL warm Opti-MEM. After the final wash was aspirated, 600 μL of the transfection mixtures was added to each culture well, and the cultured cells were incubated for 2 hours at room temperature on a shaker/rocker plate set at low speed. After 2 hours, an additional 600 μL warm Opti-MEM was added per well and incubated at 37° C. overnight (8-12 hours).

After incubation, the transfection mixture was aspirated from the wells and discarded, and each well was washed once with 1 mL warm sterile PBS and replaced with 2 mL of warm growth medium per well. Cultured cells were then incubated at 37° C. overnight.

The cells were then sub-passaged at a 1:3 surface area ratio into 25 cm² flasks using the trypsin-EDTA procedure described above. If the cell morphology appeared weak, the surface area ratio was decreased accordingly up to an even 1:1 ratio (surface area of each well in the 6 well plates is 10 cm²). Cells remained in DMEM with 3% FBS while recovering recovery. Flasks were monitored for cytopathic effect (CPE) and sub-passaged at a 1:3 surface area ratio into new 25 cm² flasks as needed (approximately every 48 hours). CPE appeared first as mini-syncytia and then grew into rounded up clumps of cells. When CPE was evident throughout the flask, the cells were scraped into the growth media, aliquoted into cryovials, and frozen at −80° C. or colder.

Example 3

Preparation of In-Lab Reagents a) A549 Growth Medium Preparation

TABLE 4

| A549 Growth Medium (Note: volumes may be scaled up or down proportionally) | | | | |
|---|---|---|---|---|
| Reagent | Final Conc. (%) | Amount (mL) | Storage Temp. (° C.) | Storage Time |
| F-12K nutrient mixture | 89 | 445 | 5 ± 3 | 1 month |
| FBS HI* | 10 | 50 | | |
| Pen/Strep (10,000 U/mL) | 1 | 5 | | |

*FBS is aliquoted for single use and stored at −20° C.

Table 4 components were added to make up 500 mL of A549 cell growth medium. A549 cell growth medium was sterile filtered through a 0.2 micron 500-mL (or other appropriate volume) PES filtering unit.

b) A549 Infection Medium Preparation

TABLE 5

| A549 Infection Medium (Note: volumes may be scaled up or down proportionally) | | | | |
|---|---|---|---|---|
| Reagent | Final Conc. (%) | Amount (mL) | Storage Temp. (° C.) | Storage Time |
| F-12K nutrient mixture | 97 | 485 | 5 ± 3 | 1 month |
| FBS HI* | 2 | 10 | | |
| Pen/Strep (10,000 U/mL) | 1 | 5 | | |

*FBS is aliquoted for single use and stored at −20° C.

Table 5 components were added to make up 500 mL of A549 infection medium. A549 infection medium was sterile-filtered through a 0.2 micron 500-mL (or other appropriate volume) PES filtering unit.

Example 4

Procedures for Preparing Testing Samples and Measuring Read-Out Signals

Procedures for preparing testing samples and measuring read-out signals are shown in FIG. 1. Detailed procedures are provided below.

Day 1: Cell Seeding

A549 growth medium was equilibrated to RT, about 30 minutes. Growth medium was aspirated, and cells were washed with 15 mL of PBS with rocking to ensure the entire monolayer was coated. After the PBS was aspirated, 5 mL of cell dissociation buffer solution was added with 15 rocking to ensure the entire monolayer is coated. Each flask was incubated with humidity at 37±1° C., 5±1% $CO_2$ until cells dislodged from flask (about 10-15 min). Each flask was tapped to disperse the cells.

20 mL of A549 growth medium was added to each flask, and all flask contents were transferred into a single sterile container. The cell suspension was mixed with a serological pipette by slowly pipetting 4-5 times until no clumps were visible. Cells were then counted, either manually or using Vi-Cell. Cell were then suspended in A549 growth medium at $2\times10^5$ cells/mL in a sterile PET bottle or equivalent container.

The 100 µl cell suspension was dispensed into 96-well plates (100 µl per well, about 20,000 cells per well), and incubated on a flat surface at RT for 35±5 minutes to ensure that cells homogenously settle dat the bottom of the 96-well plates. Seeded plates were incubated in humidity at 37±1° C., 5±1% $CO_2$ incubator for 20-26 h.

Day 2: Sample Dilution, Virus Neutralization and Infection

Preparations of Standards, Assay Control and Test Samples

All dilutions are prepared in BSC class II. Thoroughly mix each dilution by vortexing or pipetting during preparation. For each assay plate, dilutions of Antibody A are performed in singleton and tested in duplicate (i.e., each assay dilution is loaded into 2 wells) on each plate. Volumes in the following tables can be scaled up proportionally.

Antibody A Reference Standard was diluted in A549 Infection Medium to 16 µg/mL.

TABLE 6

| | Example dilution scheme (if Reference Standard concentration is 101.4 mg/mL): | | | |
|---|---|---|---|---|
| Step | Starting Conc. (µg/mL) | Volume of Starting Material (µL) | Volume of Infection Medium (µL) | Target Conc. (µg/mL) |
| 1 | 101,400 | 20 | 2515 | 800 |
| 2 | 800 | 40 | 1960 | 16 |

Dilute Antibody A Assay Control was diluted in A549 Infection Medium to 16 µg/mL.

TABLE 7

| | Example dilution scheme (if Assay Control concentration is 101.4 mg/mL) | | | |
|---|---|---|---|---|
| Step | Starting Conc. (µg/mL) | Volume of Starting Material (µL) | Volume of Infection Medium (µL) | Target Conc. (µg/mL) |
| 1 | 101,400 | 20 | 2515 | 800 |
| 2 | 800 | 40 | 1960 | 16 |

TABLE 8

| | Example dilution scheme (if Assay Control concentration is 150 mg/mL) | | | |
|---|---|---|---|---|
| Step | Starting Conc. (µg/mL) | Volume of Starting Material (µL) | Volume of Infection Medium (µL) | Target Conc. (µg/mL) |
| 1 | 150,000 | 20 | 2480 | 1200 |
| 2 | 1200 | 40 | 2960 | 16 |

Antibody A Test Sample(s) was diluted in A549 Infection Medium to 16 µg/mL.

TABLE 9

| | Example dilution scheme (if Test Sample concentration is 100 mg/mL) | | | |
|---|---|---|---|---|
| Step | Starting Conc. (µg/mL) | Volume of Starting Material (µL) | Volume of Infection Medium (µL) | Target Conc. (µg/mL) |
| 1 | 100,000 | 20 | 2480 | 800 |
| 2 | 800 | 40 | 1960 | 16 |

TABLE 10

| | Example dilution scheme (if Test Sample concentration is 150 mg/mL) | | | |
|---|---|---|---|---|
| Step | Starting Conc. (µg/mL) | Volume of Starting Material (µL) | Volume of Infection Medium (µL) | Target Conc. (µg/mL) |
| 1 | 150,000 | 20 | 2480 | 1200 |
| 2 | 1200 | 40 | 2960 | 16 |

Set Up Dilution Plates

Dilution plate maps for plates 1-3 are shown in FIGS. 2A, 2B and 2C. Detailed procedures are described below.

Infection medium (90 µL) was dispensed into wells of a dilution plate, followed by 120 µL of dilutions of Antibody A Reference Standard, Assay Control, and Testing Sample in duplicate into dilution plate wells according to the dilution Plate Maps shown in FIGS. 2A-2C. Four-fold serial dilutions were performed by transfering 30 µL to next column, from column 1 through column 11.

Virus Neutralization

Frozen RSV-NLucP was quickly thawed in 37° C. water bath with gentle agitation until a small portion of ice remained. Once virus was completely thawed, the vial surface was cleaned and wiped with approved disinfectant and the vial was transferred to a Biological Safety Cabinet (BSC).

The desired volume of virus dilution was prepared as shown in table 11.

TABLE 11

| Example virus dilution for 1-3 assay plates | | | | | |
|---|---|---|---|---|---|
| Number of plates | Virus | Dilution | Virus stock (mL) | Infection Medium (mL) | Total volume (mL) |
| 1 | RSV-NLucP WVS | 1:40 | 0.4 | 15.6 | 16 |
| 2 | RSV-NLucP WVS | 1:40 | 0.6 | 23.4 | 24 |
| 3 | RSV-NLucP WVS | 1:40 | 0.9 | 35.1 | 36 |

Note:
Virus dilution factor may be adjusted as an outcome of new lot qualification.

Diluted virus (90 μl) was added to each well of column 11-1 by column (from column 11 backward to column 1) of each plate. Infection medium (90 μl) was added to column-12 row B-D wells (Cell Control). Diluted virus (90 μl) was added to column-12 row E-G wells (Virus Control). Infection medium (180 μl) was added to row A and row H wells. The plate was incubated with 150-200 rpm shaking for 2 minutes, then incubated with humidity at $37\pm1°$ C., $5\pm1\%$ $CO_2$ incubator for $35\pm5$ min (Neutralization). The virus neutralization time of each plate was documented.

Infection

After incubation, cell plates were examined under a microscope to ensure that the cells were 70%-100% confluent and free of any contamination. The cell plates were equilibrated to RT for 10-15 min in a BSC, and then culture medium was decanted into a waste container and gently tapped upside-down on an absorbent towel to remove residual medium. Virus-sample mixture (90 μL) was transferred to the corresponding wells in each cell culture plate by row (Row A through Row H). Plates were then incubated in humidity at $37\pm1°$ C., $5\pm1\%$ $CO_2$ for $21\pm1$ h. The inoculation time of each plate was documented.

Day 3: Detection of Infected Cell Plates with Nano-Glo® Reagent

After $21\pm1$ h post infection, the cell plates were equilibrated for 10-15 min at RT. Nano-Glo® reagent was prepared and reconstituted according to manufacturer instructions, and then added to the wells of the cell plate. Cell plates were protected from light, and incubated on a shaker (200 rpm) for 10-15 min at RT, document Following incubation, plates were read using a Spectramax M5 or M5e Plate Reader as listed in Table 12 below.

TABLE 12

| Settings for SpectraMax M5 or M5e Plate Reader Instrument | |
|---|---|
| Parameter | Setting |
| Read Mode | Luminescence |
| | Integration: 500 ms |
| | Top read |
| Read Type | Endpoint |
| Wavelengths | Lm1 |
| | Em: All |
| Assay Plate Type Plate | 96-well Polystyrene Clear Flat Bottom Microplate |
| Read Area | Read entire plate |
| Shake | OFF |
| Calibrate | On |
| Carriage Speed | Normal |
| Read Priority | Column Priority |

System Suitability Requirements

System suitability was evaluated in each cell plate of the assay run. The Reference Standard and the Assay Control should meet all Assay Acceptance Criteria in Table 13. Failing system suitability requirements disqualified all sample testing results on that cell plate.

Data Acquisition

Raw data containing relative luminescence units (RLU) counts was captured using SoftMax Pro software.

Calculations

The potency of the Testing Sample relative to the Reference Standard (relative potency) was calculated instead of relying on four-parameter logistic regression. Calculating relative potency allows for reducing the amount of duplicated wells and fewer antibody concentrations to be tested. In turn, this allows room in the assay wells for adding not only the reference standard wells, but also Assay Control wells to confirm assay quality.

The mean relative luminescent units (RLU) were plotted as a function of Antibody A concentration to generate sigmoidal dose-response curves. The data were fit to four-parameter logistic (4 PL) equation:

$$y = D + \frac{A - D}{1 + \left(\frac{x}{C}\right)^B}$$

where y is the mean luminescence signal, D is the lower asymptote, A is the upper asymptote, x is the Antibody A concentration (ng/mL), C is the inflection point or $IC_{50}$ (ng/mL), and B is the slope parameter of the 4PL curve fit. Raw data was fitted for each individual test article (i.e., Reference, Control, and Samples) independently of each other (e.g. an unrestricted fit), from which parameters A, B, C, and D for each individual dose-response curve were calculated and recorded.

Determined A and D parameters were used to calculate the relative percentage difference of the upper asymptotes (% A Difference) and the relative percentage difference of the lower asymptotes (% D difference) between Reference and Test samples (or Control) using the following formulas:

$$\% \; A \; \text{Difference} = \left| \frac{|A_{Reference} - A_{Sample \, (or \, Control)}|}{A_{Reference} - D_{Reference}} \right| \times 100$$

$$\% \; D \; \text{Difference} = \left| \frac{|D_{Reference} - D_{Sample \, (or \, Control)}|}{A_{Reference} - D_{Reference}} \right| \times 100$$

Determined B (Slope) parameters were used in calculation of Slopes Ratio using the following equation:

$$\text{Slope Ratio} = \frac{B_{Reference}}{B_{Sample \, (or \, Control)}}$$

A and D parameters calculated for Reference Standard are used to calculate the ratio of the asymptotes as follows:

$$\text{Asymptotes Ratio}_{Reference} = \frac{A_{Reference}}{D_{Reference}}$$

Sum of Squared Errors (SSE) evaluates goodness of fit statistics and measures the total deviation of the observed response values (experimental) from the fitted data (predicted).

$$SSE = \sum_{i=1}^{n}(y_i - f_i)^2$$

where n is the number of observations (equals to 11 as per the total number of concentration points), $y_i$ is the observed data value and $f_i$ is the predicted value from the fit. SSE was determined based on normalized data to account for possible differences in absolute signal intensity between different instruments.

After the unrestricted analysis, the raw data were fit to a restricted 4PL fit, where Reference curve was analyzed as paired with each individual sample (or control) on the plate, i.e., Reference vs. Sample 1, or Reference vs. Sample 2, or Reference vs. Sample 3, or Reference vs. Assay Control. Both curves in the pair were fit to the same parameter A, the same parameter D, and the same parameter B, allowing only parameter C to fluctuate for the best fit (e.g. Parallel Line Analysis; PLA). PLA results were presented for each pair on a separate graph.

By fitting a pair of curves using PLA analysis, potency of test sample or control was calculated using following equation:

$$\text{Relative Potency } (\%)_{Sample(or\ Control)} = \frac{C_{Reference}}{C_{Sample(or\ Control)}} \times 100$$

Reportable Potency result as geometric mean (GeoMean) of three relative potency values was calculated using the following equation:

$$\text{GeoMean } (\%) = 10^{Mean(Log10\ potency)}$$

where Mean (Log10 potency) is the average of decimal logarithm values of three Relative Potency values calculated in Section 6.2.0.

Variability of the Reportable Potency as geometric standard deviation (% GSD) of three relative potency values using the following equation:

$$\% \ GSD = 100 \times (10^{St.Dev.(Log10\ potency)} - 1)$$

where St.Dev.(Log10 potency) is standard deviation of decimal logarithm values of three Relative Potency values. If not all 3 plates passed acceptance criteria, the sample testing was repeated according to the Valid Test Acceptance Criteria (see below).

Valid Test Acceptance Criteria

TABLE 13

| Assay Acceptance Criteria (for each assay plate): | | |
|---|---|---|
| Assay Article ID | Assay Acceptance Parameter | Acceptance Criteria |
| Reference Standard | Asymptotes ratio | ≥3.0 |
| | SSE of normalized curve fit | ≤0.5 |
| Assay Control | SSE of normalized curve fit | ≤0.5 |
| | % A Difference vs. Reference Standard Curve | ≤25% |
| | % D Difference vs. Reference Standard Curve | ≤15% |
| | Ratio of Slopes vs. Reference Standard Curve | 0.5-2.0 |
| | Relative potency (%) | 50-200 |

Assay Control material is described above (Standards and Controls). Acceptance criteria may be reassessed later when more data are available. If any of the assay acceptance criteria failed, all sample data from that plate was rejected, and the failed plate was re-measured.

TABLE 14

| Sample Acceptance Criteria (for each assay plate) | | |
|---|---|---|
| Test Article ID | Sample Acceptance Parameter | Acceptance Criteria |
| Test Sample | SSE of normalized curve fit | ≤0.5 |
| | % A Difference vs. Reference Standard Curve | ≤25% |
| | % D Difference vs. Reference Standard Curve | ≤15% |
| | Ratio of Slopes vs. Reference Standard Curve | 0.5-2.0 |
| | Relative potency (%) | Per Qualified Range |

If any of the sample acceptance criteria failed for a particular sample, that sample data was rejected, and the failed sample was re-measured. During the re-measured test, sample position on repeat plate was the same as on the original plate.

Acceptance Criteria for Validity of Geometrical Mean Relative Potency (Reportable Result)

The % GSD of the three valid relative potency values was ≤50%. If % GSD>50%, all of the data was evaluated, and results were compared between all three valid plates. If, upon evaluation, atypical results were identified, those plate(s) were invalidated and repeated while maintaining the same plate number(s) and sample positions as in the original plate(s). If no atypical behavior was identified in any of the plates, all three plates were invalidated and repeated.

Reporting Test Results

If all valid acceptance criteria listed in Tables 13 and 14 were successfully met, and the % GSD of the three valid relative potency values was ≤50%, the Geometric Mean of three relative potency values rounded to the same number of decimals was reported.

Relative potency of a test sample is expressed as a percentage relative to concurrently analyzed Antibody A reference standard. The reportable value of potency of Antibody A test sample was calculated as geometric mean of three relative potency determinations obtained from three independently handled assay plates.

TABLE 15

Table of Sequences

| SEQ ID NO: | Description | Sequence |
|---|---|---|
| 1 | Antibody A HC-CDR1 | DSAMS |
| 2 | Antibody A HC-CDR2 | FIKSKTYGGTKEYAASVKG |
| 3 | Antibody A HC-CDR3 | GAPYGGNSDYYYGLDV |
| 4 | Antibody A LC-CDR1 | RTSQDVRGALA |
| 5 | Antibody A LC-CDR2 | DASSLET |
| 6 | Antibody A LC-CDR3 | QQFLDFPFT |
| 7 | Antibody A $V_H$ | EVQLVESGGGLVRPGRSLRLSCTVSGFSFDDSAMSWVRQAPGKGLE WISFIKSKTYGGTKEYAASVKGRFTISRDDSKNIAYLQMNSLKTED TAVYYCTRGAPYGGNSDYYYGLDVWGQGTTVTVSS |
| 8 | Antibody A $V_L$ | EVQLVESGGGLVRPGRSLRLSCTVSGFSFDDSAMSWVRQAPGKGLE WISFIKSKTYGGTKEYAASVKGRFTISRDDSKNIAYLQMNSLKTED TAVYYCTRGAPYGGNSDYYYGLDVWGQGTTVIVSS |
| 9 | Antibody A Heavy chain | EVQLVESGGGLVRPGRSLRLSCTVSGFSFDDSAMSWVRQAPGKGLE WISFIKSKTYGGTKEYAASVKGRFTISRDDSKNIAYLQMNSLKTED TAVYYCTRGAPYGGNSDYYYGLDVWGQGTTVTVSSASTKGPSVFPL APSSKSTSGGTAALGCLVKDYFPEPVTVSWNSGALTSGVHTFPAVL QSSGLYSLSSVVTVPSSSLGTQTYICNVNHKPSNTKVDKKVEPKSC DKTHTCPPCPAPELLGGPSVFLFPPKPKDTLYITREPEVTCVVVDV SHEDPEVKFNWYVDGVEVHNAKTKPREEQYNSTYRVVSVLTVLHQD WLNGKEYKCKVSNKALPAPIEKTISKAKGQPREPQVYTLPPSRDEL TKNQVSLTCLVKGFYPSDIAVEWESNGQPENNYKTTPPVLDSDGSF FLYSKLTVDKSRWQQGNVFSCSVMHEALHNHYTQKSLSLSPGK |
| 10 | Antibody A Light chain | DIQMTQSPSSLSASVGDRVTITCRTSQDVRGALAWYQQKPGKAPKL LIFDASSLETGVPSRFSGSGSGTVFTLTISSLQPEDFAAYYCQQFL DFPFTFGQGTRLEIKRTVAAPSVFIFPPSDEQLKSGTASVVCLLNN FYPREAKVQWKVDNALQSGNSQESVTEQDSKDSTYSLSSTLTLSKA DYEKHKVYACEVTHQGLSSPVTKSENRGEC |
| 11 | rpsL-neo cassette Promoter: nt 1-138 rpsL CDS: 139-513 Neomycin/ kanamycin CDS: 525-2638 | ggcctggtgatgatggcgggatcgttgtatatttcttgacaccttt tcggcatcgccctaaaattcggcgtcctcatattgtgtgaggacgt tttattacgtgtttacgaagcaaaagctaaaaccaggagctattta atggcaacagttaaccagctggtacgcaaaccacgtgctcgcaaag ttgcgaaaagcaacgtgcctgcgctggaagcatgcccgcaaaaacg tggcgtatgtactcgtgtatatactaccactcctaaaaaaaccgaac tccgcgctgcgtaaagtatgccgtgttcgtctgactaacggtttcg aagtgacttcctacatcggtggtgaaggtcacaacctgcaggagca ctccgtgatcctgatccgtggcggtcgtgttaaagacctcccgggt gttcgttaccacaccgtacgtggtgcgcttgactgctccggcgtta aagaccgtaagcaggctcgttccaagtatggcgtgaagcgtcctaa ggcttaaggaggacaatcatgattgaacaagatggattgcacgcag gttctccggccgcttgggtggagaggctattcggctatgactgggc acaacagacaatcggctgctctgatgccgccgtgttccggctgtca gcgcaggggcgcccggttctttttgtcaagaccgacctgtccggtg ccctgaatgaactgcaggacgaggcagcgcggctatcgtggctggc cacgacgggcgttccttgcgcagctgtgctcgacgttgtcactgaa gcgggaagggactggctgctattgggcgaagtgccggggcaggatc tcctgtcatctcaccttgctcctgccgagaaagtatccatcatggc tgatgcaatgcggcggctgcatacgcttgatccggctacctgccca ttcgaccaccaagcgaaacatcgcatcgagcgagcacgtactcgga tggaagccggtcttgtcgatcaggatgatctggacgaagagcatca ggggctcgcgccagccgaactgttcgccaggctcaaggcgcgcatg cccgacggcgaggatctcgtcgtgacccatggcgatgcctgcttgc cgaatatcatggtggaaaatggccgcttttctggattcatcgactg tggccggctgggtgtggcggaccgctatcaggacatagcgttggct acccgtgatattgctgaagagcttggcggcgaatgggctgaccgct tcctcgtgctttacggtatcgccgctcccgattcgcagcgcatcgc cttctatcgccttcttgacgagttcttctga |

TABLE 15-continued

| Table of Sequences | | |
|---|---|---|
| SEQ ID NO: | Description | Sequence |
| 12 | Forward primer for rpsL cassette | CTTCGTGAAGCTTGTTCACGTATGTTTCCATATTTGCCCCACCCTA cgcgtGGCCTGGTGATGATGGCGGGATCG |
| 13 | Reverse primer for rpsL cassette | CTAACCACCCGGAAAAAATCTATAATATAGTTACAAAAAAAGGAAa cgcgTCAGAAGAACTCGTCAAGAAGG |
| 14 | RSV A2 NS1 CDS: nt 76-492 NS2 CDS: nt 9605-76 N CDS: nt 1117-2289 P CDS: 2323-3045 M CDS: 3238-4005 SH CDS: 4280-4471 G CDS: 4665-5558 F CDS: 5638-7359 M2-1 CDS: 7583-8164 M2-2 CDS: 8136-8405 L CDS: 8475-14,969 | ACTTGCATAAACCAAAAAAATGGGGCAAATAAGAATTTGATAAGTA CCACTTAAATTTAACTCCCTTGGTTAGAGATGGGCAGCAATTCATT GAGTATGATAAAAGTTAGATTACAAAATTTGTTTGACAATGATGAA GTAGCATTGTTAAAAATAACATGCTATACTGATAAATTAATACATT TAACTAACGCTTTGGCTAAGGCAGTGATACATACAATCAAATTGAA TGGCATTGTGTTTGTGCATGTTATTACAAGTAGTGATATTTGCCCT AATAATAATATTGTAGTAAAATCCAATTTCACAACAATGCCAGTAC TACAAAATGGAGGTTATATATGGGAAATGATGGAATTAACACATTG CTCTCAACCTAATGGTCTACTAGATGACAATTGTGAAATTAAATTC TCCAAAAAACTAAGTGATTCAACAATGACCAATTATATGAATCAAT TATCTGAATTACTTGGATTTGATCTTAATCCATAAATTATAATTAA TATCAACTAGCAAATCAATGTCACTAACACCATTAGTTAATATAAA ACTTAACAGAAGACAAAAATGGGGCAAATAAATCAATTCAGCCAAC CCAACCATGGACACAACCCACAATGATAATACACCACAAAGACTGA TGATCACAGACATGAGACCGTTGTCACTTGAGACCATAATAACATC ACTAACCAGAGACATCATAACACACAAATTTATATACTTGATAAAT CATGAATGCATAGTGAGAAAACTTGATGAAAAACAGGCCACATTTA CATTCCTGGTCAACTATGAAACTATTACACAAAGTAGGAAG CACTAAATATAAAAAAATATACTGAATACAACACAAAATATGGCACT TTCCCTATGCCAATATTCATCAATCATGATGGGTTCTTAGAATGCA TTGGCATTAAGCCTACAAAGCATACTCCCATAATATACAAGTATGA TCTCAATCCATAAATTTCAACACAATATTCACACAATCTAAAACAA CAACTCTATGCATAACTATACTCCATAGTCCAGATGGAGCCTGAAA ATTATAGTAATTTAAAATTAAGGAGAGATATAAGATAGAAGATGGG GCAAATACAAAGATGGCTCTTAGCAAAGTCAAGTTGAATGATACAC TCAACAAAGATCAACTTCTGTCATCCAGCAAATACACCATCCAACG GAGCACAGGAGATAGTATTGATACTCCTAATTATGATGTGCAGAAA CACATCAATAAGTTATGTGGCATGTTATTAATCACAGAAGATGCTA ATCATAAATTCACTGGGTTAATAGGTATGTTATATGCGATGTCTAG GTTAGGAAGAGAAGACACCATAAAAATACTCAGAGATGCGGGATAT CATGTAAAAGCAAATGGAGTAGATGTAACAACACATCGTCAAGACA TTAATGGAAAAGAAATGAAATTTGAAGTGTTAACATTGGCAAGCTT AACAACTGAAATTCAAATCAACATTGAGATAGAATCTAGAAAATCC TACAAAAAAATGCTAAAAGAAATGGGAGAGGTAGCTCCAGAATACA GGCATGACTCTCCTGATTGTGGGATGATAATATTATGTATAGCAGC ATTAGTAATAACTAAATTAGCAGCAGGGGACAGATCTGGTCTTACA GCCGTGATTAGGAGAGCTAATAATGTCCTAAAAAATGAAATGAAAC GTTACAAAGGCTTACTACCCAAGGACATAGCCAACAGCTTCTATGA AGTGTTTGAAAAACATCCCCACTTTATAGATGTTTTTGTTCATTTT GGTATAGCACAATCTTCTACCAGAGGTGGCAGTAGAGTTGAAGGGA TTTTTGCAGGATTGTTTATGAATGCCTATGGTGCAGGGCAAGTGAT GTTACGGTGGGGAGTCTTAGCAAAATCAGTTAAAAATATTATGTTA GGACATGCTAGTGTGCAAGCAGAAATGGAACAAGTTGTTGAGGTTT ATGAATATGCCCAAAAATTGGGTGGTGAAGCAGGATTCTACCATAT ATTGAACAACCCAAAAGCATCATTATTATCTTTGACTCAATTTCCT CACTTCTCCAGTGTAGTATTAGGCAATGCTGCTGGCCTAGGCATAA TGGGAGAGTACAGAGGTACACCGAGGAATCAAGATCTATATGATGC AGCAAAGGCATATGCTGAACAACTCAAAGAAAATGGTGTGATTAAC TACAGTGTACTAGACTTGACAGCAGAAGAACTAGAGGCTATCAAAC ATCAGCTTAATCCAAAAGATAATGATGTAGAGCTTTGAGTTAATAA AAAATGGGGCAAATAAATCATCATGGAAAAGTTTGCTCCTGAATTC CATGGAGAAGATGCAAACAACAGGGCTACTAAATTCCTAGAATCAA TAAAGGGCAAATTCACATCACCCAAAGATCCCAAGAAAAAGATAG TATCATATCTGTCAACTAATAGATATAGAAGTAACCAAAGAAAGC CCTATAACATCAAATTCAACTATTATCAACCCAACAAATGAGACAG ATGATACTGCAGGGAACAAGCCCAATTATCAAAGAAAACCTCTAGT AAGTTTCAAAGAAGACCCTACACCAAGTGATAATCCCTTTTCTAAA CTATACAAAGAAACCATAGAAACATTTGATAACAATGAAGAAGAAT CCAGCTATTCATACGAAGAAATAAATGATCAGACAAACGATAATAT AACAGCAAGATTAGATAGGATTGATGAAAAATTAAGTGAAATACTA GGAATGCTTCACACATTAGTAGTGGCAAGTGCAGGACCTACATCTG CTCGGGATGGTATAAGAGATGCCATGATTGGTTTAAGAGAAGAAAT GATAGAAAAAATCAGAACTGAAGCATTAATGACCAATGACAGATTA GAAGCTATGGCAAGACTCAGGAATGAGGAAAGTGAAAAGATGGCAA AAGACACATCAGATGAAGTGTCTCTCAATCCAACATCAGAGAAATT |

TABLE 15-continued

| | Table of Sequences | |
|---|---|---|

| SEQ ID NO: | Description | Sequence |
|---|---|---|
| | | GAACAACCTATTGGAAGGGAATGATAGTGACAATGATCTATCACTT |
| | | GAAGATTTCTGATTAGTTACCACTCTTCACATCAACACACAATACC |
| | | AACAGAAGACCAACAAACTAACCAACCCAATCATCCAACCAAACAT |
| | | CCATCCGCCAATCAGCCAAACAGCCAACAAAACAACCAGCCAATCC |
| | | AAAACTAACCACCCGGAAAAAATCTATAATATAGTTACAAAAAAAG |
| | | GAAAGGGTGGGGCAAATATGGAAACATACGTGAACAAGCTTCACGA |
| | | AGGCTCCACATACACAGCTGCTGTTCAATACAATGTCTTAGAAAAA |
| | | GACGATGACCCTGCATCACTTACAATATGGGTGCCCATGTTCCAAT |
| | | CATCTATGCCAGCAGATTTACTTATAAAAGAACTAGCTAATGTCAA |
| | | CATACTAGTGAAACAAATATCCACACCCAAGGGACCTTCACTAAGA |
| | | GTCATGATAAACTCAAGAAGTGCAGTGCTAGCACAAATGCCCAGCA |
| | | AATTTACCATATGCGCTAATGTGTCCTTGGATGAAAGAAGCAAACT |
| | | AGCATATGATGTAACCACACCCTGTGAAATCAAGGCATGTAGTCTA |
| | | ACATGCCTAAAATCAAAAAATATGTTGACTACAGTTAAAGATCTCA |
| | | CTATGAAGACACTCAACCCTACACATGATATTATTGCTTTATGTGA |
| | | ATTTGAAAACATAGTAACATCAAAAAAAGTCATAATACCAACATAC |
| | | CTAAGATCCATCAGTGTCAGAAATAAAGATCTGAACACACTTGAAA |
| | | ATATAACAACCACTGAATTCAAAAATGCTATCACAAATGCAAAAT |
| | | CATCCCTTACTCAGGATTACTATTAGTCATCACAGTGACTGACAAC |
| | | AAAGGAGCATTCAAATACATAAAGCCACAAAGTCAATTCATAGTAG |
| | | ATCTTGGAGCTTACCTAGAAAAAGAAAGTATATATTATGTTACCAC |
| | | AAATTGGAAGCACACAGCTACACGATTTGCAATCAAACCCATGGAA |
| | | GATTAACCTTTTTCCTCTACATCAGTGTGTTAATTCATACAAACTT |
| | | TCTACCTACATTCTTCACTTCACCATCACAATCACAAACACTCTGT |
| | | GGTTCAACCAATCAAACAAAACTTATCTGAAGTCCCAGATCATCCC |
| | | AAGTCATTGTTTATCAGATCTAGTACTCAAATAAGTTAATAAAAAA |
| | | TATACACATGGGGCAAATAATCATTGGAGGAAATCCAACTAATCAC |
| | | AATATCTGTTAACATAGACAAGTCCACACACCATACAGAATCAACC |
| | | AATGGAAAATACATCCATAACAATAGAATTCTCAAGCAAATTCTGG |
| | | CCTTACTTTACACTAATACACATGATCACAACAATAATCTCTTTGC |
| | | TAATCATAATCTCCATCATGATTGCAATACTAAACAAACTTTGTGA |
| | | ATATAACGTATTCCATAACAAAACCTTTGAGTTACCAAGAGCTCGA |
| | | GTCAACACATAGCATTCATCAATCCAACAGCCCAAAACAGTAACCT |
| | | TGCATTTAAAAATGAACAACCCCTACCTCTTTACAACACCTCATTA |
| | | ACATCCCACCATGCAAACCACTATCCATACTATAAAGTAGTTAATT |
| | | AAAAATAGTCATAACAATGAACTAGGATATCAAGACTAACAATAAC |
| | | ATTGGGGCAAATGCAAACATGTCCAAAAACAAGGACCAACGCACCG |
| | | CTAAGACATTAGAAAGGACCTGGGACACTCTCAATCATTTATTATT |
| | | CATATCATCGTGCTTATATAAGTTAAATCTTAAATCTGTAGCACAA |
| | | ATCACATTATCCATTCTGGCAATGATAATCTCAACTTCACTTATAA |
| | | TTGCAGCCATCATATTCATAGCCTCGGCAAACCACAAAGTCACACC |
| | | AACAACTGCAATCATACAAGATGCAACAAGCCAGATCAAGAACACA |
| | | ACCCCAACATACCTCACCCAGAATCCTCAGCTTGGAATCAGTCCCT |
| | | CTAATCCGTCTGAAATTACATCACAAATCACCACCATACTAGCTTC |
| | | AACAACACCAGGAGTCAAGTCAACCCTGCAATCCACAACAGTCAAG |
| | | ACCAAAAACACAACAACAACTCAAACACAACCCAGCAAGCCCACCA |
| | | CAAAACAACGCCAAAACAAACCACCAAGCAAACCCAATAATGATTT |
| | | TCACTTTGAAGTGTTCAACTTTGTACCCTGCAGCATATGCAGCAAC |
| | | AATCCAACCTGCTGGGCTATCTGCAAAAGAATACCAAACAAAAAAC |
| | | CAGGAAAGAAAACCACTACCAAGCCCACAAAAAAACCAACCCTCAA |
| | | GACAACCAAAAAAGATCCCAAACCTCAAACCACTAAATCAAAGGAA |
| | | GTACCCACCACCAAGCCCACAGAAGAGCCAACCATCAACACCACCA |
| | | AAACAAACATCATAACTACACTACTCACCTCCAACACCACAGGAAA |
| | | TCCAGAACTCACAAGTCAAATGGAAACCTTCCACTCAACTTCCTCC |
| | | GAAGGCAATCCAAGCCCTTCTCAAGTCTCTACAACATCCGAGTACC |
| | | CATCACAACCTTCATCTCCACCCAACACCACCACGCCAGTAGTTACT |
| | | TAAAAACATATTATCACAAAAAGCCATGACCAACTTAAACAGAATC |
| | | AAAATAAACTCTGGGGCAAATAACAATGGAGTTGCTAATCCTCAAA |
| | | GCAAATGCAATTACCACAATCCTCACTGCAGTCACATTTTGTTTTG |
| | | CTTCTGGTCAAAACATCACTGAAGAATTTTATCAATCAACATGCAG |
| | | TGCAGTTAGCAAAGGCTATCTTAGTGCTCTGAGAACTGGTTGGTAT |
| | | ACCAGTGTTATAACTATAGAATTAAGTAATATCAAGGAAAATAAGT |
| | | GTAATGGAACAGATGCTAAGGTAAAATTGATAAAACAAGAATTAGA |
| | | TAAATATAAAAATGCTGTAACAGAATTGCAGTTGCTCATGCAAAGC |
| | | ACACCACCAACAAACAATCGAGCCAGAAGAGAACTACCAAGGTTTA |
| | | TGAATTATACACTCAACAATGCCAAAAAAACCAATGTAACATTAAG |
| | | CAAGAAAAGGAAAGAAGATTTCTTGTTTTTTTGTTAGGTGTTGGA |
| | | TCTGCAATCGCCAGTGGCGTTGCTGTATCTAAGGTCCTGCACCTAG |
| | | AAGGGGAAGTGAACAAGATCAAAAGTGCTCTACTATCCACAAACAA |
| | | GGCTCTAGTCAGCTTATCAAATGGAGTTAGTGTCTTAACCAGCAAA |
| | | GTGTTAGACCTCAAAAACTATATAGATAAACAATTGTTACCTATTG |
| | | TGAACAAGCAAAGCTGCAGCATATCAAATATAGAAACTGTGATAGA |
| | | GTTCCAACAAAAGAACAACAGACTACTAGAGATTACCAGGGAATTT |
| | | AGTGTTAATGCAGGTGTAACTACACCTGTAAGCACTTACATGTTAA |

TABLE 15-continued

| | | Table of Sequences |
| --- | --- | --- |

| SEQ ID NO: | Description | Sequence |
| --- | --- | --- |
| | | CTAATAGTGAATTATTGTCATTAATCAATGATATGCCTATAACAAA |
| | | TGATCAGAAAAAGTTAATGTCCAACAATGTTCAAATAGTTAGACAG |
| | | CAAAGTTACTCTATCATGTCCATAATAAAAGAGGAAGTCTTAGCAT |
| | | ATGTAGTACAATTACCACTATATGGTGTTATAGATACACCCTGTTG |
| | | GAAACTACACACATCCCCTCTATGTACAACCAACACAAAAGAAGGG |
| | | TCCAACATCTGTTTAACAAGAACTGACAGAGGATGGTACTGTGACA |
| | | ATGCAGGATCAGTATCTTTCTTCCCACAAGCTGAAACATGTAAAGT |
| | | TCAATCAAATCGAGTATTTTGTGACACAATGAACAGTTTAACATTA |
| | | CCAAGTGAAATAAATCTCTGCAATGTTGACATATTCAACCCCAAAT |
| | | ATGATTGTAAAATTATGACTTCAAAAACAGATGTAAGCAGCTCCGT |
| | | TATCACATCTCTAGGAGCCATTGTGTCATGCTATGGCAAAACTAAA |
| | | TGTACAGCATCCAATAAAAATCGTGGAATCATAAAGACATTTTCTA |
| | | ACGGGTGCGATTATGTATCAAATAAAGGGATGGACACTGTGTCTGT |
| | | AGGTAACACATTATATTATGTAAATAAGCAAGAAGGTAAAAGTCTC |
| | | TATGTAAAAGGTGAACCAATAATAAATTTCTATGACCCATTAGTAT |
| | | TCCCCTCTGATGAATTTGATGCATCAATATCTCAAGTCAACGAGAA |
| | | GATTAACCAGAGCCTAGCATTTATTCGTAAATCCGATGAATTATTA |
| | | CATAATGTAAATGCTGGTAAATCCACCACAAATATCATGATAACTA |
| | | CTATAATTATAGTGATTATAGTAATATTGTTATCATTAATTGCTGT |
| | | TGGACTGCTCTTATACTGTAAGGCCAGAAGCACACCAGTCACACTA |
| | | AGCAAAGATCAACTGAGTGGTATAAATAATATTGCATTTAGTAACT |
| | | AAATAAAAATAGCACCTAATCATGTTCTTACAATGGTTTACTATCT |
| | | GCTCATAGACAACCCATCTGTCATTGGATTTTCTTAAAATCTGAAC |
| | | TTCATCGAAACTCTCATCTATAAACCATCTCACTTACACTATTTAA |
| | | GTAGATTCCTAGTTTATAGTTATATAAAACACAATTGAATGCCAGA |
| | | TTAACTTACCATCTGTAAAAATGAAAACTGGGGCAAATATGTCACG |
| | | AAGGAATCCTTGCAAATTTGAAATTCGAGGTCATTGCTTAAATGGT |
| | | AAGAGGTGTCATTTTAGTCATAATTATTTTGAATGGCCACCCCATG |
| | | CACTGCTTGTAAGACAAAACTTTATGTTAAACAGAATACTTAAGTC |
| | | TATGGATAAAAGTATAGATACCTTATCAGAAATAAGTGGAGCTGCA |
| | | GAGTTGGACAGAACAGAAGAGTATGCTCTTGGTGTAGTTGGAGTGC |
| | | TAGAGAGTTATATAGGATCAATAAACAATATAACTAAACAATCAGC |
| | | ATGTGTTGCCATGAGCAAACTCCTCACTGAACTCAATAGTGATGAT |
| | | ATCAAAAAGCTGAGGGACAATGAAGAGCTAAATTCACCCAAGATAA |
| | | GAGTGTACAATACTGTCATATCATATATTGAAAGCAACAGGAAAAA |
| | | CAATAAACAAACTATCCATCTGTTAAAAAGATTGCCAGCAGACGTA |
| | | TTGAAGAAAACCATCAAAAACACATTGGATATCCATAAGAGCATAA |
| | | CCATCAACAACCCAAAAGAATCAACTGTTAGTGATACAAATGACCA |
| | | TGCCAAAAATAATGATACTACCTGACAAATATCCTTGTAGTATAAC |
| | | TTCCATACTAATAACAAGTAGATGTAGAGTTACTATGTATAATCAA |
| | | AAGAACACACTATATTTCAATCAAAACAACCCAAATAACCATATGT |
| | | ACTCACCGAATCAAACATTCAATGAAATCCATTGGACCTCTCAAGA |
| | | ATTGATTGACACAATTCAAATTTTTCTACAACATCTAGGTATTATT |
| | | GAGGATATATATACAATATATATATTAGTGTCATAACACTCAATTC |
| | | TAACACTCACCACATCGTTACATTATTAATTCAAACAATTCAAGTT |
| | | GTGGGACAAAATGGATCCCATTATTAATGGAAATTCTGCTAATGTT |
| | | TATCTAACCGATAGTTATTTAAAAGGTGTTATCTCTTTCTCAGAGT |
| | | GTAATGCTTTAGGAAGTTACATATTCAATGGTCCTTATCTCAAAAA |
| | | TGATTATACCAACTTAATTAGTAGACAAAATCCATTAATAGAACAC |
| | | ATGAATCTAAAGAAACTAAATATAACACAGTCCTTAATATCTAAGT |
| | | ATCATAAAGGTGAAATAAAATTAGAAGAACCTACTTATTTTCAGTC |
| | | ATTACTTATGACATACAAGAGTATGACCTCGTCAGAACAGATTGCT |
| | | ACCACTAATTTACTTAAAAAGATAATAAGAAGAGCTATAGAAATAA |
| | | GTGATGTCAAAGTCTATGCTATATTGAATAAAACTAGGGCTTAAAGA |
| | | AAAGGACAAGATTAAATCCAACAATGGACAAGATGAAGACAACTCA |
| | | GTTATTACGACCATAATCAAAGATGATATACTTTCAGCTGTTAAAG |
| | | ATAATCAATCTCATCTTAAAGCAGACAAAAATCACTCTACAAAACA |
| | | AAAAGACACAATCAAAACAACACTCTTGAAGAAATTGATGTGTTCA |
| | | ATGCAACATCCTCCATCATGGTTAATACATTGGTTTAACTTATACA |
| | | CAAAATTAAACAACATATTAACACAGTATCGATCAAATGAGGTAAA |
| | | AAACCATGGGTTTACATTGATAGATAATCAAACTCTTAGTGGATTT |
| | | CAATTTATTTTGAACCAATATGGTTGTATAGTTTATCATAAGGAAC |
| | | TCAAAAGAATTACTGTGACAACCTATAATCAATTCTTGACATGGAA |
| | | AGATATTAGCCTTAGTAGATTAAATGTTTGTTTAATTACATGGATT |
| | | AGTAACTGCTTGAACACATTAAATAAAAGCTTAGGCTTAAGATGCG |
| | | GATTCAATAATGTTATCTTGACACAACTATTCCTTTATGGAGATTG |
| | | TATACTAAAGCTATTTCACAATGAGGGGTTCTACATAATAAAAGAG |
| | | GTAGAGGGATTTATTATGTCTCTAATTTTAAATATAACAGAAGAAG |
| | | ATCAATTCAGAAAACGATTTTATAATAGTATGCTCAACAACATCAC |
| | | AGATGCTGCTAATAAAGCTCAGAAAAATCTGCTATCAAGAGTATGT |
| | | CATACATTATTAGATAAGACAGTGTCCGATAATATAATAAATGGCA |
| | | GATGGATAATTCTATTAAGTAAGTTCCTTAAATTAATTAAGCTTGC |
| | | AGGTGACAATAACCTTAACAATCTGAGTGAACTATATTTTTTGTTC |
| | | AGAATATTTGGACACCCAATGGTAGATGAAAGACAAGCCATGGATG |

TABLE 15-continued

Table of Sequences

| SEQ ID NO: | Description | Sequence |
|---|---|---|
| | | CTGTTAAAATTAATTGCAATGAGACCAAATTTTACTTGTTAAGCAG TCTGAGTATGTTAAGAGGTGCCTTTATATATAGAATTATAAAAGGG TTTGTAAATAATTACAACAGATGGCCTACTTTAAGAAATGCTATTG TTTTACCCTTAAGATGGTTAACTTACTATAAACTAAACACTTATCC TTCTTTGTTGGAACTTACAGAAAGAGATTTGATTGTGTTATCAGGA CTACGTTTCTATCGTGAGTTTCGGTTGCCTAAAAAAGTGGATCTTG AAATGATTATAAATGATAAAGCTATATCACCTCCTAAAAATTTGAT ATGGACTAGTTTCCCTAGAAATTACATGCCATCACACATACAAAAC TATATAGAACATGAAAAATTAAAATTTTCCGAGAGTGATAAATCAA GAAGAGTATTAGAGTATTATTTAAGAGATAACAAATTCAATGAATG TGATTTATACAACTGTGTAGTTAATCAAAGTTATCTCAACAACCCT AATCATGTGGTATCATTGACAGGCAAAGAAAGAGAACTCAGTGTAG GTAGAATGTTTGCAATGCAACCGGGAATGTTCAGACAGGTTCAAAT ATTGGCAGAGAAAATGATAGCTGAAAACATTTTACAATTCTTTCCT GAAAGTCTTACAAGATATGGTGATCTAGAACTACAAAAAATATTAG AATTGAAAGCAGGAATAAGTAACAAATCAAATCGCTACAATGATAA TTACAACAATTACATTAGTAAGTGCTCTATCATCACAGATCTCAGC AAATTCAATCAAGCATTTCGATATGAAACGTCATGTATTTGTAGTG ATGTGCTGGATGAACTGCATGGTGTACAATCTCTATTTTCCTGGTT ACATTTAACTATTCCTCATGTCACAATAATATGCACATATAGGCAT GCACCCCCCTATATAGGAGATCATATTGTAGATCTTAACAATGTAG ATGAACAAAGTGGATTATATAGATATCACATGGGTGGCATCGAAGG GTGGTGTCAAAAACTGTGGACCATAGAAGCTATATCACTATTGGAT CTAATATCTCTCAAAGGGAAATTCTCAATTACTGCTTTAATTAATG GTGACAATCAATCAATAGATATAAGCAAACCAATCAGACTCATGGA AGGTCAAACTCATGCTCAAGCAGATTATTTGCTAGCATTAAATAGC CTTAAATTACTGTATAAAGAGTATGCAGGCATAGGCCACAAATTAA AAGGAACTGAGACTTATATATCACGAGATATGCAATTTATGAGTAA AACAATTCAACATAACGGTGTATATTACCCAGCTAGTATAAAGAAA GTCCTAAGAGTGGGACCGTGGATAAACACTATACTTGATGATTTCA AAGTGAGTCTAGAATCTATAGGTAGTTTGACACAAGAATTAGAATA TAGAGGTGAAAGTCTATTATGCAGTTTAATATTTAGAAATGTATGG TTATATAATCAGATTGCTCTACAATTAAAAAAATCATGCATTATGTA ACAATAAACTATATTTGGACATATTAAAGGTTCTGAAACACTTAAA AACCTTTTTTAATCTTGATAATATTGATACAGCATTAACATTGTAT ATGAATTTACCCATGTTATTTGGTGGTGGTGATCCCAACTTGTTAT ATCGAAGTTTCTATAGAAGAACTCCTGACTTCCTCACAGAGGCTAT AGTTCACTCTGTGTTCATACTTAGTTATTATACAAACCATGACTTA AAAGATAAACTTCAAGATCTGTCAGATGATAGATTGAATAAGTTCT TAACATGCATAATCACGTTTGACAAAAACCCTAATGCTGAATTCGT AACATTGATGAGAGATCCTCAAGCTTTAGGGTCTGAGAGACAAGCT AAAATTACTAGCGAAATCAATAGACTGGCAGTTACAGAGGTTTTGA GTACAGCTCCAAACAAAATATTCTCCAAAAGTGCACAACATTATAC TACTACAGAGATAGATCTAAATGATATTATGCAAAATATAGAACCT ACATATCCTCATGGGCTAAGAGTTGTTTATGAAAGTTTACCCTTTT ATAAAGCAGAGAAAATAGTAAATCTTATATCAGGTACAAAATCTAT AACTAACATACTGGAAAAAACTTCTGCCATAGACTTAACAGATATT GATAGAGCCACTGAGATGATGAGGAAAAACATAACTTTGCTTATAA GGATACTTCCATTGGATTGTAACAGAGATAAAAGAGAGATATTGAG TATGGAAAACCTAAGTATTACTGAATTAAGCAAATATGTTAGGGAA AGATCTTGGTCTTTATCCAATATAGTTGGTGTTACATCACCCAGTA TCATGTATACAATGGACATCAAATATACTACAAGCACTATATCTAG TGGCATAATTATAGAGAAATATAATGTTAACAGTTTAACACGTGGT GAGAGAGGACCCACTAAACCATGGGTTGGTTCATCTACACAAGAGA AAAAAACAATGCCAGTTTATAATAGACAAGTCTTAACCAAAAAACA GAGAGATCAAATAGATCTATTAGCAAAATTGGATTGGGTGTATGCA TCTATAGATAACAAGGATGAATTCATGGAAGAACTCAGCATAGGAA CCCTTGGGTTAACATATGAAAAGGCCAAGAAATTATTTCCACAATA TTTAAGTGTCAATTATTTGCATCGCCTTACAGTCAGTAGTAGACCA TGTGAATTCCCTGCATCAATACCAGCTTATAGAACAACAAATTATC ACTTTGACACTAGCCCTATTAATCGCATATTAACAGAAAAGTATGG TGATGAAGATATTGACATAGTATTCCAAAACTGTATAAGCTTTGGC CTTAGTTTAATGTCAGTAGTAGAACAATTTACTAATGTATGTCCTA ACAGAATTATTCTCATACCTAAGCTTAATGAGATACATTTGATGAA ACCTCCCATATTCACAGGTGATGTTGATATTCACAAGTTAAAACAA GTGATACAAAAACAGCATATGTTTTTACCAGACAAAATAAGTTTGA CTCAATATGTGGAATTATTCTTAAGTAATAAAACACTCAAATCTGG ATCTCATGTTAATTCTAATTTAATATTGGCACATAAAATATCTGAC TATTTTCATAATACTTACATTTTAAGTACTAATTTAGCTGGACATT GGATTCTGATTATACAACTTATGAAAGATTCTAAAGGTATTTTTGA AAAAGATTGGGGAGAGGGATATATAACTGATCATATGTTTATTAAT TTGAAAGTTTTCTTCAATGCTTATAAGACCTATCTCTTGTGTTTTC ATAAAGGTTATGGCAAAGCAAAGCTGGAGTGTGATATGAACACTTC AGATCTTCTATGTGTATTGGAATTAATAGACAGTAGTTATTGGAAG |

TABLE 15-continued

Table of Sequences

| SEQ ID NO: | Description | Sequence |
|---|---|---|
| | | TCTATGTCTAAGGTATTTTTAGAACAAAAAGTTATCAAATACATTC |
| | | TTAGCCAAGATGCAAGTTTACATAGAGTAAAAGGATGTCATAGCTT |
| | | CAAATTATGGTTTCTTAAACGTCTTAATGTAGCAGAATTCACAGTT |
| | | TGCCCTTGGGTTGTTAACATAGATTATCATCCAACACATATGAAAG |
| | | CAATATTAACTTATATAGATCTTGTTAGAATGGGATTGATAAATAT |
| | | AGATAGAATACACATTAAAAATAAACACAAATTCAATGATGAATTT |
| | | TATACTTCTAATCTCTTCTACATTAATTATAACTTCTCAGATAATA |
| | | CTCATCTATTAACTAAACATATAAGGATTGCTAATTCTGAATTAGA |
| | | AAATAATTACAACAAATTATATCATCCTACACCAGAAACCCTAGAG |
| | | AATATACTAGCCAATCCGATTAAAAGTAATGACAAAAAGACACTGA |
| | | ATGACTATTGTATAGGTAAAAATGTTGACTCAATAATGTTACCATT |
| | | GTTATCTAATAAGAAGCTTATTAAATCGTCTGCAATGATTAGAACC |
| | | AATTACAGCAAACAAGATTTGTATAATTTATTCCCTATGGTTGTGA |
| | | TTGATAGAATTATAGATCATTCAGGCAATACAGCCAAATCCAACCA |
| | | ACTTTACACTACTACTTCCCACCAAATATCTTTAGTCCACAATAGC |
| | | ACATCACTTTACTGCATGCTTCCTTGGCATCATATTAATAGATTCA |
| | | ATTTTGTATTTAGTTCTACAGGTTGTAAAATTAGTATAGAGTATAT |
| | | TTTAAAAGATCTTAAAATTAAAGATCCCAATTGTATAGCATTCATA |
| | | GGTGAAGGAGCAGGGAATTTATTATTGCGTACAGTAGTGGAACTTC |
| | | ATCCTGACATAAGATATATTTACAGAAGTCTGAAAGATTGCAATGA |
| | | TCATAGTTTACCTATTGAGTTTTTAAGGCTGTACAATGGACATATC |
| | | AACATTGATTATGGTGAAAATTTGACCATTCCTGCTACAGATGCAA |
| | | CCAACAACATTCATTGGTCTTATTTACATATAAAGTTTGCTGAACC |
| | | TATCAGTCTTTTTGTCTGTGATGCCGAATTGTCTGTAACAGTCAAC |
| | | TGGAGTAAAATTATAATAGAATGGAGCAAGCATGTAAGAAAGTGCA |
| | | AGTACTGTTCCTCAGTTAATAAATGTATGTTAATAGTAAAATATCA |
| | | TGCTCAAGATGATATTGATTTCAAATTAGACAATATAACTATATTA |
| | | AAAACTTATGTATGCTTAGGCAGTAAGTTAAAGGGATCGGAGGTTT |
| | | ACTTAGTCCTTACAATAGGTCCTGCGAATATATTCCCAGTATTTAA |
| | | TGTAGTACAAAATGCTAAATTGATACTATCAAGAACCAAAAATTTC |
| | | ATCATGCCTAAGAAAGCTGATAAAGAGTCTATTGATGCAAATATTA |
| | | AAAGTTTGATACCCTTTCTTTGTTACCCTATAACAAAAAAAGGAAT |
| | | TAATACTGCATTGTCAAAACTAAAGAGTGTTGTTAGTGGAGATATA |
| | | CTATCATATTCTATAGCTGGACGTAATGAAGTTTTCAGCAATAAAC |
| | | TTATAAATCATAAGCATATGAACATCTTAAAATGGTTCAATCATGT |
| | | TTTAAATTTCAGATCAACAGAACTAAACTATAACCATTTATATATG |
| | | GTAGAATCTACATATCCTTACCTAAGTGAATTGTTAAACAGCTTGA |
| | | CAACCAATGAACTTAAAAAACTGATTAAAATCACAGGTAGTCTGTT |
| | | ATACAACTTTCATAATGAATAATGAATAAAGATCTTATAATAAAAA |
| | | TTCCCATAGCTATACACTAACACTGTATTCAATTATAGTTATTAAA |
| | | AATTAAAAATCATATAATTTTTTAAATAACTTTTAGTGAACTAATC |
| | | CTAAAGTTATCATTTTAATCTTGGAGGAATAAATTTAAACCCTAAT |
| | | CTAATTGGTTTATATGTGTATTAACTAAATTACGAGATATTAGTTT |
| | | TTGACACTTTTTTTCTCGT |
| 15 | GS-NlucP-GE GS: nt 1-15 NlucP: nt 616-54 GE: nt 655-671 | GGGGCAAATAAATCAATGGTCTTCACACTCGAAGATTTCGTTGGGG ACTGGCGACAGACAGCCGGCTACAACCTGGACCAAGTCCTTGAACA GGGAGGTGTGTCCAGTTTGTTTCAGAATCTCGGGGTGTCCGTAACT CCGATCCAAAGGATTGTCCTGAGCGGTGAAATGGGCTGAAGATCG ACATCCATGTCATCATCCCGTATGAAGGTCTGAGCGGCGACCAAAT GGGCCAGATCGAAAAAATTTTTAAGGTGGTGTACCCTGTGGATGAT CATCACTTTAAGGTGATCCTGCACTATGGCACACTGGTAATCGACG GGGTTACGCCGAACATGATCGACTATTTCGGACGGCCGTATGAAGG CATCGCCGTGTTCGACGGCAAAAAGATCACTGTAACAGGGACCCTG TGGAACGGCAACAAAATTATCGACGAGCGCCTGATCAACCCCGACG GCTCCCTGCTGTTCCGAGTAACCATCAACGGAGTGACCGGCTGGCG GCTGTGCGAACGCATTCTGGCGAATTCTCACGGCTTTCCGCCTGAG GTTGAAGAGCAAGCCGCCGGTACATTGCCTATGTCCTGCGCACAAG AAAGCGGTATGGACCGGCACCCAGCCGCTTGTGCTTCAGCTCGCAT CAACGTCTAAATTATAGTAATTTAAAA |
| 16 | RSV gene start sequence | GGGGCAAATAAATCA |
| 17 | RSV gene end sequence | ATTATAGTAATTTAAAA |
| 18 | NanolucP gene | ATGGTCTTCACACTCGAAGATTTCGTTGGGGACTGGCGACAGACAG CCGGCTACAACCTGGACCAAGTCCTTGAACAGGGAGGTGTGTCCAG TTTGTTTCAGAATCTCGGGGTGTCCGTAACTCCGATCCAAAGGATT GTCCTGAGCGGTGAAATGGGCTGAAGATCGACATCCATGTCATCA TCCCGTATGAAGGTCTGAGCGGCGACCAAATGGGCCAGATCGAAAA AATTTTTAAGGTGGTGTACCCTGTGGATGATCATCACTTTAAGGTG ATCCTGCACTATGGCACACTGGTAATCGACGGGGTTACGCCGAACA |

TABLE 15-continued

Table of Sequences

| SEQ ID NO: | Description | Sequence |
|---|---|---|
| | | TGATCGACTATTTCGGACGGCCGTATGAAGGCATCGCCGTGTTCGA |
| | | CGGCAAAAAGATCACTGTAACAGGGACCCTGTGGAACGGCAACAAA |
| | | ATTATCGACGAGCGCCTGATCAACCCCGACGGCTCCCTGCTGTTCC |
| | | GAGTAACCATCAACGGAGTGACCGGCTGGCGGCTGTGCGAACGCAT |
| | | TCTGGCGAATTCTCACGGCTTTCCGCCTGAGGTTGAAGAGCAAGCC |
| | | GCCGGTACATTGCCTATGTCCTGCGCACAAGAAAGCGGTATGGACC |
| | | GGCACCCAGCCGCTTGTGCTTCAGCTCGCATCAACGTCTAA |
| 19 | Forward primer for NanolucP | TATAGTTACAAAAAAAGGAAGGGGCAAATAAATCAATGGTCTTCAC ACTCGAAGATT |
| 20 | Reverse primer for NanolucP | TTCCATATTTGCCCCACCCTTTTTAAATTACTATAATTTAGACGTT GATGCGAGCTG |
| 21 | pSMART RS A2 NLucP NS1 CDS: nt 127-543 NS2 CDS: nt 656-1027 N CDS: nt 1168-2340 P CDS: nt 2374-3096 Intergenic P-M region: nt 3271-3950 GS-NlucP-GE: nt 3275-3945 GS: nt 33275-289 GE: nt 3929-3945 nanoLucP CDS: nt 3290-3928 M CDS: nt 3960-4727 SH CDS: nt 5002-5193 G CDS: nt 5387-6280 F CDS: nt 6360-8081 M2-1 CDS: nt 8305-8886 M2-2 CDS: nt 8858-9127 L CDS: nt 9197-15,691 | GGCGCGCCTAATACGACTCACTATAGGGACGGGAAAAAATGCGTAC AACAAACTTGCATAAACCAAAAAAATGGGGCAAATAAGAATTTGAT AAGTACCACTTAAATTTAACTCCCTTGGTTAGAGATGGGCAGCAAT TCATTGAGTATGATAAAAGTTAGATTACAAAATTTGTTTGACAATG ATGAAGTAGCATTGTTAAAAATAACATGCTATACTGATAAATTAAT ACATTTAACTAACGCTTTGGCTAAGGCAGTGATACATACAATCAAA TTGAATGGCATTGTGTTTGTGCATGTTATTACAAGTAGTGATATTT GCCCTAATAATAATATTGTAGTAAAATCCAATTTCACAACAATGCC AGTACTACAAAATGGAGGTTATATATGGGAAATGATGGAATTAACA CATTGCTCTCAACCTAATGGTCTACTAGATGACAATTGTGAAATTA AATTCTCCAAAAAACTAAGTGATTCAACAATGACCAATTATATGAA TCAATTATCTGAATTACTTGGATTTGATCTTAATCCATAAATTATA ATTAATATCAACTAGCAAATCAATGTCACTAACACCATTAGTTAAT ATAAAACTTAACAGAAGACAAAAATGGGGCAAATAAATCAATTCAG CCAACCCAACCATGGACACAACCCACAATGATAATACACCACAAAG ACTGATGATCACAGACATGAGACCGTTGTCACTTGAGACCATAATA ACATCACTAACCAGAGACATCATAACACACAAATTTATATACTTGA TAAATCATGAATGCATAGTGAGAAAACTTGATGAAAAACAGGCCAC ATTTACATTCCTGGTCAACTATGAAATGAAACTATTACACACAAGTA GGAAGCACTAAATATAAAAAAATATACTGAATACAACACAAAATATG GCACTTTCCCTATGCCAATATTCATCAATCATGATGGGTTCTTAGA ATGCATTGGCATTAAGCCTACAAAGCATACTCCCATAATATACAAG TATGATCTCAATCCATAAATTTCAACACAATATTCACACAATCTAA AACAACAACTCTATGCATAACTATACTCCATAGTCCAGATGGAGCC TGAAAATTATAGTAATTTAAAATTAAGGAGAGATATAAGATAGAAGA ATGGGGCAAATACAAAGATGGCTCTTAGCAAAGTCAAGTTGAATGA TACACTCAACAAAGATCAACTTCTGTCATCCAGCAAATACACCATC CAACGGAGCACAGGAGATAGTATTGATACTCCTAATTATGATGTGC AGAAACACATCAATAAGTTATGTGGCATGTTATTAATCACAGAAGA TGCTAATCATAAAATTCACTGGGTTAATAGGTATGTTATATGCGATG TCTAGGTTAGGAAGAGAAGACACCATAAAAATACTCAGAGATGCGG GATATCATGTAAAAGCAAATGGAGTAGATGTAACAACACATCGTCA AGACATTAATGGAAAAGAAATGAAATTTGAAGTGTTAACATTGGCA AGCTTAACAACTGAAATTCAAATCAACATTGAGATAGAATCTAGAA AATCCTACAAAAAAATGCTAAAAGAAATGGGAGAGGTAGCTCCAGA ATACAGGCATGACTCTCCTGATTGTGGGATGATAATATTATGTATA GCAGCATTAGTAATAACTAAATTAGCAGCAGGGGACAGATCTGGTC TTACAGCCGTGATTAGGAGAGCTAATAATGTCCTAAAAAATGAAAT GAAACGTTACAAAGGCTTACTACCCAAGGACATAGCCAACAGCTTC TATGAAGTGTTTGAAAAACATCCCCACTTTATAGATGTTTTTGTTC ATTTTGGTATAGCACAATCTTCTACCAGAGGTGGCAGTAGAGTTGA AGGGATTTTTGCAGGATTGTTTATGAATGCCTATGGTGCAGGGCAA GTGATGTTACGGTGGGGAGTCTTAGCAAAATCAGTTAAAAATATTA TGTTAGGACATGCTAGTGTGCAAGCAGAAATGGAACAAGTTGTTGA GGTTTATGAATATGCCCAAAAATTGGGTGGTGAAGCAGGATTCTAC CATATATTGAACAACCCAAAAGCATCATTATTATCTTTGACTCAAT TTCCTCACTTCTCCAGTGTAGTATTAGGCAATGCTGCTGGCCTAGG CATAATGGGAGAGTACAGAGGTACACCGAGGAATCAAGATCTATAT GATGCAGCAAAGGCATATGCTGAACAACTCAAAGAAAATGGTGTGA TTAACTACAGTGTACTAGACTTGACAGCAGAAGAACTAGAGGCTAT CAAACATCAGCTTAATCCAAAAGATAATGATGTAGAGCTTTGAGTT AATAAAAAATGGGGCAAATAAATCATCATGGAAAAGTTTGCTCCTG AATTCCATGGAGAAGATGCAAACAACAGGGCTACTAAATTCCTAGA ATCAATAAAGGGCAAATTCACATCACCCAAAGATCCCAAGAAAAA GATAGTATCATATCTGTCAACTCAATAGATATAGAAGTAACCAAAG AAAGCCCTATAACATCAAATTCAACTATTATCAACCCAACAAATGA GACAGATGATACTGCAGGGAACAAGCCCAATTATCAAAGAAACCT CTAGTAAGTTTCAAAGAAGACCCTACACCAAGTGATAATCCCTTTT CTAAACTATACAAAGAAACCATAGAAACATTTGATAACAATGAAGA |

TABLE 15-continued

Table of Sequences

| SEQ ID NO: | Description | Sequence |
|---|---|---|
| | | AGAATCCAGCTATTCATACGAAGAAATAAATGATCAGACAAACGAT |
| | | AATATAACAGCAAGATTAGATAGGATTGATGAAAAATTAAGTGAAA |
| | | TACTAGGAATGCTTCACACATTAGTAGTGGCAAGTGCAGGACCTAC |
| | | ATCTGCTCGGGATGGTATAAGAGATGCCATGATTGGTTTAAGAGAA |
| | | GAAATGATAGAAAAAATCAGAACTGAAGCATTAATGACCAATGACA |
| | | GATTAGAAGCTATGGCAAGACTCAGGAATGAGGAAAGTGAAAAGAT |
| | | GGCAAAAGACACATCAGATGAAGTGTCTCTCAATCCAACATCAGAG |
| | | AAATTGAACAACCTATTGGAAGGGAATGATAGTGACAATGATCTAT |
| | | CACTTGAAGATTTCTGATTAGTTACCACTCTTCACATCAACACACA |
| | | ATACCAACAGAAGACCAACAAACTAACCAACCCAATCATCCAACCA |
| | | AACATCCATCCGCCAATCAGCCAAACAGCCAACAAAACAACCAGCC |
| | | AATCCAAAACTAACCACCCGGAAAAAATCTATAATATAGTTACAAA |
| | | AAAAGGAAGGGGCAAATAAATCAATGGTCTTCACACTCGAAGATTT |
| | | CGTTGGGGACTGGCGACAGACAGCCGGCTACAACCTGGACCAAGTC |
| | | CTTGAACAGGGAGGTGTGTCCAGTTTGTTTCAGAATCTCGGGGTGT |
| | | CCGTAACTCCGATCCAAAGGATTGTCCTGAGCGGTGAAAATGGGCT |
| | | GAAGATCGACATCCATGTCATCATCCCGTATGAAGGTCTGAGCGGC |
| | | GACCAAATGGGCCAGATCGAAAAAATTTTTAAGGTGGTGTACCCTG |
| | | TGGATGATCATCACTTTAAGGTGATCCTGCACTATGGCACACTGGT |
| | | AATCGACGGGGTTACGCCGAACATGATCGACTATTTCGGACGGCCG |
| | | TATGAAGGCATCGCCGTGTTCGACGGCAAAAAGATCACTGTAACAG |
| | | GGACCCTGTGGAACGGCAACAAAATTATCGACGAGCGCCTGATCAA |
| | | CCCCGACGGCTCCCTGCTGTTCCGAGTAACCATCAACGGAGTGACC |
| | | GGCTGGCGGCTGTGCGAACGCATTCTGGCGAATTCTCACGGCTTTC |
| | | CGCCTGAGGTTGAAGAGCAAGCCGCCGGTACATTGCCTATGTCCTG |
| | | CGCACAAGAAAGCGGTATGGACCGGCACCCAGCCGCTTGTGCTTCA |
| | | GCTCGCATCAACGTCTAAATTATAGTAATTTAAAAAGGGTGGGGCA |
| | | AATATGGAAACATACGTGAACAAGCTTCACGAAGGCTCCACATACA |
| | | CAGCTGCTGTTCAATACAATGTCTTAGAAAAAGACGATGACCCTGC |
| | | ATCACTTACAATATGGGTGCCCATGTTCCAATCATCTATGCCAGCA |
| | | GATTTACTTATAAAAGAACTAGCTAATGTCAACATACTAGTGAAAC |
| | | AAATATCCACACCCAAGGGACCTTCACTAAGAGTCATGATAAACTC |
| | | AAGAAGTGCAGTGCTAGCACAAATGCCCAGCAAATTTACCATATGC |
| | | GCTAATGTGTCCTTGGATGAAAGAAGCAAACTAGCATATGATGTAA |
| | | CCACACCCTGTGAAATCAAGGCATGTAGTCTAACATGCCTAAAATC |
| | | AAAAAATATGTTGACTACAGTTAAAGATCTCACTATGAAGACACTC |
| | | AACCCTACACATGATATTATTGCTTTATGTGAATTTGAAAACATAG |
| | | TAACATCAAAAAAAGTCATAATACCAACATACCTAAGATCCATCAG |
| | | TGTCAGAAATAAAGATCTGAACACACTTGAAAATATAACAACCACT |
| | | GAATTCAAAAATGCTATCACAAATGCAAAAATCATCCCTTACTCAG |
| | | GATTACTATTAGTCATCACAGTGACTGACAACAAAGGAGCATTCAA |
| | | ATACATAAAGCCACAAAGTCAATTCATAGTAGATCTTGGAGCTTAC |
| | | CTAGAAAAAGAAAGTATATATTATGTTACCACAAATTGGAAGCACA |
| | | CAGCTACACGATTTGCAATCAAACCCATGGAAGATTAACCTTTTTC |
| | | CTCTACATCAGTGTGTTAATTCATACAAACTTTCTACCTACATTCT |
| | | TCACTTCACCATCACAATCACAAACACTCTGTGGTTCAACCAATCA |
| | | AACAAAACTTATCTGAAGTCCCAGATCATCCCAAGTCATTGTTTAT |
| | | CAGATCTAGTACTCAAATAAGTTAATAAAAAATATACACATGGGGC |
| | | AAATAATCATTGGAGGAAATCCAACTAATCACAATATCTGTTAACA |
| | | TAGACAAGTCCACACACCATACAGAATCAACCAATGGAAAATACAT |
| | | CCATAACAATAGAATTCTCAAGCAAATTCTGGCCTTACTTTACACT |
| | | AATACACATGATCACAACAATAATCTCTTTGCTAATCATAATCTCC |
| | | ATCATGATTGCAATACTAAACAAACTTTGTGAATATAACGTATTCC |
| | | ATAACAAAACCTTTGAGTTACCAAGAGCTCGAGTCAACACATAGCA |
| | | TTCATCAATCCAACAGCCCAAAACAGTAACCTTGCATTTAAAAATG |
| | | AACAACCCCTACCTCTTTACAACACCTCATTAACATCCCACCATGC |
| | | AAACCACTATCCATACTATAAAGTAGTTAATTAAAAATAGTCATAA |
| | | CAATGAACTAGGATATCAAGACTAACAATAACATTGGGGCAAATGC |
| | | AAACATGTCCAAAAACAAGGACCAACGCACCGCTAAGACATTAGAA |
| | | AGGACCTGGGACACTCTCAATCATTTATTATTCATATCATCGTGCT |
| | | TATATAAGTTAAATCTTAAATCTGTAGCACAAATCACATTATCCAT |
| | | TCTGGCAATGATAATCTCAACTTCACTTATAATTGCAGCCATCATA |
| | | TTCATAGCCTCGGCAAACCACAAAGTCACACCAACAACTGCAATCA |
| | | TACAAGATGCAACAAGCCAGATCAAGAACACAACCCCAACATACCT |
| | | CACCCAGAATCCTCAGCTTGGAATCAGTCCCTCTAATCCGTCTGAA |
| | | ATTACATCACAAATCACCACCATACTAGCTTCAACAACACCAGGAG |
| | | TCAAGTCAACCCTGCAATCCACAACAGTCAAGACCAAAAACACAAC |
| | | AACAACTCAAACACAACCCAGCAAGCCCACCACAAAACAACGCCAA |
| | | AACAAACCACCAAGCAAACCCAATAATGATTTTCACTTTGAAGTGT |
| | | TCAACTTTGTACCCTGCAGCATATGCAGCAACAATCCAACCTGCTG |
| | | GGCTATCTGCAAAGAATACCAAACAAAAAACCAGGAAAGAAAACC |
| | | ACTACCAAGCCCACAAAAAAACCAACCCTCAAGACAACCAAAAAAG |
| | | ATCCCAAACCTCAAACCACTAAATCAAAGGAAGTACCCACCACCAA |
| | | GCCCACAGAAGAGCCAACCATCAACACCACCAAAACAAACATCATA |

TABLE 15-continued

Table of Sequences

| SEQ ID NO: | Description | Sequence |
|---|---|---|
| | | ACTACACTACTCACCTCCAACACCACAGGAAATCCAGAACTCACAA |
| | | GTCAAATGGAAACCTTCCACTCAACTTCCTCCGAAGGCAATCCAAG |
| | | CCCTTCTCAAGTCTCTACAACATCCGAGTACCCATCACAACCTTCA |
| | | TCTCCACCCAACACACCACGCCAGTAGTTACTTAAAAACATATTAT |
| | | CACAAAAAGCCATGACCAACTTAAACAGAATCAAAATAAACTCTGG |
| | | GGCAAATAACAATGGAGTTGCTAATCCTCAAAGCAAATGCAATTAC |
| | | CACAATCCTCACTGCAGTCACATTTTGTTTTGCTTCTGGTCAAAAC |
| | | ATCACTGAAGAATTTTATCAATCAACATGCAGTGCAGTTAGCAAAG |
| | | GCTATCTTAGTGCTCTGAGAACTGGTTGGTATACCAGTGTTATAAC |
| | | TATAGAATTAAGTAATATCAAGGAAAATAAGTGTAATGGAACAGAT |
| | | GCTAAGGTAAAATTGATAAAACAAGAATTAGATAAATATAAAAATG |
| | | CTGTAACAGAATTGCAGTTGCTCATGCAAAGCACACCACCAACAAA |
| | | CAATCGAGCCAGAAGAGAACTACCAAGGTTTATGAATTATACACTC |
| | | AACAATGCCAAAAAAACCAATGTAACATTAAGCAAGAAAAGGAAAA |
| | | GAAGATTTCTTGTTTTTTTGTTAGGTGTTGGATCTGCAATCGCCAG |
| | | TGGCGTTGCTGTATCTAAGGTCCTGCACCTAGAAGGGGAAGTGAAC |
| | | AAGATCAAAAGTGCTCTACTATCCACAAACAAGGCTCTAGTCAGCT |
| | | TATCAAATGGAGTTAGTGTCTTAACCAGCAAAGTGTTAGACCTCAA |
| | | AAACTATATAGATAAACAATTGTTACCTATTGTGAACAAGCAAAGC |
| | | TGCAGCATATCAAATATAGAAACTGTGATAGAGTTCCAACAAAAGA |
| | | ACAACAGACTACTAGAGATTACCAGGGAATTTAGTGTTAATGCAGG |
| | | TGTAACTACACCTGTAAGCACTTACATGTTAACTAATAGTGAATTA |
| | | TTGTCATTAATCAATGATATGCCTATAACAAATGATCAGAAAAAGT |
| | | TAATGTCCAACAATGTTCAAATAGTTAGACAGCAAAGTTACTCTAT |
| | | CATGTCCATAATAAAGAGGAAGTCTTAGCATATGTAGTACAATTA |
| | | CCACTATATGGTGTTATAGATACACCCTGTTGGAAACTACACACAT |
| | | CCCCTCTATGTACAACCAACACAAAAGAAGGGTCCAACATCTGTTT |
| | | AACAAGAACTGACAGAGGATGGTACTGTGACAATGCAGGATCAGTA |
| | | TCTTTCTTCCCACAAGCTGAAACATGTAAAGTTCAATCAAATCGAG |
| | | TATTTTGTGACACAATGAACAGTTTAACATTACCAAGTGAAATAAA |
| | | TCTCTGCAATGTTGACATATTCAACCCCAAATATGATTGTAAAATT |
| | | ATGACTTCAAAAACAGATGTAAGCAGCTCCGTTATCACATCTCTAG |
| | | GAGCCATTGTGTCATGCTATGGCAAAACTAAATGTACAGCATCCAA |
| | | TAAAAATCGTGGAATCATAAAGACATTTTCTAACGGGTGCGATTAT |
| | | GTATCAAATAAAGGGATGGACACTGTGTCTGTAGGTAACACATTAT |
| | | ATTATGTAAATAAGCAAGAAGGTAAAAGTCTCTATGTAAAAGGTGA |
| | | ACCAATAATAAATTTCTATGACCCATTAGTATTCCCCTCTGATGAA |
| | | TTTGATGCATCAATATCTCAAGTCAACGAGAAGATTAACCAGAGCC |
| | | TAGCATTTATTCGTAAATCCGATGAATTATTACATAATGTAAATGC |
| | | TGGTAAATCCACCACAAATATCATGATAACTACTATAATTATAGTG |
| | | ATTATAGTAATATTGTTATCATTAATTGCTGTTGGACTGCTCTTAT |
| | | ACTGTAAGGCCAGAAGCACACCAGTCACACTAAGCAAAGATCAACT |
| | | GAGTGGTATAAATAATATTGCATTTAGTAACTAAATAAAAATAGCA |
| | | CCTAATCATGTTCTTACAATGGTTTACTATCTGCTCATAGACAACC |
| | | CATCTGTCATTGGATTTTCTTAAAATCTGAACTTCATCGAAACTCT |
| | | CATCTATAAACCATCTCACTTACACTATTTAAGTAGATTCCTAGTT |
| | | TATAGTTATATAAAACACAATTGAATGCCAGATTAACTTACCATCT |
| | | GTAAAAATGAAAACTGGGGCAAATATGTCACGAAGGAATCCTTGCA |
| | | AATTTGAAATTCGAGGTCATTGCTTAAATGGTAAGAGGTGTCATTT |
| | | TAGTCATAATTATTTTGAATGGCCACCCCATGCACTGCTTGTAAGA |
| | | CAAAACTTTATGTTAAACAGAATACTTAAGTCTATGGATAAAAGTA |
| | | TAGATACCTTATCAGAAATAAGTGGAGCTGCAGAGTTGGACAGAAC |
| | | AGAAGAGTATGCTCTTGGTGTAGTTGGAGTGCTAGAGAGTTATATA |
| | | GGATCAATAAACAATATAACTAAACAATCAGCATGTGTTGCCATGA |
| | | GCAAACTCCTCACTGAACTCAATAGTGATGATATCAAAAAGCTGAG |
| | | GGACAATGAAGAGCTAAATTCACCCAAGATAAGAGTGTACAATACT |
| | | GTCATATCATATATTGAAAGCAACAGGAAAAACAATAAACAAACTA |
| | | TCCATCTGTTAAAAAGATTGCCAGCAGACGTATTGAAGAAAACCAT |
| | | CAAAAACACATTGGATATCCATAAGAGCATAACCATCAACAACCCA |
| | | AAAGAATCAACTGTTAGTGATACAAATGACCATGCCAAAAATAATG |
| | | ATACTACCTGACAAATATCCTTGTAGTATAACTTCCATACTAATAA |
| | | CAAGTAGATGTAGAGTTACTATGTATAATCAAAAGAACACACTATA |
| | | TTTCAATCAAAACAACCCAAATAACCATATGTACTCACCGAATCAA |
| | | ACATTCAATGAAATCCATTGGACCTCTCAAGAATTGATTGACACAA |
| | | TTCAAATTTTTCTACAACATCTAGGTATTATTGAGGATATATATAC |
| | | AATATATATATTAGTGTCATAACACTCAATTCTAACACTCACCACA |
| | | TCGTTACATTATTAATTCAAACAATTCAAGTIGTGGGACAAAATGG |
| | | ATCCCATTATTAATGGAAATTCTGCTAATGTTTATCTAACCGATAG |
| | | TTATTTAAAAGGTGTTATCTCTTTCTCAGAGTGTAATGCTTTAGGA |
| | | AGTTACATATTCAATGGTCCTTATCTCAAAAATGATTATACCAACT |
| | | TAATTAGTAGACAAAATCCATTAATAGAACACATGAATCTAAAGAA |
| | | ACTAAATATAACACAGTCCTTAATATCTAAGTATCATAAAGGTGAA |
| | | ATAAAATTAGAAGAACCTACTTATTTTCAGTCATTACTTATGACAT |
| | | ACAAGAGTATGACCTCGTCAGAACAGATTGCTACCACTAATTTACT |

TABLE 15-continued

Table of Sequences

| SEQ ID NO: | Description | Sequence |
|---|---|---|
| | | TAAAAAGATAATAAGAAGAGCTATAGAAATAAGTGATGTCAAAGTC |
| | | TATGCTATATTGAATAAACTAGGGCTTAAAGAAAAGGACAAGATTA |
| | | AATCCAACAATGGACAAGATGAAGACAACTCAGTTATTACGACCAT |
| | | AATCAAAGATGATATACTTTCAGCTGTTAAAGATAATCAATCTCAT |
| | | CTTAAAGCAGACAAAAATCACTCTACAAAACAAAAAGACACAATCA |
| | | AAACAACACTCTTGAAGAAATTGATGTGTTCAATGCAACATCCTCC |
| | | ATCATGGTTAATACATTGGTTTAACTTATACACAAAATTAAACAAC |
| | | ATATTAACACAGTATCGATCAAATGAGGTAAAAAACCATGGGTTTA |
| | | CATTGATAGATAATCAAACTCTTAGTGGATTTCAATTTATTTTGAA |
| | | CCAATATGGTTGTATAGTTTATCATAAGGAACTCAAAAGAATTACT |
| | | GTGACAACCTATAATCAATTCTTGACATGGAAAGATATTAGCCTTA |
| | | GTAGATTAAATGTTTGTTTAATTACATGGATTAGTAACTGCTTGAA |
| | | CACATTAAATAAAAGCTTAGGCTTAAGATGCGGATTCAATAATGTT |
| | | ATCTTGACACAACTATTCCTTTATGGAGATTGTATACTAAAGCTAT |
| | | TTCACAATGAGGGGTTCTACATAATAAAAGAGGTAGAGGGATTTAT |
| | | TATGTCTCTAATTTTAAATATAACAGAAGAAGATCAATTCAGAAAA |
| | | CGATTTTATAATAGTATGCTCAACAACATCACAGATGCTGCTAATA |
| | | AAGCTCAGAAAAATCTGCTATCAAGAGTATGTCATACATTATTAGA |
| | | TAAGACAGTGTCCGATAATATAATAAATGGCAGATGGATAATTCTA |
| | | TTAAGTAAGTTCCTTAAATTAATTAAGCTTGCAGGTGACAATAACC |
| | | TTAACAATCTGAGTGAACTATATTTTTTGTTCAGAATATTTGGACA |
| | | CCCAATGGTAGATGAAAGACAAGCCATGGATGCTGTTAAAATTAAT |
| | | TGCAATGAGACCAAATTTTACTTGTTAAGCAGTCTGAGTATGTTAA |
| | | GAGGTGCCTTTATATATAGAATTATAAAAGGGTTTGTAAATAATTA |
| | | CAACAGATGGCCTACTTTAAGAAATGCTATTGTTTTACCCTTAAGA |
| | | TGGTTAACTTACTATAAACTAAACACTTATCCTTCTTTGTTGGAAC |
| | | TTACAGAAAGAGATTTGATTGTGTTATCAGGACTACGTTTCTATCG |
| | | TGAGTTTCGGTTGCCTAAAAAAGTGGATCTTGAAATGATTATAAAT |
| | | GATAAAGCTATATCACCTCCTAAAAATTTGATATGGACTAGTTTCC |
| | | CTAGAAATTACATGCCATCACACATACAAAACTATATAGAACATGA |
| | | AAAATTAAAATTTTCCGAGAGTGATAAATCAAGAAGAGTATTAGAG |
| | | TATTATTTAAGAGATAACAAATTCAATGAATGTGATTTATACAACT |
| | | GTGTAGTTAATCAAAGTTATCTCAACAACCCTAATCATGTGGTATC |
| | | ATTGACAGGCAAAGAAAGAGAACTCAGTGTAGGTAGAATGTTTGCA |
| | | ATGCAACCGGGAATGTTCAGACAGGTTCAAATATTGGCAGAGAAAA |
| | | TGATAGCTGAAAACATTTTACAATTCTTTCCTGAAAGTCTTACAAG |
| | | ATATGGTGATCTAGAACTACAAAAAATATTAGAATTGAAAGCAGGA |
| | | ATAAGTAACAAATCAAATCGCTACAATGATAATTACAACAATTACA |
| | | TTAGTAAGTGCTCTATCATCACAGATCTCAGCAAATTCAATCAAGC |
| | | ATTTCGATATGAAACGTCATGTATTTGTAGTGATGTGCTGGATGAA |
| | | CTGCATGGTGTACAATCTCTATTTTCCTGGTTACATTTAACTATTC |
| | | CTCATGTCACAATAATATGCACATATAGGCATGCACCCCCCTATAT |
| | | AGGAGATCATATTGTAGATCTTAACAATGTAGATGAACAAAGTGGA |
| | | TTATATAGATATCACATGGGTGGCATCGAAGGGTGGTGTCAAAAAC |
| | | TGTGGACCATAGAAGCTATATCACTATTGGATCTAATATCTCTCAA |
| | | AGGGAAATTCTCAATTACTGCTTTAATTAATGGTGACAATCAATCA |
| | | ATAGATATAAGCAAACCAATCAGACTCATGGAAGGTCAAACTCATG |
| | | CTCAAGCAGATTATTTGCTAGCATTAAATAGCCTTAAATTACTGTA |
| | | TAAAGAGTATGCAGGCATAGGCCACAAATTAAAAGGAACTGAGACT |
| | | TATATATCACGAGATATGCAATTTATGAGTAAAACAATTCAACATA |
| | | ACGGTGTATATTACCCAGCTAGTATAAAGAAAGTCCTAAGAGTGGG |
| | | ACCGTGGATAAACACTATACTTGATGATTTCAAAGTGAGTCTAGAA |
| | | TCTATAGGTAGTTTGACACAAGAATTAGAATATAGAGGTGAAAGTC |
| | | TATTATGCAGTTAATATTTAGAAATGTATGGTTATATAATCAGAT |
| | | TGCTCTACAATTAAAAAATCATGCATTATGTAACAATAAACTATAT |
| | | TTGGACATATTAAAGGTTCTGAAACACTTAAAAACCTTTTTTAATC |
| | | TTGATAATATTGATACAGCATTAACATTGTATATGAATTTACCCAT |
| | | GTTATTTGGTGGTGGTGATCCCAACTTGTTATATCGAAGTTTCTAT |
| | | AGAAGAACTCCTGACTTCCTCACAGAGGCTATAGTTCACTCTGTGT |
| | | TCATACTTAGTTATTATACAAACCATGACTTAAAAGATAAACTTCA |
| | | AGATCTGTCAGATGATAGATTGAATAAGTTCTTAACATGCATAATC |
| | | ACGTTTGACAAAAACCCTAATGCTGAATTCGTAACATTGATGAGAG |
| | | ATCCTCAAGCTTTAGGGTCTGAGAGACAAGCTAAAATTACTAGCGA |
| | | AATCAATAGACTGGCAGTTACAGAGGTTTTGAGTACAGCTCCAAAC |
| | | AAAATATTCTCCAAAAGTGCACAACATTATACTACTACAGAGATAG |
| | | ATCTAAATGATATTTATGCAAAATATAGAACCTACATATCCTCATGG |
| | | GCTAAGAGTTGTTTATGAAAGTTTACCCTTTTATAAAGCAGAGAAA |
| | | ATAGTAAATCTTATATCAGGTACAAAATCTATAACTAACATACTGG |
| | | AAAAAACTTCTGCCATAGACTTAACAGATATTGATAGAGCCACTGA |
| | | GATGATGAGGAAAAACATAACTTTGCTTATAAGGATACTTCCATTG |
| | | GATTGTAACAGAGATAAAGAGAGATATTGAGTATGGAAAACCTAA |
| | | GTATTACTGAATTAAGCAAATATGTTAGGGAAAGATCTTGGTCTTT |
| | | ATCCAATATAGTTGGTGTTACATCACCCAGTATCATGTATACAATG |
| | | GACATCAAATATACTACAAGCACTATATCTAGTGGCATAATTATAG |

TABLE 15-continued

| Table of Sequences | | |
| --- | --- | --- |

| SEQ ID NO: | Description | Sequence |
| --- | --- | --- |
| | | AGAAATATAATGTTAACAGTTTAACACGTGGTGAGAGAGGACCCAC |
| | | TAAACCATGGGTTGGTTCATCTACACAAGAGAAAAAAACAATGCCA |
| | | GTTTATAATAGACAAGTCTTAACCAAAAAACAGAGAGATCAAATAG |
| | | ATCTATTAGCAAAATTGGATTGGGTGTATGCATCTATAGATAACAA |
| | | GGATGAATTCATGGAAGAACTCAGCATAGGAACCCTTGGGTTAACA |
| | | TATGAAAAGGCCAAGAAATTATTTCCACAATATTTAAGTGTCAATT |
| | | ATTTGCATCGCCTTACAGTCAGTAGTAGACCATGTGAATTCCCTGC |
| | | ATCAATACCAGCTTATAGAACAACAAATTATCACTTTGACACTAGC |
| | | CCTATTAATCGCATATTAACAGAAAGTATGGTGATGAAGATATTG |
| | | ACATAGTATTCCAAAACTGTATAAGCTTTGGCCTTAGTTTAATGTC |
| | | AGTAGTAGAACAATTTACTAATGTATGTCCTAACAGAATTATTCTC |
| | | ATACCTAAGCTTAATGAGATACATTTGATGAAACCTCCCATATTCA |
| | | CAGGTGATGTTGATATTCACAAGTTAAAACAAGTGATACAAAACA |
| | | GCATATGTTTTTACCAGACAAAATAAGTTTGACTCAATATGTGGAA |
| | | TTATTCTTAAGTAATAAAACACTCAAATCTGGATCTCATGTTAATT |
| | | CTAATTTAATATTGGCACATAAAATATCTGACTATTTTCATAATAC |
| | | TTACATTTTAAGTACTAATTTAGCTGGACATTGGATTCTGATTATA |
| | | CAACTTATGAAAGATTCTAAAGGTATTTTTGAAAAAGATTGGGGAG |
| | | AGGGATATATAACTGATCATATGTTTATTAATTTGAAAGTTTTCTT |
| | | CAATGCTTATAAGACCTATCTCTTGTGTTTTCATAAAGGTTATGGC |
| | | AAAGCAAAGCTGGAGTGTGATATGAACACTTCAGATCTTCTATGTG |
| | | TATTGGAATTAATAGACAGTAGTTATTGGAAGTCTATGTCTAAGGT |
| | | ATTTTTAGAACAAAAAGTTATCAAATACATTCTTAGCCAAGATGCA |
| | | AGTTTACATAGAGTAAAAGGATGTCATAGCTTCAAATTATGGTTTC |
| | | TTAAACGTCTTAATGTAGCAGAATTCACAGTTTGCCCTTGGGTTGT |
| | | TAACATAGATTATCATCCAACACATATGAAAGCAATATTAACTTAT |
| | | ATAGATCTTGTTAGAATGGGATTGATAAATATAGATAGAATACACA |
| | | TTAAAAATAAACACAAATTCAATGATGAATTTTATACTTCTAATCT |
| | | CTTCTACATTAATTATAACTTCTCAGATAATACTCATCTATTAACT |
| | | AAACATATAAGGATTGCTAATTCTGAATTAGAAAATAATTACAACA |
| | | AATTATATCATCCTACACCAGAAACCCTAGAGAATATACTAGCCAA |
| | | TCCGATTAAAAGTAATGACAAAAAGACACTGAATGACTATTGTATA |
| | | GGTAAAAATGTTGACTCAATAATGTTACCATTGTTATCTAATAAGA |
| | | AGCTTATTAAATCGTCTGCAATGATTAGAACCAATTACAGCAAACA |
| | | AGATTTGTATAATTTATTCCCTATGGTTGTGATTGATAGAATTATA |
| | | GATCATTCAGGCAATACAGCCAAATCCAACCAACTTTACACTACTA |
| | | CTTCCCACCAAATATCTTTAGTCCACAATAGCACATCACTTTACTG |
| | | CATGCTTCCTTGGCATCATATTAATAGATTCAATTTTGTATTTAGT |
| | | TCTACAGGTTGTAAAATTAGTATAGAGTATATTTTAAAAGATCTTA |
| | | AAATTAAAGATCCCAATTGTATAGCATTCATAGGTGAAGGAGCAGG |
| | | GAATTTATTATTGCGTACAGTAGTGGAACTTCATCCTGACATAAGA |
| | | TATATTTACAGAAGTCTGAAAGATTGCAATGATCATAGTTTACCTA |
| | | TTGAGTTTTTAAGGCTGTACAATGGACATATCAACATTGATTATGG |
| | | TGAAAATTTGACCATTCCTGCTACAGATGCAACCAACAACATTCAT |
| | | TGGTCTTATTTACATATAAAGTTTGCTGAACCTATCAGTCTTTTTG |
| | | TCTGTGATGCCGAATTGTCTGTAACAGTCAACTGGAGTAAAATTAT |
| | | AATAGAATGGAGCAAGCATGTAAGAAAGTGCAAGTACTGTTCCTCA |
| | | GTTAATAAATGTATGTTAATAGTAAAATATCATGCTCAAGATGATA |
| | | TTGATTTCAAATTAGACAATATAACTATATTAAAAACTTATGTATG |
| | | CTTAGGCAGTAAGTTAAAGGGATCGGAGGTTTACTTAGTCCTTACA |
| | | ATAGGTCCTGCGAATATATTCCCAGTATTTAATGTAGTACAAAATG |
| | | CTAAATTGATACTATCAAGAACCAAAAATTTCATCATGCCTAAGAA |
| | | AGCTGATAAAGAGTCTATTGATGCAAATATTAAAAGTTTGATACCC |
| | | TTTCTTTGTTACCCTATAACAAAAAAAGGAATTAATACTGCATTGT |
| | | CAAAACTAAAGAGTGTTGTTAGTGGAGATATACTATCATATTCTAT |
| | | AGCTGGACGTAATGAAGTTTTCAGCAATAAACTTATAAATCATAAG |
| | | CATATGAACATCTTAAAATGGTTCAATCATGTTTTAAATTTCAGAT |
| | | CAACAGAACTAAACTATAACCATTTATATATGGTAGAATCTACATA |
| | | TCCTTACCTAAGTGAATTGTTAAACAGCTTGACAACCAATGAACTT |
| | | AAAAAACTGATTAAAATCACAGGTAGTCTGTTATACAACTTTCATA |
| | | ATGAATAATGAATAAAGATCTTATAATAAAAATTCCCATAGCTATA |
| | | CACTAACACTGTATTCAATTATAGTTATTAAAAATTAAAAATCATA |
| | | TAATTTTTTAAATAACTTTTAGTGAACTAATCCTAAAGTTATCATT |
| | | TTAATCTTGGAGGAATAAATTTAAACCCTAATCTAATTGGTTTATA |
| | | TGTGTATTAACTAAATTACGAGATATTAGTTTTTTGACACTTTTTT |
| | | CTCGTGGGTCGGCATGGCATCTCCACCTCCTCGCGGTCCGACCTGG |
| | | GCATCCGAAGGAGGACGCACGTCCACTCGGATGGCTAAGGGAGAGC |
| | | CTGCAGTAGCATAACCCCTTGGGGCCTCTAAACGGGTCTTGAGGGG |
| | | TTTTTTGGTGAAAGGAGGAACTATAGGCCGGCCCACCGCATATGTC |
| | | TCAGTACAATCTGCTCTGATGCCGCATAGCCATCACATTGTACACG |
| | | TGGACAAGTTGTCGCGGCCGCTTCTATAGTGTCACCTAAATACTAG |
| | | TGACTCCAGCGTAACTGGACTGGCCACAGTTAGGCCGCAAATGTAA |
| | | TCACACTGGCTCACCTTCGGGTGGGCCTTTCTGCGTTCGCGAGTGG |
| | | ACCCGATAAGCTCATGGAGCGGCGTAACCGTCGCACAGGAAGGACA |

TABLE 15-continued

Table of Sequences

| SEQ ID NO: | Description | Sequence |
|---|---|---|

GAGAAAGCGCGGATCTGGGAAGTGACGGACAGAACGGTCAGGACCT
GGATTGGGGAGGCGGTTGCCGCCGCTGCTGCTGACGGTGTGACGTT
CTCTGTTCCGGTCACACCACATACGTTCCGCCATTCCTATGCGATG
CACATGCTGTATGCCGGTATACCGCTGAAAGTTCTGCAAAGCCTGA
TGGGACATAAGTCCATCAGTTCAACGGAAGTCTACACGAAGGTTTT
TGCGCTGGATGTGGCTGCCCGGCACCGGGTGCAGTTTGCGATGCCG
GAGTCTGATGCGGTTGCGATGCTGAAACAATTATCCTGAGAATAAA
TGCCTTGGCCTTTATATGGAAATGTGGAACTGAGTGGATATGCTGT
TTTTGTCTGTTAAACAGAGAAGCTGGCTGTTATCCACTGAGAAGCG
AACGAAACAGTCGGGAAAATCTCCCATTATCGTAGAGATCCGCATT
ATTAATCTCAGGAGCCTGTGTAGCGTTTATAGGAAGTAGTGTTCTG
TCATGATGCCTGCAAGCGGTAACGAAAACGATTTGAATATGCCTTC
AGGAACAATAGAAATCTTCGTGCGGTGTTACGTTGAAGTGGAGCGG
ATTATGTCAGCAATGGACAGAACAACCTAATGAACACAGAACCATG
ATGTGGTCTGTCCTTTTACAGCCAGTAGTGCTCGCCGCAGTCGAGC
GACAGGGCGAAGCCCTCGGCTGGTTGCCCTCGCCGCTGGGCTGGCG
GCCGTCTATGGCCCTGCAAACGCGCCAGAAACGCCGTCGAAGCCGT
GTGCGAGACACCGCGGCCGGCCGCCGGCGTTGTGGATACCTCGCGG
AAAACTTGGCCCTCACTGACAGATGAGGGGCGGACGTTGACACTTG
AGGGGCCGACTCACCCGGCGCGGCGTTGACAGATGAGGGGCAGGCT
CGATTTCGGCCGGCGACGTGGAGCTGGCCAGCCTCGCAAATCGGCG
AAAACGCCTGATTTTACGCGAGTTTCCCACAGATGATGTGGACAAG
CCTGGGGATAAGTGCCCTGCGGTATTGACACTTGAGGGGCGCGACT
ACTGACAGATGAGGGGCGCGATCCTTGACACTTGAGGGGCAGAGTG
CTGACAGATGAGGGGCGCACCTATTGACATTTGAGGGGCTGTCCAC
AGGCAGAAAATCCAGCATTTGCAAGGGTTTCCGCCCGTTTTTCGGC
CACCGCTAACCTGTCTTTTAACCTGCTTTTAAACCAATATTTATAA
ACCTTGTTTTTAACCAGGGCTGCGCCCTGTGCGCGTGACCGCGCAC
GCCGAAGGGGGGTGCCCCCCCTTCTCGAACCCTCCCGGTCGAGTGA
GCGAGGAAGCACCAGGGAACAGCACTTATATATTCTGCTTACACAC
GATGCCTGAAAAAACTTCCCTTGGGGTTATCCACTTATCCACGGGG
ATATTTTTATAATTATTTTTTTTATAGTTTTTAGATCTTCTTTTTT
AGAGCGCCTTGTAGGCCTTTATCCATGCTGGTTCTAGAGAAGGTGT
TGTGACAAATTGCCCTTTCAGTGTGACAAATCACCCTCAAATGACA
GTCCTGTCTGTGACAAATTGCCCTTAACCCTGTGACAAATTGCCCT
CAGAAGAAGCTGTTTTTTCACAAAGTTATCCCTGCTTATTGACTCT
TTTTTATTTAGTGTGACAATCTAAAAACTTGTCACACTTCACATGG
ATCTGTCATGGCGGAAACAGCGGTTATCAATCACAAGAAACGTAAA
AATAGCCCGCGAATCGTCCAGTCAAACGACCTCACTGAGGCGGCAT
ATAGTCTCTCCCGGGATCAAAAACGTATGCTGTATCTGTTCGTTGA
CCAGATCAGAAAATCTGATGGCACCCTACAGGAACATGACGGTATC
TGCGAGATCCATGTTGCTAAATATGCTGAAATATTCGGATTGACCT
CTGCGGAAGCCAGTAAGGATATACGGCAGGCATTGAAGAGTTTCGC
GGGGAAGGAAGTGGTTTTTTATCGCCCTGAAGAGGATGCCGGCGAT
GAAAAAGGCTATGAATCTTTTCCTTGGTTTATCAAACGTGCGCACA
GTCCATCCAGAGGGCTTTACAGTGTACATATCAACCCATATCTCAT
TCCCTTCTTTATCGGGTTACAGAACCGGTTTACGCAGTTTCGGCTT
AGTGAAACAAAAGAAATCACCAATCCGTATGCCATGCGTTTATACG
AATCCCTGTGTCAGTATCGTAAGCCGGATGGCTCAGGCATCGTCTC
TCTGAAAATCGACTGGATCATAGAGCGTTACCAGCTGCCTCAAAGT
TACCAGCGTATGCCTGACTTCCGCCGCCGCTTCCTGCAGGTCTGTG
TTAATGAGATCAACAGCAGAACTCCAATGCGCCTCTCATACATTGA
GAAAAAGAAAGGCCGCCAGACGACTCATATCGTATTTTCCTTCCGC
GATATCACTTCCATGACGACAGGATAGTCTGAGGGTTATCTGTCAC
AGATTTGAGGGTGGTTCGTCACATTTGTTCTGACCTACTGAGGGTA
ATTTGTCACAGTTTTGCTGTTTCCTTCAGCCTGCATGGATTTTCTC
ATACTTTTTGAACTGTAATTTTTAAGGAAGCCAAATTTGAGGGCAG
TTTGTCACAGTTGATTTCCTTCTCTTTCCCTTCGTCATGTGACCTG
ATATCGGGGGTTAGTTCGTCATCATTGATGAGGGTTGATTATCACA
GTTTATTACTCTGAATTGGCTATCCGCGTGTGTACCTCTACCTGGA
GTTTTTCCCACGGTGGATATTTCTTCTTGCGCTGAGCGTAAGAGCT
ATCTGACAGAACAGTTCTTCTTTGCTTCCTCGCCAGTTCGCTCGCT
ATGCTCGGTTACACGGCTGCGGCGAGCGCTAGTGATAATAAGTGAC
TGAGGTATGTGCTCTTCTTATCTCCTTTTGTAGTGTTGCTCTTATT
TTAAACAACTTTGCGGTTTTTTGATGACTTTGCGATTTTGTTGTTG
CTTTGCAGTAAATTGCAAGATTTAATAAAAAAACGCAAAGCAATGA
TTAAAGGATGTTCAGAATGAAACTCATGGAAACACTTAACCAGTGC
ATAAACGCTGGTCATGAAATGACGAAGGCTATCGCCATTGCACAGT
TTAATGATGACAGCCCGGAAGCGAGGAAAATAACCCGGCGCTGGAG
AATAGGTGAAGCAGCGGATTTAGTTGGGGTTTCTTCTCAGGCTATC
AGAGATGCCGAGAAAGCAGGGCGACTACCGCACCCGGATATGGAAA
TTCGAGGACGGGTTGAGCAACGTGTTGGTTATACAATTGAACAAAT
TAATCATATGCGTGATGTGTTTGGTACGCGATTGCGACGTGCTGAA
GACGTATTTCCACCGGTGATCGGGGTTGCTGCCCATAAAGGAGGCG

TABLE 15-continued

| | | |
|---|---|---|

Table of Sequences

| SEQ ID NO: | Description | Sequence |
|---|---|---|
| | | TTTACAAAACCTCAGTTTCTGTTCATCTTGCTCAGGATCTGGCTCT |
| | | GAAGGGGCTACGTGTTTTGCTCGTGGAAGGTAACGACCCCCAGGGA |
| | | ACAGCCTCAATGTATCACGGATGGGTACCAGATCTTCATATTCATG |
| | | CAGAAGACACTCTCCTGCCTTTCTATCTTGGGGAAAAGGACGATGT |
| | | CACTTATGCAATAAAGCCCACTTGCTGGCCGGGGCTTGACATTATT |
| | | CCTTCCTGTCTGGCTCTGCACCGTATTGAAACTGAGTTAATGGGCA |
| | | AATTTGATGAAGGTAAACTGCCCACCGATCCACACCTGATGCTCCG |
| | | ACTGGCCATTGAAACTGTTGCTCATGACTATGATGTCATAGTTATT |
| | | GACAGCGCGCCTAACCTGGGTATCGGCACGATTAATGTCGTATGTG |
| | | CTGCTGATGTGCTGATTGTTCCCACGCCTGCTGAGTIGTTTGACTA |
| | | CACCTCCGCACTGCAGTTTTTCGATATGCTTCGTGATCTGCTCAAG |
| | | AACGTTGATCTTAAAGGGTTCGAGCCTGATGTACGTATTTTGCTTA |
| | | CCAAATACAGCAATAGTAATGGCTCTCAGTCCCCGTGGATGGAGGA |
| | | GCAAATTCGGGATGCCTGGGGAAGCATGGTTCTAAAAAATGTTGTA |
| | | CGTGAAACGGATGAAGTTGGTAAAGGTCAGATCCGGATGAGAACTG |
| | | TTTTTGAACAGGCCATTGATCAACGCTCTTCAACTGGTGCCTGGAG |
| | | AAATGCTCTTTCTATTTGGGAACCTGTCTGCAATGAAATTTTCGAT |
| | | CGTCTGATTAAACCACGCTGGGAGATTAGATAATGAAGCGTGCGCC |
| | | TGTTATTCCAAAACATACGCTCAATACTCAACCGGTTGAAGATACT |
| | | TCGTTATCGACACCAGCTGCCCCGATGGTGGATTCGTTAATTGCGC |
| | | GCGTAGGAGTAATGGCTCGCGGTAATGCCATTACTTTGCCTGTATG |
| | | TGGTCGGGATGTGAAGTTTACTCTTGAAGTGCTCCGGGGTGATAGT |
| | | GTTGAGAAGACCTCTCGGGTATGGTCAGGTAATGAACGTGACCAGG |
| | | AGCTGCTTACTGAGGACGCACTGGATGATCTCATCCCTTCTTTTCT |
| | | ACTGACTGGTCAACAGACACCGGCGTTCGGTCGAAGAGTATCTGGT |
| | | GTCATAGAAATTGCCGATGGGAGTCGCCGTCGTAAAGCTGCTGCAC |
| | | TTACCGAAAGTGATTATCGTGTTCTGGTTGGCGAGCTGGATGATGA |
| | | GCAGATGGCTGCATTATCCAGATTGGGTAACGATTATCGCCCAACA |
| | | AGTGCTTATGAACGTGGTCAGCGTTATGCAAGCCGATTGCAGAATG |
| | | AATTTGCTGGAAATATTTCTGCGCTGGCTGATGCGGAAAATATTTC |
| | | ACGTAAGATTATTACCCGCTGTATCAACACCGCCAAATTGCCTAAA |
| | | TCAGTTGTTGCTCTTTTTTCTCACCCCGGTGAACTATCTGCCCGGT |
| | | CAGGTGATGCACTTCAAAAAGCCTTTACAGATAAAGAGGAATTACT |
| | | TAAGCAGCAGGCATCTAACCTTCATGAGCAGAAAAAAGCTGGGGTG |
| | | ATATTTGAAGCTGAAGAAGTTATCACTCTTTTAACTTCTGTGCTTA |
| | | AAACGTCATCTGCATCAAGAACTAGTTTAAGCTCACGACATCAGTT |
| | | TGCTCCTGGAGCGACAGTATTGTATAAGGGCGATAAAATGGTGCTT |
| | | AACCTGGACAGGTCTCGTGTTCCAACTGAGTGTATAGAGAAAATTG |
| | | AGGCCATTCTTAAGGAACTTGAAAAGCCAGCACCCTGATGCGACCA |
| | | CGTTTTAGTCTACGTTTATCTGTCTTTACTTAATGTCCTTTGTTAC |
| | | AGGCCAGAAAGCATAACTGGCCTGAATATTCTCTCTGGGCCCACTG |
| | | TTCCACTTGTATCGTCGGTCTGATAATCAGACTGGGACCACGGTCC |
| | | CACTCGTATCGTCGGTCTGATTATTAGTCTGGGACCACGGTCCCAC |
| | | TCGTATCGTCGGTCTGATTATTAGTCTGGGACCACGGTCCCACTCG |
| | | TATCGTCGGTCTGATAATCAGACTGGGACCACGGTCCCACTCGTAT |
| | | CGTCGGTCTGATTATTAGTCTGGGACCATGGTCCCACTCGTATCGT |
| | | CGGTCTGATTATTAGTCTGGGACCACGGTCCCACTCGTATCGTCGG |
| | | TCTGATTATTAGTCTGGAACCACGGTCCCACTCGTATCGTCGGTC |
| | | GATTATTAGTCTGGGACCACGGTCCCACTCGTATCGTCGGTCTGAT |
| | | TATTAGTCTGGGACCACGATCCCACTCGTGTTGTCGGTCTGATTAT |
| | | CGGTCTGGGACCACGGTCCCACTTGTATTGTCGATCAGACTATCAG |
| | | CGTGAGACTACGATTCCATCAATGCCTGTCAAGGGCAAGTATTGAC |
| | | ATGGTCGTCGTAACCTGTAGAACGGAGTAACCTCGGTGTGCGGTTG |
| | | TATGCCTGCTGTGGATTGCTGCTGTGTCCTGCTTATCCACAACATT |
| | | TTGCGCACGGTTATGTGGACAAAATACCTGGTTACCCAGGCCGTGC |
| | | CGGCACGTTAACCGGGCTGCATCCGATGCAAGTGTGTCGCTGTCGA |
| | | CGAGCTCGCGAGCTCGGACATGAGGTTGCCCCGTATTCAGTGTCGC |
| | | TGATTTGTATTGTCTGAAGTTGCTTTTACGTTAAGTTGATGCAGAT |
| | | CAATTAATACGATACCTGCGTCATAATTGATTATTTGACGTGGTTT |
| | | GATGGCCTCCACGCACGTTGTGATATGTAGATGATAATCATTATCA |
| | | CTTTACGGGTCCTTTCCGGTGATCCGACAGGTTACGGGGCGGCGAC |
| | | CTCGCGGGTTTTCGCTATTTATGAAAATTTTCCGGTTTAAGGCGTT |
| | | TCCGTTCTTCTTCGTCATAACTTAATGTTTTTATTTAAAATACCCT |
| | | CTGAAAAGAAAGGAAACGACAGGTGCTGAAAGCGAGCTTTTTGGCC |
| | | TCTGTCGTTTCCTTTCTCTGTTTTTGTCCGTGGAATGAACAATGGA |
| | | AGTCCGAGCTCATCGCTAATAACTTCGTATAGCATACATTATACGA |
| | | AGTTATATTCGATGCGGCCGATCTAGCAGAAAGTCAAAAGCCTCCG |
| | | ACCGGAGGCTTTTGACTTCTGTCACCTAGGTTACGCCCCGCCCTGC |
| | | CACTCATCGCAGTACTGTTGTAATTCATTAAGCATTCTGCCGACAT |
| | | GGAAGCCATCACAAACGGCATGATGAACCTGAATCGCCAGCGGCAT |
| | | CAGCACCTTGTCGCCTTGCGTATAATATTTGCCCATGGTGAAAACG |
| | | GGGGCGAAGAAGTTGTCCATATTGGCCACGTTTAAATCAAACTGG |
| | | TGAAACTCACCCAGGGATTGGCTGAGACGAAAAACATATTCTCAAT |
| | | AAACCCTTTAGGGAAATAGGCCAGGTTTTCACCGTAACACGCCACA |

TABLE 15-continued

Table of Sequences

| SEQ ID NO: | Description | Sequence |
|---|---|---|
| | | TCTTGCGAATATATGTGTAGAAACTGCCGGAAATCGTCGTGGTATT |
| | | CACTCCAGAGCGATGAAAACGTTTCAGTTTGCTCATGGAAAACGGT |
| | | GTAACAAGGGTGAACACTATCCCATATCACCAGCTCACCGTCTTTC |
| | | ATTGCCATACGAAATTCCGGATGAGCATTCATCAGGCGGGCAAGAA |
| | | TGTGAATAAAGGCCGGATAAAACTTGTGCTTATTTTTCTTTACGGT |
| | | CTTTAAAAAGGCCGTAATATCCAGCTGAACGGTCTGGTTATAGGTA |
| | | CATTGAGCAACTGACTGAAATGCCTCAAAATGTTCTTTACGATGCC |
| | | ATTGGGATATATCAACGGTGGTATATCCAGTGATTTTTTTCTCCAT |
| | | TTTAGCTTCCTTAGCTCCTGAAAATCTCGATAACTCAAAAAATACG |
| | | CCCGGTAGTGATCTTATTTCATTATGGTGAAAGTTGGAACCTCTTA |
| | | CGTGCCGATCAGATTAAAACGAAAGGCCCAGTCTTTCGACTGAGCC |
| | | TTTCGTTTTATTTGACCATGTTGGTATGATTTAAATTCAGTGCGGC |
| | | CGCGACTTCAAGTCACGT |
| 22 | RSV A2 NLucP (without vector) NS1 CDS: nt 1-417 NS2 CDS: nt 530-901 N CDS: nt 1042-2214 P CDS: nt 2248-2970 Intergenic P-M region: nt 3145-3824 GS-Nluc-GE: nt 3149-3819 GS: nt 3149-3163 GE: nt 3803-3819 nanoLucP: nt 3164-3802 M CDS: nt 3834-4601 SH CDS: nt 4876-5067 G CDS: nt 5261-6154 F CDS: nt 6234-7955 M2-1 CDS: nt 8179-8760 M2-2 CDS: nt 8732-9001 L CDS: nt 9071-15,565 | ATGGGCAGCAATTCATTGAGTATGATAAAAGTTAGATTACAAAATT TGTTTGACAATGATGAAGTAGCATTGTTAAAAATAACATGCTATAC TGATAAATTAATACATTTAACTAACGCTTTGGCTAAGGCAGTGATA CATACAATCAAATTGAATGGCATTGTGTTTGTGCATGTTATTACAA GTAGTGATATTTGCCCTAATAATAATATTGTAGTAAAATCCAATTT CACAACAATGCCAGTACTACAAAATGGAGGTTATATATGGGAAATG ATGGAATTAACACATTGCTCTCAACCTAATGGTCTACTAGATGACA ATTGTGAAATTAAATTCTCCAAAAAACTAAGTGATTCAACAATGAC CAATTATATGAATCAATTATCTGAATTACTTGGATTTGATCTTAAT CCATAAATTATAATTAATATCAACTAGCAAATCAATGTCACTAACA CCATTAGTTAATATAAAACTTAACAGAAGACAAAAATGGGGCAAAT AAATCAATTCAGCCAACCCAACCATGGACACAACCCACAATGATAA TACACCACAAAGACTGATGATCACAGACATGAGACCGTTGTCACTT GAGACCATAATAACATCACTAACCAGAGACATCATAACACACAAAT TTATATACTTGATAAATCATGAATGCATAGTGAGAAAACTTGATGA AAAACAGGCCACATTTACATTCCTGGTCAACTATGAAATGAAACTA TTACACAAAGTAGGAAGCACTAAATATAAAAAAATATACTGAATACA ACACAAAATATGGCACTTTCCCTATGCCAATATTCATCAATCATGA TGGGTTCTTAGAATGCATTGGCATTAAGCCTACAAAGCATACTCCC ATAATATACAAGTATGATCTCAATCCATAAATTTCAACACAATATT CACACAATCTAAAACAACAACTCTATGCATAACTATACTCCATAGT CCAGATGGAGCCTGAAAATTATAGTGAATTTAAAATTAAGGAGGAT ATAAGATAGAAGATGGGGCAAATACAAAGATGGCTCTTAGCAAAGT CAAGTTGAATGATACACTCAACAAAGATCAACTTCTGTCATCCAGC AAATACACCATCCAACGGAGCACAGGAGATAGTATTGATACTCCTA ATTATGATGTGCAGAAACACATCATAAGTTATGTGGCATGCATGTTATT AATCACAGAAGATGCTAATCATAAATTCACTGGGTTAATAGGTATG TTATATGCGATGTCTAGGTTAGGAAGAGAAGACACCATAAAAATAC TCAGAGATGCGGGATATCATGTAAAAGCAAATGGAGTAGATGTAAC AACACATCGTCAAGACATTAATGGAAAAGAAATGAAATTTGAAGTG TTAACATTGGCAAGCTTAACAACTGAAATTCAAATCAACATTGAGA TAGAATCTAGAAAATCCTACAAAAAAATGCTAAAAGAAATGGGAGA GGTAGCTCCAGAATACAGGCATGACTCTCCTGATTGTGGGATGATA ATATTATGTATAGCAGCATTAGTAATAACTAAATTAGCAGCAGGGG ACAGATCTGGTCTTACAGCCGTGATTAGGAGAGCTAATAATGTCCT AAAAAATGAAATGAAACGTTACAAAGGCTTACTACCCAAGGACATA GCCAACAGCTTCTATGAAGTGTTTGAAAAACATCCCCACTTTATAG ATGTTTTTGTTCATTTTGGTATAGCACAATCTTCTACCAGAGGTGG CAGTAGAGTTGAAGGGATTTTTGCAGGATTGTTTATGAATGCCTAT GGTGCAGGGCAAGTGATGTTACGGTGGGGAGTCTTAGCAAAATCAG TTAAAAATATTATGTTAGGACATGCTAGTGTGCAAGCAGAAATGGA ACAAGTTGTTGAGGTTTATGAATATGCCCAAAAATTGGGTGGTGAA GCAGGATTCTACCATATATTGAACAACCCAAAAGCATCATTATTAT CTTTGACTCAATTTCCTCACTTCTCCAGTGTAGTATTAGGCAATGC TGCTGGCCTAGGCATAATGGGAGAGTACAGAGGTACACCGAGGAAT CAAGATCTATATGATGCAGCAAAGGCATATGCTGAACAACTCAAAG AAAATGGTGTGATTAACTACAGTGTACTAGACTTGACAGCAGAGA ACTAGAGGCTATCAAACATCAGCTTAATCCAAAAGATAATGATGTA GAGCTTTGAGTTAATAAAAAATGGGGCAAATAAATCATCATGGAAA AGTTTGCTCCTGAATTCCATGGAGAAGATGCAAACAACAGGGCTAC TAAATTCCTAGAATCAATAAAGGGCAAATTCACATCACCCAAAGAT CCCAAGAAAAAAGATAGTATCATATCTGTCAACTCAATAGATATAG AAGTAACCAAAGAAAGCCCTATAACATCAAATTCAACTATTATCAA CCCAACAAATGAGACAGATGATACTGCAGGGAACAAGCCCAATTAT CAAAGAAAACCTCTAGTAAGTTTCAAAGAGACCCTACACCAAGTG ATAATCCCTTTTCTAAACTATACAAAGAAACCATAGAAACATTTGA TAACAATGAGAAGAATCCAGCTATTCATACGAAGAAATAAATGAT CAGACAAACGATAATATAACAGCAAGATTAGATAGGATTGATGAAA AATTAAGTGAAATACTAGGAATGCTTCACACATTAGTAGTGGCAAG TGCAGGACCTACATCTGCTCGGGATGGTATAAGAGATGCCATGATT |

TABLE 15-continued

Table of Sequences

| SEQ ID NO: | Description | Sequence |
|---|---|---|

GGTTTAAGAGAAGAAATGATAGAAAAAATCAGAACTGAAGCATTAA
TGACCAATGACAGATTAGAAGCTATGGCAAGACTCAGGAATGAGGA
AAGTGAAAAGATGGCAAAAGACACATCAGATGAAGTGTCTCTCAAT
CCAACATCAGAGAAATTGAACAACCTATTGGAAGGGAATGATAGTG
ACAATGATCTATCACTTGAAGATTTCTGATTAGTTACCACTCTTCA
CATCAACACACAATACCAACAGAAGACCAACAAACTAACCAACCCA
ATCATCCAACCAAACATCCATCCGCCAATCAGCCAAACAGCCAACA
AAACAACCAGCCAATCCAAAACTAACCACCCGGAAAAAATCTATAA
TATAGTTACAAAAAAAGGAAGGGGCAAATAAATCAATGGTCTTCAC
ACTCGAAGATTTCGTTGGGGACTGGCGACAGACAGCCGGCTACAAC
CTGGACCAAGTCCTTGAACAGGGAGGTGTGTCCAGTTTGTTTCAGA
ATCTCGGGGTGTCCGTAACTCCGATCCAAAGGATTGTCCTGAGCGG
TGAAAATGGGCTGAAGATCGACATCCATGTCATCATCCCGTATGAA
GGTCTGAGCGGCGACCAAATGGGCCAGATCGAAAAAATTTTTAAGG
TGGTGTACCCTGTGGATGATCATCACTTTAAGGTGATCCTGCACTA
TGGCACACTGGTAATCGACGGGGTTACGCCGAACATGATCGACTAT
TTCGGACGGCCGTATGAAGGCATCGCCGTGTTCGACGGCAAAAAGA
TCACTGTAACAGGGACCCTGTGGAACGGCAACAAAATTATCGACGA
GCGCCTGATCAACCCCGACGGCTCCCTGCTGTTCCGAGTAACCATC
AACGGAGTGACCGGCTGGCGGCTGTGCGAACGCATTCTGGCGAATT
CTCACGGCTTTCCGCCTGAGGTTGAAGAGCAAGCCGCCGGTACATT
GCCTATGTCCTGCGCACAAGAAAGCGGTATGGACCGGCACCCAGCC
GCTTGTGCTTCAGCTCGCATCAACGTCTAAATTATAGTAATTTAAA
AAGGGTGGGGCAAATATGGAAACATACGTGAACAAGCTTCACGAAG
GCTCCACATACACAGCTGCTGTTCAATACAATGTCTTAGAAAAAGA
CGATGACCCTGCATCACTTACAATATGGGTGCCCATGTTCCAATCA
TCTATGCCAGCAGATTTACTTATAAAAGAACTAGCTAATGTCAACA
TACTAGTGAAACAAATATCCACACCCAAGGGACCTTCACTAAGAGT
CATGATAAACTCAAGAAGTGCAGTGCTAGCACAAATGCCCAGCAAA
TTTACCATATGCGCTAATGTGTCCTTGGATGAAAGAAGCAAACTAG
CATATGATGTAACCACACCCTGTGAAATCAAGGCATGTAGTCTAAC
ATGCCTAAAATCAAAAAAATATGTTGACTACAGTTAAAGATCTCACT
ATGAAGACACTCAACCCTACACATGATATTATTGCTTTATGTGAAT
TTGAAAACATAGTAACATCAAAAAAAGTCATAATACCAACATACCT
AAGATCCATCAGTGTCAGAAATAAAGATCTGAACACACTTGAAAAT
ATAACAACCACTGAATTCAAAAATGCTATCACAAATGCAAAAATCA
TCCCTTACTCAGGATTACTATTAGTCATCACAGTGACTGACAACAA
AGGAGCATTCAAATACATAAAGCCACAAAGTCAATTCATAGTAGAT
CTTGGAGCTTACCTAGAAAAAGAAAGTATATATTATGTTACCACAA
ATTGGAAGCACACAGCTACACGATTTGCAATCAAACCCATGGAAGA
TTAACCTTTTTCCTCTACATCAGTGTGTTAATTCATACAAACTTTC
TACCTACATTCTTCACTTCACCATCACAATCACAAACACTCTGTGG
TTCAACCAATCAAACAAAACTTATCTGAAGTCCCAGATCATCCCAA
GTCATTGTTTATCAGATCTAGTACTCAAATAAGTTAATAAAAAATA
TACACATGGGGCAAATAATCATTGGAGGAAATCCAACTAATCACAA
TATCTGTTAACATAGACAAGTCCACACACCATACAGAATCAACCAA
TGGAAAATACATCCATAACAATAGAATTCTCAAGCAAATTCTGGCC
TTACTTTACACTAATACACATGATCACAACAATAATCTCTTTGCTA
ATCATAATCTCCATCATGATTGCAATACTAAACAAACTTTGTGAAT
ATAACGTATTCCATAACAAAACCTTTGAGTTACCAAGAGCTCGAGT
CAACACATAGCATTCATCAATCCAACAGCCCAAAACAGTAACCTTG
CATTTAAAAATGAACAACCCCTACCTCTTTACAACACCTCATTAAC
ATCCCACCATGCAAACCACTATCCATACTATAAAGTAGTTAATTAA
AAATAGTCATAACAATGAACTAGGATATCAAGACTAACAATAACAT
TGGGGCAAATGCAAACATGTCCAAAAACAAGGACCAACGCACCGCT
AAGACATTAGAAAGGACCTGGGACACTCTCAATCATTTATTATTCA
TATCATCGTGCTTATATAAGTTAAATCTTAAATCTGTAGCACAAAT
CACATTATCCATTCTGGCAATGATAATCTCAACTTCACTTATAATT
GCAGCCATCATATTCATAGCCTCGGCAAACCACAAAGTCACACCAA
CAACTGCAATCATACAAGATGCAACAAGCCAGATCAAGAACACAAC
CCCAACATACCTCACCCAGAATCCTCAGCTTGGAATCAGTCCCTCT
AATCCGTCTGAAATTACATCACAAATCACCACCATACTAGCTTCAA
CAACACCAGGAGTCAAGTCAACCCTGCAATCCACAACAGTCAAGAC
CAAAAACACAACAACAACTCAAACACAACCCAGCAAGCCCACCACA
AAACAACGCCAAAACAAACCACCAAGCAAACCCAATAATGATTTTC
ACTTTGAAGTGTTCAACTTTGTACCCTGCAGCATATGCAGCAACAA
TCCAACCTGCTGGGCTATCTGCAAAAGAATACCAAACAAAAAACCA
GGAAAGAAACCACTACCAAGCCCACAAAAAAACCAACCCTCAAGA
CAACCAAAAAGATCCCAAACCTCAAACCACTAAATCAAAGGAAGT
ACCCACCACCAAGCCCACAGAAGAGCCAACCATCAACACCACCAAA
ACAAACATCATAACTACACTACTCACCTCCAACACCACAGGAAATC
CAGAACTCACAAGTCAAATGGAAACCTTCCACTCAACTTCCTCCGA
AGGCAATCCAAGCCCTTCTCAAGTCTCTACAACATCCGAGTACCCA
TCACAACCTTCATCTCCACCCAACACACCACGCCAGTAGTTACTTA

TABLE 15-continued

Table of Sequences

| SEQ ID NO: | Description | Sequence |
|---|---|---|
| | | AAAACATATTATCACAAAAAGCCATGACCAACTTAAACAGAATCAA |
| | | AATAAACTCTGGGGCAAATAACAATGGAGTTGCTAATCCTCAAAGC |
| | | AAATGCAATTACCACAATCCTCACTGCAGTCACATTTTGTTTTGCT |
| | | TCTGGTCAAAACATCACTGAAGAATTTTATCAATCAACATGCAGTG |
| | | CAGTTAGCAAAGGCTATCTTAGTGCTCTGAGAACTGGTTGGTATAC |
| | | CAGTGTTATAACTATAGAATTAAGTAATATCAAGGAAAATAAGTGT |
| | | AATGGAACAGATGCTAAGGTAAAATTGATAAAACAAGAATTAGATA |
| | | AATATAAAAATGCTGTAACAGAATTGCAGTTGCTCATGCAAAGCAC |
| | | ACCACCAACAAACAATCGAGCCAGAAGAGAACTACCAAGGTTTATG |
| | | AATTATACACTCAACAATGCCAAAAAAACCAATGTAACATTAAGCA |
| | | AGAAAAGGAAAAGAAGATTTCTTGTTTTTTTGTTAGGTGTTGGATC |
| | | TGCAATCGCCAGTGGCGTTGCTGTATCTAAGGTCCTGCACCTAGAA |
| | | GGGGAAGTGAACAAGATCAAAAGTGCTCTACTATCCACAAACAAGG |
| | | CTCTAGTCAGCTTATCAAATGGAGTTAGTGTCTTAACCAGCAAAGT |
| | | GTTAGACCTCAAAAACTATATAGATAAACAATTGTTACCTATTGTG |
| | | AACAAGCAAAGCTGCAGCATATCAAATATAGAAACTGTGATAGAGT |
| | | TCCAACAAAAGAACAACAGACTACTAGAGATTACCAGGGAATTTAG |
| | | TGTTAATGCAGGTGTAACTACACCTGTAAGCACTTACATGTTAACT |
| | | AATAGTGAATTATTGTCATTAATCAATGATATGCCTATAACAAATG |
| | | ATCAGAAAAAGTTAATGTCCAACAATGTTCAAATAGTTAGACAGCA |
| | | AAGTTACTCTATCATGTCCATAATAAAAGAGGAAGTCTTAGCATAT |
| | | GTAGTACAATTACCACTATATGGTGTTATAGATACACCCTGTTGGA |
| | | AACTACACACATCCCCTCTATGTACAACCAACACAAAAGAAGGGTC |
| | | CAACATCTGTTTAACAAGAACTGACAGAGGATGGTACTGTGACAAT |
| | | GCAGGATCAGTATCTTTCTTCCCACAAGCTGAAACATGTAAAGTTC |
| | | AATCAAATCGAGTATTTTGTGACACAATGAACAGTTTAACATTACC |
| | | AAGTGAAATAAATCTCTGCAATGTTGACATATTCAACCCCAAATAT |
| | | GATTGTAAAATTATGACTTCAAAAACAGATGTAAGCAGCTCCGTTA |
| | | TCACATCTCTAGGAGCCATTGTGTCATGCTATGGCAAAACTAAATG |
| | | TACAGCATCCAATAAAAATCGTGGAATCATAAAGACATTTTCTAAC |
| | | GGGTGCGATTATGTATCAAATAAAGGGATGGACACTGTGTCTGTAG |
| | | GTAACACATTATATTATGTAAATAAGCAAGAAGGTAAAAGTCTCTA |
| | | TGTAAAAGGTGAACCAATAATAAATTTCTATGACCCATTAGTATTC |
| | | CCCTCTGATGAATTTGATGCATCAATATCTCAAGTCAACGAGAAGA |
| | | TTAACCAGAGCCTAGCATTTATTCGTAAATCCGATGAATTATTACA |
| | | TAATGTAAATGCTGGTAAATCCACCACAAATATCATGATAACTACT |
| | | ATAATTATAGTGATTATAGTAATATTGTTATCATTAATTGCTGTTG |
| | | GACTGCTCTTATACTGTAAGGCCAGAAGCACACCAGTCACACTAAG |
| | | CAAAGATCAACTGAGTGGTATAAATAATATTGCATTTAGTAACTAA |
| | | ATAAAAATAGCACCTAATCATGTTCTTACAATGGTTTACTATCTGC |
| | | TCATAGACAACCCATCTGTCATTGGATTTTCTTAAAATCTGAACTT |
| | | CATCGAAACTCTCATCTATAAACCATCTCACTTACACTATTTAAGT |
| | | AGATTCCTAGTTTATAGTTATATAAAACACAATTGAATGCCAGATT |
| | | AACTTACCATCTGTAAAAATGAAAACTGGGGCAAATATGTCACGAA |
| | | GGAATCCTTGCAAATTTGAAATTCGAGGTCATTGCTTAAATGGTAA |
| | | GAGGTGTCATTTTAGTCATAATTATTTTGAATGGCCACCCCATGCA |
| | | CTGCTTGTAAGACAAAACTTTATGTTAAACAGAATACTTAAGTCTA |
| | | TGGATAAAAGTATAGATACCTTATCAGAAATAAGTGGAGCTGCAGA |
| | | GTTGGACAGAACAGAAGAGTATGCTCTTGGTGTAGTTGGAGTGCTA |
| | | GAGAGTTATATAGGATCAATAAACAATATAACTAAACAATCAGCAT |
| | | GTGTTGCCATGAGCAAACTCCTCACTGAACTCAATAGTGATGATAT |
| | | CAAAAAGCTGAGGGACAATGAAGAGCTAAATTCACCCAAGATAAGA |
| | | GTGTACAATACTGTCATATCATATATTGAAAGCAACAGGAAAAACA |
| | | ATAAACAAACTATCCATCTGTTAAAAAGATTGCCAGCAGACGTATT |
| | | GAAGAAAACCATCAAAAACACATTGGATATCCATAAGAGCATAACC |
| | | ATCAACAACCCAAAAGAATCAACTGTTAGTGATACAAATGACCATG |
| | | CCAAAAATAATGATACTACCTGACAAATATCCTTGTAGTATAACTT |
| | | CCATACTAATAACAAGTAGATGTAGAGTTACTATGTATAATCAAAA |
| | | GAACACACTATATTTCAATCAAAACAACCCAAATAACCATATGTAC |
| | | TCACCGAATCAAACATTCAATGAAATCCATTGGACCTCTCAAGAAT |
| | | TGATTGACACAATTCAAATTTTTCTACAACATCTAGGTATTATTGA |
| | | GGATATATATACAATATATATATTAGTGTCATAACACTCAATTCTA |
| | | ACACTCACCACATCGTTACATTATTAATTCAAACAATTCAAGTTGT |
| | | GGGACAAAATGGATCCCATTATTAATGGAAATTCTGCTAATGTTTA |
| | | TCTAACCGATAGTTATTTAAAAGGTGTTATCTCTTTCTCAGAGTGT |
| | | AATGCTTTAGGAAGTTACATATTCAATGGTCCTTATCTCAAAAATG |
| | | ATTATACCAACTTAATTAGTAGACAAAATCCATTAATAGAACACAT |
| | | GAATCTAAAGAAACTAAATATAACACAGTCCTTAATATCTAAGTAT |
| | | CATAAAGGTGAAATAAAATTAGAAGAACCTACTTATTTTCAGTCAT |
| | | TACTTATGACATACAAGAGTATGACCTCGTCAGAACAGATTGCTAC |
| | | CACTAATTTACTTAAAAAGATAATAAGAAGAGCTATAGAAATAAGT |
| | | GATGTCAAAGTCTATGCTATATTGAATAAACTAGGGCTTAAAGAAA |
| | | AGGACAAGATTAAATCCAACAATGGACAAGATGAAGACAACTCAGT |
| | | TATTACGACCATAATCAAAGATGATATACTTTCAGCTGTTAAAGAT |

TABLE 15-continued

Table of Sequences

| SEQ ID NO: | Description | Sequence |
|---|---|---|
| | | AATCAATCTCATCTTAAAGCAGACAAAAATCACTCTACAAAACAAA |
| | | AAGACACAATCAAAACAACACTCTTGAAGAAATTGATGTGTTCAAT |
| | | GCAACATCCTCCATCATGGTTAATACATTGGTTTAACTTATACACA |
| | | AAATTAAACAACATATTAACACAGTATCGATCAAATGAGGTAAAAA |
| | | ACCATGGGTTTACATTGATAGATAATCAAACTCTTAGTGGATTTCA |
| | | ATTTATTTTGAACCAATATGGTTGTATAGTTTATCATAAGGAACTC |
| | | AAAAGAATTACTGTGACAACCTATAATCAATTCTTGACATGGAAAG |
| | | ATATTAGCCTTAGTAGATTAAATGTTTGTTTAATTACATGGATTAG |
| | | TAACTGCTTGAACACATTAAATAAAAGCTTAGGCTTAAGATGCGGA |
| | | TTCAATAATGTTATCTTGACACAACTATTCCTTTATGGAGATTGTA |
| | | TACTAAAGCTATTTCACAATGAGGGGTTCTACATAATAAAAGAGGT |
| | | AGAGGGATTTATTATGTCTCTAATTTTAAATATAACAGAAGAAGAT |
| | | CAATTCAGAAAACGATTTTATAATAGTATGCTCAACAACATCACAG |
| | | ATGCTGCTAATAAAGCTCAGAAAAATCTGCTATCAAGAGTATGTCA |
| | | TACATTATTAGATAAGACAGTGTCCGATAATATAATAAATGGCAGA |
| | | TGGATAATTCTATTAAGTAAGTTCCTTAAATTAATTAAGCTTGCAG |
| | | GTGACAATAACCTTAACAATCTGAGTGAACTATATTTTTTGTTCAG |
| | | AATATTTGGACACCCAATGGTAGATGAAAGACAAGCCATGGATGCT |
| | | GTTAAAATTAATTGCAATGAGACCAAATTTTACTTGTTAAGCAGTC |
| | | TGAGTATGTTAAGAGGTGCCTTTATATATAGAATTATAAAAGGGTT |
| | | TGTAAATAATTACAACAGATGGCCTACTTTAAGAAATGCTATTGTT |
| | | TTACCCTTAAGATGGTTAACTTACTATAAACTAAACACTTATCCTT |
| | | CTTTGTTGGAACTTACAGAAAGAGATTTGATTGTGTTATCAGGACT |
| | | ACGTTTCTATCGTGAGTTTCGGTTGCCTAAAAAAGTGGATCTTGAA |
| | | ATGATTATAAATGATAAAGCTATATCACCTCCTAAAAATTTGATAT |
| | | GGACTAGTTTCCCTAGAAATTACATGCCATCACACATACAAAACTA |
| | | TATAGAACATGAAAAATTAAAATTTTCCGAGAGTGATAAATCAAGA |
| | | AGAGTATTAGAGTATTATTTAAGAGATAACAAATTCAATGAATGTG |
| | | ATTTATACAACTGTGTAGTTAATCAAAGTTATCTCAACAACCCTAA |
| | | TCATGTGGTATCATTGACAGGCAAAGAAAGAGAACTCAGTGTAGGT |
| | | AGAATGTTTGCAATGCAACCGGGAATGTTCAGACAGGTTCAAATAT |
| | | TGGCAGAGAAAATGATAGCTGAAAACATTTTACAATTCTTTCCTGA |
| | | AAGTCTTACAAGATATGGTGATCTAGAACTACAAAAAATATTAGAA |
| | | TTGAAAGCAGGAATAAGTAACAAATCAAATCGCTACAATGATAATT |
| | | ACAACAATTACATTAGTAAGTGCTCTATCATCACAGATCTCAGCAA |
| | | ATTCAATCAAGCATTTCGATATGAAACGTCATGTATTTGTAGTGAT |
| | | GTGCTGGATGAACTGCATGGTGTACAATCTCTATTTTCCTGGTTAC |
| | | ATTTAACTATTCCTCATGTCACAATAATATGCACATATAGGCATGC |
| | | ACCCCCCTATATAGGAGATCATATTGTAGATCTTAACAATGTAGAT |
| | | GAACAAAGTGGATTATATAGATATCACATGGGTGGCATCGAAGGGT |
| | | GGTGTCAAAAACTGTGGACCATAGAAGCTATATCACTATTGGATCT |
| | | AATATCTCTCAAAGGGAAATTCTCAATTACTGCTTTAATTAATGGT |
| | | GACAATCAATCAATAGATATAAGCAAACCAATCAGACTCATGGAAG |
| | | GTCAAACTCATGCTCAAGCAGATTATTTGCTAGCATTAAATAGCCT |
| | | TAAATTACTGTATAAAGAGTATGCAGGCATAGGCCACAAATTAAAA |
| | | GGAACTGAGACTTATATATCACGAGATATGCAATTTATGAGTAAAA |
| | | CAATTCAACATAACGGTGTATATTACCCAGCTAGTATAAAGAAAGT |
| | | CCTAAGAGTGGGACCGTGGATAAACACTATACTTGATGATTTCAAA |
| | | GTGAGTCTAGAATCTATAGGTAGTTTGACACAAGAATTAGAATATA |
| | | GAGGTGAAAGTCTATTATGCAGTTTAATATTTAGAAATGTATGGTT |
| | | ATATAATCAGATTGCTCTACAATTAAAAAAATCATGCATTATGTAAC |
| | | AATAAACTATATTTGGACATATTAAAGGTTCTGAAACACTTAAAAA |
| | | CCTTTTTTAATCTTGATAATATTGATACAGCATTAACATTGTATAT |
| | | GAATTTACCCATGTTATTTGGTGGTGGTGATCCCAACTTGTTATAT |
| | | CGAAGTTTCTATAGAAGAACTCCTGACTTCCTCACAGAGGCTATAG |
| | | TTCACTCTGTGTTCATACTTAGTTATTATACAAACCATGACTTAAA |
| | | AGATAAACTTCAAGATCTGTCAGATGATAGATTGAATAAGTTCTTA |
| | | ACATGCATAATCACGTTTGACAAAAACCCTAATGCTGAATTCGTAA |
| | | CATTGATGAGAGATCCTCAAGCTTTAGGGTCTGAGAGACAAGCTAA |
| | | AATTACTAGCGAAATCAATAGACTGGCAGTTACAGAGGTTTTGAGT |
| | | ACAGCTCCAAACAAAATATTCTCCAAAAGTGCACAACATTATACTA |
| | | CTACAGAGATAGATCTAAATGATATTATGCAAAATATAGAACCTAC |
| | | ATATCCTCATGGGCTAAGAGTTGTTTATGAAAGTTTACCCTTTTAT |
| | | AAAGCAGAGAAAATAGTAAATCTTATATCAGGTACAAAATCTATAA |
| | | CTAACATACTGGAAAAAACTTCTGCCATAGACTTAACAGATATTGA |
| | | TAGAGCCACTGAGATGATGAGGAAAAACATAACTTTGCTTATAAGG |
| | | ATACTTCCATTGGATTGTAACAGAGATAAAAGAGAGATATTGAGTA |
| | | TGGAAAACCTAAGTATTACTGAATTAAGCAAATATGTTAGGGAAAG |
| | | ATCTTGGTCTTTATCCAATATAGTTGGTGTTACATCACCCAGTATC |
| | | ATGTATACAATGGACATCAAATATACTACAAGCACTATATCTAGTG |
| | | GCATAATTATAGAGAAATATAATGTTAACAGTTTAACACGTGGTGA |
| | | GAGAGGACCCACTAAACCATGGGTTGGTTCATCTACACAAGAGAAA |
| | | AAAACAATGCCAGTTTATAATAGACAAGTCTTAACCAAAAAACAGA |
| | | GAGATCAAATAGATCTATTAGCAAAATTGGATTGGGTGTATGCATC |

TABLE 15-continued

Table of Sequences

| SEQ ID NO: | Description | Sequence |
|---|---|---|
| | | TATAGATAACAAGGATGAATTCATGGAAGAACTCAGCATAGGAACC |
| | | CTTGGGTTAACATATGAAAAGGCCAAGAAATTATTTCCACAATATT |
| | | TAAGTGTCAATTATTTGCATCGCCTTACAGTCAGTAGTAGACCATG |
| | | TGAATTCCCTGCATCAATACCAGCTTATAGAACAACAAATTATCAC |
| | | TTTGACACTAGCCCTATTAATCGCATATTAACAGAAAAGTATGGTG |
| | | ATGAAGATATTGACATAGTATTCCAAAACTGTATAAGCTTTGGCCT |
| | | TAGTTTAATGTCAGTAGTAGAACAATTTACTAATGTATGTCCTAAC |
| | | AGAATTATTCTCATACCTAAGCTTAATGAGATACATTTGATGAAAC |
| | | CTCCCATATTCACAGGTGATGTTGATATTCACAAGTTAAAACAAGT |
| | | GATACAAAAACAGCATATGTTTTTACCAGACAAAATAAGTTTGACT |
| | | CAATATGTGGAATTATTCTTAAGTAATAAAACACTCAAATCTGGAT |
| | | CTCATGTTAATTCTAATTTAATATTGGCACATAAAATATCTGACTA |
| | | TTTTCATAATACTTACATTTTAAGTACTAATTTAGCTGGACATTGG |
| | | ATTCTGATTATACAACTTATGAAAGATTCTAAAGGTATTTTTGAAA |
| | | AAGATTGGGGAGAGGGATATATAACTGATCATATGTTTATTAATTT |
| | | GAAAGTTTTCTTCAATGCTTATAAGACCTATCTCTTGTGTTTTCAT |
| | | AAAGGTTATGGCAAAGCAAAGCTGGAGTGTGATATGAACACTTCAG |
| | | ATCTTCTATGTGTATTGGAATTAATAGACAGTAGTTATTGGAAGTC |
| | | TATGTCTAAGGTATTTTTAGAACAAAAAGTTATCAAATACATTCTT |
| | | AGCCAAGATGCAAGTTTACATAGAGTAAAAGGATGTCATAGCTTCA |
| | | AATTATGGTTTCTTAAACGTCTTAATGTAGCAGAATTCACAGTTTG |
| | | CCCTTGGGTTGTTAACATAGATTATCATCCAACACATATGAAAGCA |
| | | ATATTAACTTATATAGATCTTGTTAGAATGGGATTGATAAATATAG |
| | | ATAGAATACACATTAAAAATAAACACAAATTCAATGATGAATTTTA |
| | | TACTTCTAATCTCTTCTACATTAATTATAACTTCTCAGATAATACT |
| | | CATCTATTAACTAAACATATAAGGATTGCTAATTCTGAATTAGAAA |
| | | ATAATTACAACAAATTATATCATCCTACACCAGAAACCCTAGAGAA |
| | | TATACTAGCCAATCCGATTAAAAGTAATGACAAAAAGACACTGAAT |
| | | GACTATTGTATAGGTAAAAATGTTGACTCAATAATGTTACCATTGT |
| | | TATCTAATAAGAAGCTTATTAAATCGTCTGCAATGATTAGAACCAA |
| | | TTACAGCAAACAAGATTTGTATAATTTATTCCCTATGGTTGTGATT |
| | | GATAGAATTATAGATCATTCAGGCAATACAGCCAAATCCAACCAAC |
| | | TTTACACTACTACTTCCCACCAAATATCTTTAGTCCACAATAGCAC |
| | | ATCACTTTACTGCATGCTTCCTTGGCATCATATTAATAGATTCAAT |
| | | TTTGTATTTAGTTCTACAGGTTGTAAAATTAGTATAGAGTATATTT |
| | | TAAAAGATCTTAAAATTAAAGATCCCAATTGTATAGCATTCATAGG |
| | | TGAAGGAGCAGGGAATTTATTATTGCGTACAGTAGTGGAACTTCAT |
| | | CCTGACATAAGATATATTTACAGAAGTCTGAAAGATTGCAATGATC |
| | | ATAGTTTACCTATTGAGTTTTTAAGGCTGTACAATGGACATATCAA |
| | | CATTGATTATGGTGAAAATTTGACCATTCCTGCTACAGATGCAACC |
| | | AACAACATTCATTGGTCTTATTTACATATAAAGTTTGCTGAACCTA |
| | | TCAGTCTTTTTGTCTGTGATGCCGAATTGTCTGTAACAGTCAACTG |
| | | GAGTAAAATTATAATAGAATGGAGCAAGCATGTAAGAAAGTGCAAG |
| | | TACTGTTCCTCAGTTAATAAATGTATGTTAATAGTAAAATATCATG |
| | | CTCAAGATGATATTGATTTCAAATTAGACAATATAACTATATTAAA |
| | | AACTTATGTATGCTTAGGCAGTAAGTTAAAGGGATCGGAGGTTTAC |
| | | TTAGTCCTTACAATAGGTCCTGCGAATATATTCCCAGTATTTAATG |
| | | TAGTACAAAATGCTAAATTGATACTATCAAGAACCAAAAATTTCAT |
| | | CATGCCTAAGAAAGCTGATAAAGAGTCTATTGATGCAAATATTAAA |
| | | AGTTTGATACCCTTTCTTTGTTACCCTATAACAAAAAAAGGAATTA |
| | | ATACTGCATTGTCAAAACTAAAGAGTGTTGTTAGTGGAGATATACT |
| | | ATCATATTCTATAGCTGGACGTAATGAAGTTTTCAGCAATAAACTT |
| | | ATAAATCATAAGCATATGAACATCTTAAAATGGTTCAATCATGTTT |
| | | TAAATTTCAGATCAACAGAACTAAACTATAACCATTTATATATGGT |
| | | AGAATCTACATATCCTTACCTAAGTGAATTGTTAAACAGCTTGACA |
| | | ACCAATGAACTTAAAAAACTGATTAAAAATCACAGGTAGTCTGTTAT |
| | | ACAACTTTCATAATGAA |

All references cited herein are incorporated by reference to the same extent as if each individual publication, database entry (e.g. Genbank sequences or GeneID entries), patent application, or patent, was specifically and individually indicated to be incorporated by reference. This statement of incorporation by reference is intended by Applicants, pursuant to 37 C.F.R. § 1.57(b)(1), to relate to each and every individual publication, database entry (e.g. Genbank sequences or GeneID entries), patent application, or patent, each of which is clearly identified in compliance with 37 C.F.R. § 1.57(b)(2), even if such citation is not immediately adjacent to a dedicated statement of incorporation by reference. The inclusion of dedicated statements of incorporation by reference, if any, within the specification does not in any way weaken this general statement of incorporation by reference. Citation of the references herein is not intended as an admission that the reference is pertinent prior art, nor does it constitute any admission as to the contents or date of these publications or documents. To the extent that the references provide a definition for a claimed term that conflicts with the definitions provided in the instant specification, the definitions provided in the instant specification shall be used to interpret the claimed invention.

The invention claimed is:

1. An expression vector for producing an infectious recombinant respiratory syncytial virus (RSV) comprising:
   a) a nucleic acid sequence encoding a respiratory syncytial virus; and
   b) a reporter gene flanked by an RSV gene start sequence and an RSV gene end sequence, the reporter gene and flanking RSV gene start and RSV gene end sequences located between the P and M genes of the respiratory syncytial virus;
   wherein the RSV gene start sequence is SEQ ID NO: 16 and the RSV gene end sequence is SEQ ID NO: 17; and
   wherein the reporter gene encodes a luminescent enzyme that catalyzes a luminescent substrate; or the reporter gene encodes a fluorescent protein.

2. The expression vector of claim 1, wherein the sequence of the reporter gene is SEQ ID NO: 18.

3. The expression vector of claim 1, wherein the reporter gene flanked by the RSV gene start and gene end sequences is SEQ ID NO: 15.

4. The expression vector of claim 1, wherein the respiratory syncytial virus is strain A2 or comprises SEQ ID NO: 14.

5. A respiratory syncytial virus comprising:
   a) a nucleic acid sequence encoding a respiratory syncytial virus; and
   b) a reporter gene flanked by an RSV gene start sequence and an RSV gene end sequence, the reporter gene and flanking RSV gene start and RSV gene end sequences located between the P and M genes of the respiratory syncytial virus;
   wherein the RSV gene start sequence is SEQ ID NO: 16 and the RSV gene end sequence is SEQ ID NO: 17; and
   wherein the reporter gene encodes a luminescent enzyme that catalyzes a luminescent substrate; or the reporter gene encodes a fluorescent protein.

6. The respiratory syncytial virus of claim 5, wherein the sequence of the reporter gene is SEQ ID NO: 18.

7. The respiratory syncytial virus of claim 5, wherein the reporter gene flanked by the RSV gene start and gene end sequences is SEQ ID NO: 15.

8. The respiratory syncytial virus of claim 5, wherein the respiratory syncytial virus is strain A2 or comprises SEQ ID NO: 14.

9. A method for measuring the activity of an anti-respiratory syncytial virus (RSV) antibody or antigen binding fragment thereof, the method comprising:

a) combining (i) the anti-RSV antibody or antigen binding fragment thereof, (ii) an RSV virus comprising a reporter gene, and (iii) one or more cells infectable by the RSV virus; and b) detecting expression of the reporter gene;

wherein the RSV virus comprises i) a nucleic acid sequence encoding a respiratory syncytial virus; and ii) the reporter gene flanked by an RSV gene start sequence and an RSV gene end sequence, the reporter gene and flanking RSV gene start and RSV gene end sequences located between the P and M genes of the respiratory syncytial virus, wherein the reporter gene encodes a luminescent enzyme that catalyzes a luminescent substrate, and detecting expression of the reporter gene comprises detecting luminescence of the luminescent substrate, or wherein the reporter gene encodes a fluorescent protein, and detecting expression of the reporter gene comprises detecting fluorescent light emission from the fluorescent protein.

10. The method of claim 9, wherein the anti-RSV antibody or antigen binding fragment thereof of (i) is combined with the RSV virus (ii) before adding the combined mixture of (i) and (ii) to the one or more cells infectable by the RSV virus of (iii).

11. The method of claim 9, wherein the luminescent enzyme is a luciferase.

12. The method of claim 11, further comprising a step of adding a luciferase substrate.

13. The method of claim 9, wherein the one or more cells infectable by the RSV virus are A549 cells.

14. The method of claim 11, wherein the nucleic acid sequence encoding the luciferase encodes a nanoluciferase.

15. The method of claim 9, wherein the anti-RSV antibody or antigen binding fragment thereof comprises:

(a) three heavy chain complementarity determining regions (HC-CDRs), wherein HC-CDR1 is SEQ ID NO: 1, HC-CDR2 is SEQ ID NO: 2, and HC-CDR3 is SEQ ID NO: 3; and (b) three light chain complementarity determining regions (LC-CDRs), wherein LC-CDR1 is SEQ ID NO: 4, LC-CDR2 is SEQ ID NO: 5, and LC-CDR3 is SEQ ID NO: 6.

16. The method of claim 9, wherein the anti-RSV antibody or antigen binding fragment thereof comprises a heavy chain variable region of SEQ ID NO: 7 and a light chain variable region of SEQ ID NO: 8.

17. The method of claim 9, wherein the anti-RSV antibody or antigen binding fragment thereof comprises a heavy chain and a light chain, and wherein the heavy chain comprises SEQ ID NO: 9 and the light chain comprises SEQ ID NO: 10.

18. The method of claim 9, wherein the anti-RSV antibody or antigen binding fragment thereof is an antibody comprising two heavy chains of SEQ ID NO: 9 and two light chains of SEQ ID NO: 10.

19. The method of claim 9, wherein the sequence of the reporter gene is SEQ ID NO: 18.

20. The method of claim 9, wherein the reporter gene flanked by an RSV gene start sequence and an RSV gene end sequence is SEQ ID NO: 15.

21. The method of claim 9, wherein the respiratory syncytial virus is strain A2 or comprises SEQ ID NO: 14.

* * * * *